(12) United States Patent
Goldberg et al.

(10) Patent No.: US 12,144,738 B2
(45) Date of Patent: Nov. 19, 2024

(54) HUMERAL ARTHROPLASTY

(71) Applicant: CATALYST ORTHOSCIENCE INC., Naples, FL (US)

(72) Inventors: Steven Scott Goldberg, Naples, FL (US); Daniel F. Justin, Orlando, FL (US)

(73) Assignee: Catalyst Orthoscience Inc., Naples, FL (US)

( * ) Notice: Subject to any disclaimer, the term of this patent is extended or adjusted under 35 U.S.C. 154(b) by 876 days.

(21) Appl. No.: 17/168,290

(22) Filed: Feb. 5, 2021

(65) Prior Publication Data

US 2021/0154019 A1    May 27, 2021

Related U.S. Application Data

(63) Continuation of application No. 16/375,850, filed on Apr. 4, 2019, now Pat. No. 10,925,744, which is a continuation of application No. 15/629,182, filed on Jun. 21, 2017, now Pat. No. 10,265,185, which is a continuation of application No. 15/042,601, filed on Feb. 12, 2016, now Pat. No. 9,814,587, which is a continuation of application No. 14/069,154, filed on Oct. 31, 2013, now Pat. No. 9,289,306.

(60) Provisional application No. 61/794,348, filed on Mar. 15, 2013.

(51) Int. Cl.
*A61F 2/40* (2006.01)
*A61B 17/16* (2006.01)
*A61B 17/17* (2006.01)
*A61F 2/46* (2006.01)
*A61F 2/30* (2006.01)

(52) U.S. Cl.
CPC ........ *A61F 2/4014* (2013.01); *A61B 17/1657* (2013.01); *A61B 17/1684* (2013.01); *A61B 17/1778* (2016.11); *A61F 2/4003* (2013.01); *A61F 2/4612* (2013.01); *A61F 2002/30273* (2013.01); *A61F 2002/3028* (2013.01); *A61F 2002/30593* (2013.01); *A61F 2002/30803* (2013.01); *A61F 2002/30892* (2013.01); *A61F 2002/4007* (2013.01)

(58) Field of Classification Search
CPC ... A61B 17/1684; A61F 2/4003; A61F 2/4612
See application file for complete search history.

(56) References Cited

U.S. PATENT DOCUMENTS

| | | | | |
|---|---|---|---|---|
| 2,785,673 A | * | 3/1957 | Anderson | A61F 2/3601 623/23.11 |
| 6,322,564 B1 | * | 11/2001 | Surma | A61F 2/4607 606/89 |
| 2008/0183297 A1 | * | 7/2008 | Boileau | A61B 17/1637 623/16.11 |
| 2011/0028977 A1 | * | 2/2011 | Rauscher | A61B 17/1684 606/80 |
| 2011/0125155 A1 | * | 5/2011 | Mutchler | A61B 17/1684 606/87 |

(Continued)

*Primary Examiner* — Nicholas W Woodall
(74) *Attorney, Agent, or Firm* — David Meibos; Maywood IP Law

(57) ABSTRACT

Arthroplasty components include an articular surface and a bone-facing surface. The bone-facing surface includes a concave arrangement of planar surfaces which converge as they approach a middle portion of the articular surface. Instruments and implantation methods are also disclosed.

20 Claims, 66 Drawing Sheets

(56) References Cited

U.S. PATENT DOCUMENTS

2012/0123419 A1* 5/2012 Purdy ................ A61B 17/1615
606/83

* cited by examiner

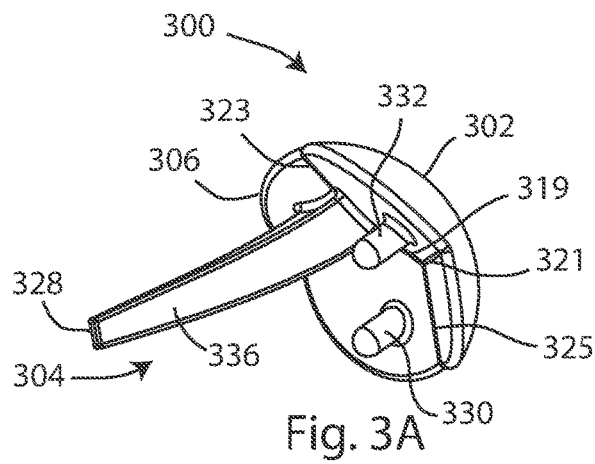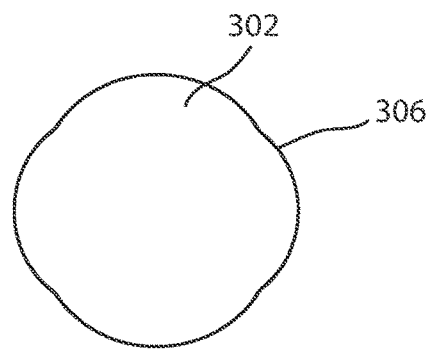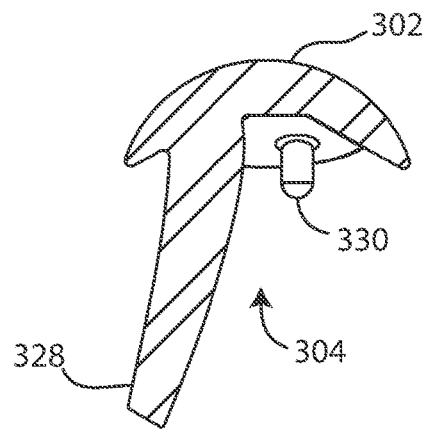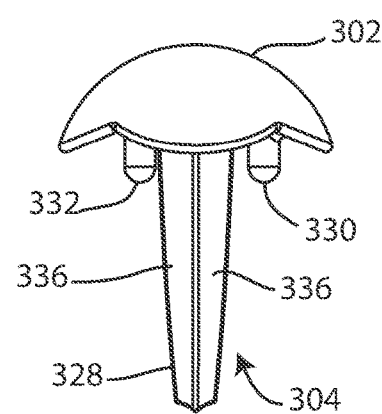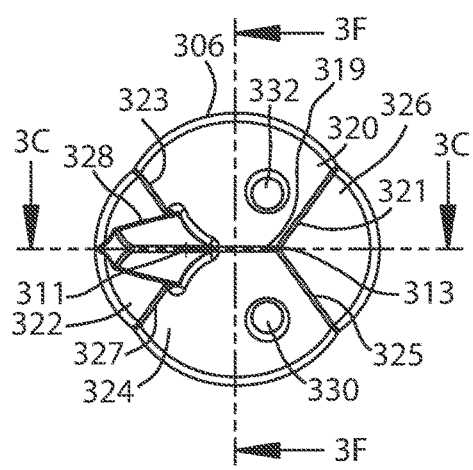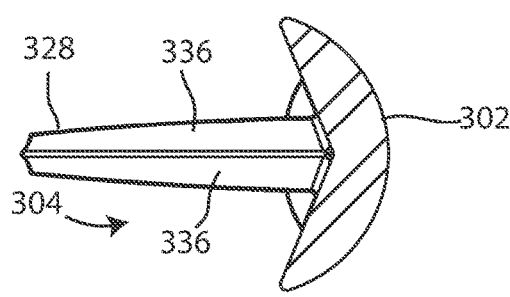

HUMERAL ARTHROPLASTY

CROSS-REFERENCE TO RELATED APPLICATIONS

This application is a continuation of U.S. patent application Ser. No. 16/375,850 filed on Apr. 4, 2019 entitled HUMERAL ARTHROPLASTY, which is a continuation application of U.S. patent application Ser. No. 15/629,182, filed Jun. 21, 2017, entitled HUMERAL ARTHROPLASTY, which issued on Apr. 23, 2019 as U.S. Pat. No. 10,265,185, which is a continuation of U.S. patent application Ser. No. 15/042,601, filed Feb. 12, 2016, entitled HUMERAL ARTHROPLASTY, which issued as U.S. Pat. No. 9,814,587 on Nov. 14, 2017, which is a continuation of U.S. patent application Ser. No. 14/069,154, filed Oct. 31, 2013, entitled HUMERAL ARTHROPLASTY, which issued as U.S. Pat. No. 9,289,306 on Mar. 22, 2016, which claims the benefit of U.S. Provisional Patent Application No. 61/794,348, filed Mar. 15, 2013, entitled HUMERUS PROSTHETIC COMPONENT WITH MULTIPLE CIRCLES OF A SPHERE DESIGN AND ASSOCIATED INSTRUMENTATION. The above-referenced documents are incorporated herein by reference in their entirety.

BACKGROUND

In total shoulder arthroplasty, a glenoid implant is attached to a prepared glenoid or scapula, and a humeral implant is attached to a prepared humerus. The humeral implant usually includes a convex articular surface, at a proximal end thereof which engages and moves relative to a concave articular surface formed in the glenoid implant, although this arrangement is 0.0; sometimes reversed so that the humeral implant includes the convex articular surface and the glenoid implant includes the convex articular surface. The ligaments and muscles of the shoulder surround the implants and maintain the humeral implant against the glenoid implant, while at the osame time allowing relative movement therebetween.

Current anatomic prostheses for the proximal humerus generally fall into two types: stemmed prostheses and resurfacing prostheses.

Stemmed prostheses are quite common. Stemmed prostheses combine a hemispherical head replacement with a stem which extends into the shaft (diaphysis) of the humerus to anchor the prosthesis. Stemmed prostheses often require the removal of the entire hemisphere of humeral head bone, as well as drilling, reaming and/or broaching into the adjacent shaft of the humerus to seat the component. The hemispherical head component and stem are typically solid metal and can be of considerable weight. Stemmed prostheses also frequently require the surgeon to place the humeral head articular bearing surface in a position which is either fixed relative to the shaft of the humerus, or has modular adjustable connection mechanisms allowing partial adjustment between the placement of the hemispherical head component and the stem placed in the shaft of the humerus. This may not always match the actual anatomy of the patient, especially if deformity is present. Although many current prostheses provide for adjustments such as retroversion, offset, or neck-shaft angle, these adjustments are always limited to some degree, or constrained, by the stem to which the prosthetic humeral head is attached.

Resurfacing prostheses have a hollow hemisphere which rests on top of the humeral bone with a solitary peg or post in the humeral head for anchoring stability. Resurfacing prostheses have the advantage of resting directly on top of the bone of the upper humerus and do not have a stem that extends into the shaft of the humerus. Therefore the surgeon is free to place the prosthesis based on each individual patient's anatomy. Resurfacing prostheses also do not require the removal of the entire humeral head bone; simply the upper articular end is reshaped to accept the prosthesis sitting on top. The prosthesis itself acts as a surface cover, and the volume of bone underneath in the hemisphere remains. This preserves more of the patient's bone stock and if revision surgery is needed, allows for a much simpler re-operation because the shaft has not yet been violated.

The preservation of bone in the upper humerus with a resurfacing prosthesis may unfortunately become a disadvantage when the surgeon performs a total shoulder arthroplasty. In this operation, the surgeon also places a prosthesis into the glenoid cavity of the scapula. With the bone of the upper humerus still in the way, access to the glenoid may be very difficult and placing the glenoid prosthesis properly can be challenging.

BRIEF DESCRIPTION OF THE DRAWINGS

While examples of the present technology have been shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

FIG. 3A is an isometric view of yet another humeral component: FIG. 3B is a medial view of the humeral component of FIG. 3A: FIG. 3C is a cross sectional view of the humeral component of FIG. 3A, taken along section line 3C-3C of FIG. 3E; FIG. 3D is a superior view of the humeral component of FIG. 3A; FIG. 3E is a lateral view of the humeral component of FIG. 3A; and FIG. 3F is a cross sectional view of the humeral component of FIG. 3A, taken along section line 3F-3F of FIG. 3E;

DETAILED DESCRIPTION

Figure 1A:
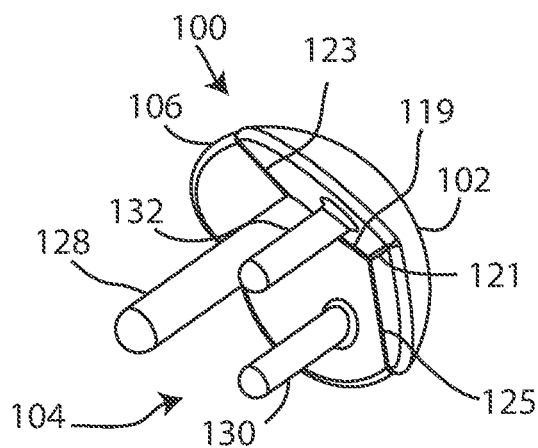
FIG. 1A is an isometric view of a humeral component.
Figure 1B:
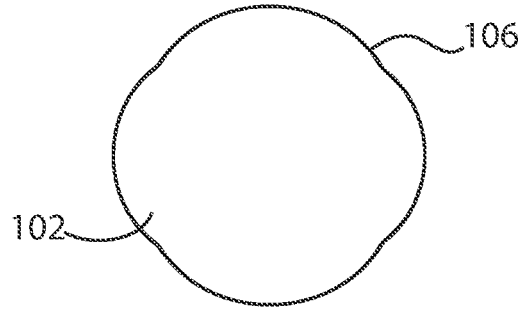
FIG. 1B is a medial view of the humeral component of FIG. 1A.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

One of the objectives of the present technology is to provide a prosthesis for the articular surface of the proximal humerus that allows for a bone preserving and anatomically accurate surgical operation. The disclosed prosthesis requires several small bone cuts to remove a small amount of bone from the upper humerus, but significantly less than a stemmed prosthesis. However the small amount of bone removed may be just enough to allow improved access to a surgeon who also is placing a glenoid prosthesis, especially if the glenoid prosthesis uses an oblique angle of insertion. The disclosed humeral prosthesis still rests on the surface of the upper humerus and does not extend into the humeral shaft, unless the surgeon chooses to use a longer stemmed example.

The disclosed humeral prosthesis can be modified by varying the size, angle and relative location of each individual circle of a sphere relative to the other circles. The prosthesis may be altered in discrete regions to adapt the component precisely to cover or avoid certain surrounding anatomical structures, such as the rotator cuff tendon insertions of the teres minor, infraspinatus, supraspinatus, and subscapularis muscles. This cannot be done with a prosthesis designed as a single hemisphere and having an articular margin which lies on a plane.

Another design, known as a stemless hemiarthroplasty prosthesis, also uses a hemispherical humeral head implant placed on top of the upper humerus after a standard humeral head cut has been made. Though this design does not require the placement of a stem, the solid large metal head is of the same volume and weight as a comparable head used in a stemmed design, but is anchored by a shallow fixation apparatus.

An objective of the present technology is to disclose a prosthesis for the articular surface of the proximal humerus having overlapping circles of a sphere.

Another objective of the present technology is to disclose a prosthesis for the articular surface of the proximal humerus having an ellipsoid shape of the humeral articular surface.

Still another objective of the present technology is to disclose a prosthesis for the articular surface of the proximal humerus having a long stem example of a resurfacing type prosthesis.

Another objective of the present technology is to disclose a cutting guide instrument used to prepare the bone to seat the humerus prosthesis.

Advantages of the present technology include the multiple joined circle-of-a-sphere design, which requires less removal of bone than a standard hemiarthroplasty. Due to significantly reduced volume, the metal humeral component weighs significantly less than a standard hemispherical humeral component of corresponding size, but provides nearly equal surface area coverage of the proximal humeral articular surface. The reduced weight of the humeral component may improve shoulder kinematics. The reduced weight of the humeral component may also contribute to improved long-term stability by reducing loosening forces placed on the anchoring elements. Reduced volume of metal may also potentially reduce material costs of manufacturing the implant.

The humeral canal is not violated during the surgical procedures disclosed herein, reducing blood loss and marrow-fat emboli release into the blood. The canal is also preserved for future stemmed arthroplasty components if revision surgery is ever required. This does not apply in the case of the long stem example.

The undersurface design resulting from overlapping planar bone cuts provides resistance to rotational forces and is potentially more stable than a single flat cut. This may provide for improved long-term stability of the component. By making multiple oblique cuts through the humeral head surface, a greater proportion of the component will be resting again the strong outer cortical bone of the humerus than a standard hemispherical prosthesis.

The present design does not require or reference the humeral canal to determine proper location for bone cuts, thus the surgeon is free to position the humeral component to best fit each patient's' individual anatomy. This is even more important in cases where deformity has altered the normal shape of the humerus.

The articular surface of the humeral prosthesis can be ellipsoid to better match the normal anatomy of the humerus. Current stemmed and resurfacing arthroplasty designs, due to the variable-offset feature of stemmed designs and the bone preparation process of resurfacing designs, include only spherical humeral heads.

The most inferior circle of the prosthesis extends inferiorly to cover the most medial aspect of the medial humeral neck bone, in order to reduce the incidence of impingement of the medial humerus against a glenoid prosthetic component. Retrieval studies of failed glenoid components have shown that inferior impingement is a significant contributor to glenoid loosening.

By placing the prosthesis more precisely in a location that better replicates the normal anatomy, motion across the glenohumeral joint may be more smooth and stable, and eccentric forces placed upon the glenoid prosthesis may be reduced.

The current prosthesis can be finely adjusted by varying the size, angle and relative location of each individual circle of a sphere relative to the other circles. This allows the prosthesis to be altered in discrete regions for clinical purposes.

Other objectives and advantages of this technology will become apparent from the following description taken in conjunction with the accompanying drawings wherein are set forth, by way of illustration and example, certain embodiments of the technology. The drawings contained herein constitute a part of this specification and include exemplary embodiments of the present technology and illustrate various objects and features thereof.

Referring to FIGS. 1A-1F, a humeral component 100 includes an articular surface 102 and a bone-facing side 104 which is opposite to the articular surface.

The humeral component 100 has a smooth, polished articular bearing surface 102 which may articulate with a natural glenoid socket or a glenoid prosthetic component. The glenoid prosthetic component may be of the type disclosed in U.S. Provisional Patent Application No. 61/776,398, filed Mar. 11, 2013, and entitled OBLIQUE-INSERTION ANCHORING MECHANISM FOR GLENOID PROSTHETIC COMPONENT; or the type disclosed in U.S. patent application Ser. No. 14/042,258, filed Sep. 30, 2013, and entitled GLENOID ARTHROPLASTY. The contents of these documents are incorporated herein by reference. The glenoid component may be polyethylene or another biocompatible material.

The prosthetic humeral component may be designed as multiple overlapping circles of a sphere, where the sphere forms the articular surface 102. A "circle of a sphere" is a circle defined by the intersection of a sphere and a plane. If the plane contains the center of the sphere, then the circle is called a "great circle"; otherwise, it is a "small circle." A "spherical cap" is a three-dimensional portion of a sphere cut off by an intersecting plane. If the plane passes through the center of the sphere, the spherical cap is called a "hemisphere." If the height of the spherical cap is less than the radius of the sphere, the spherical cap is called a "minor spherical cap." If the height of the spherical cap is greater than the radius of the sphere, the spherical cap is called a "major spherical cap." In this specification, any reference to a circle of a sphere is also a reference to the corresponding spherical cap, and any reference to a spherical cap is also a reference to the corresponding circle of the sphere.

Together these overlapping circles of a sphere, and corresponding spherical caps, form an articular surface which is nearly hemispherical, or partly spherical, hut with significantly less volume of material than a solid hemisphere due to the multiple planar surfaces on the bone facing side 104, which in a solid hemisphere would be flat. The articular surface area created by the overlapping circles of a sphere nearly covers the native articular surface of the proximal humerus. Referring to FIG. 1A, each one of the planar surfaces corresponds to one of the overlapping circles of a sphere or spherical caps. All of the spherical surfaces are co-radial; they share the same spherical center and all spherical radii are equal, so that the articular surface 102 is an uninterrupted spherical surface. Some examples of the present technology utilize four overlapping circles of a sphere, but other examples may have three, five or more overlapping circles of a sphere.

Figure 1C:
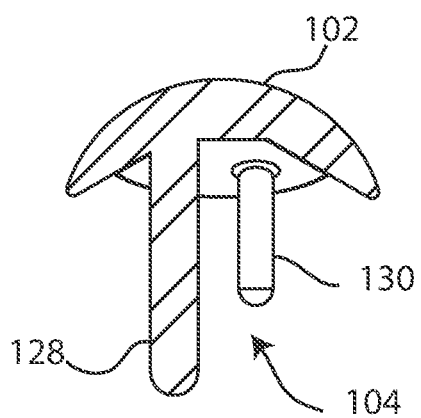
FIG. 1C is a cross sectional view of the humeral component of FIG. 1A, taken along section line 1C-1C of FIG. 1E.
Figure 1D:
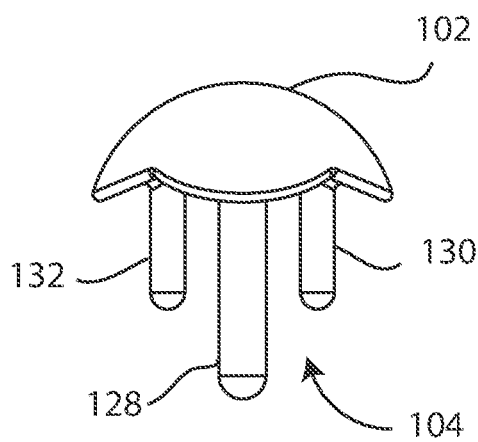
FIG. 1D is a superior view of the humeral component of FIG. 1A.
Figure 1E:
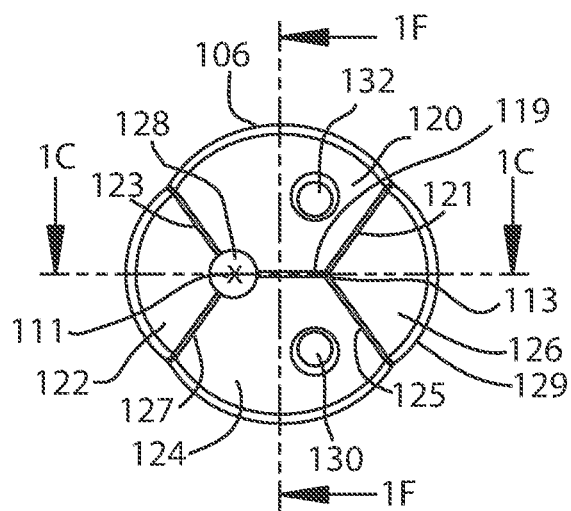
FIG. 1E is a lateral view of the humeral component of FIG. 1A.
Figure 1F:
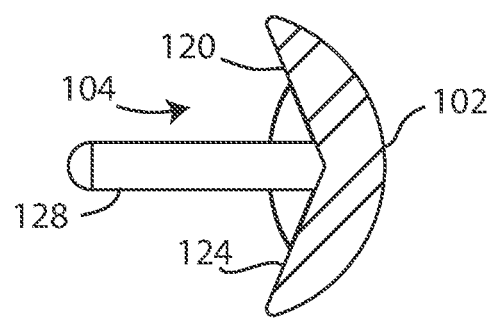
FIG. 1F is a cross sectional view of the humeral component of FIG. 1A, taken along section line 1F-1F of FIG. 1E.
Figure 2A:
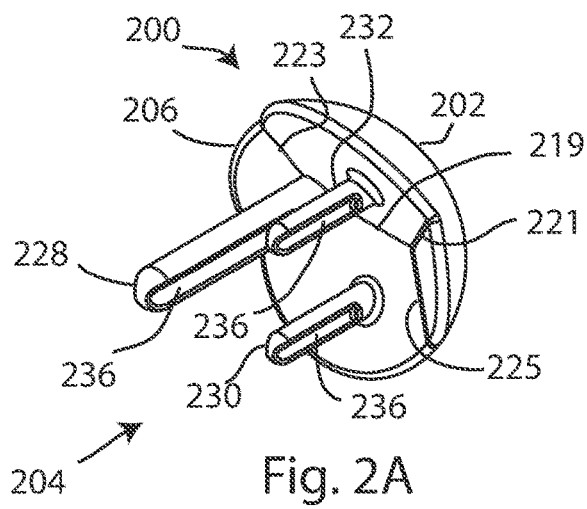
FIG. 2A is an isometric view of another humeral component.
Figure 2B:
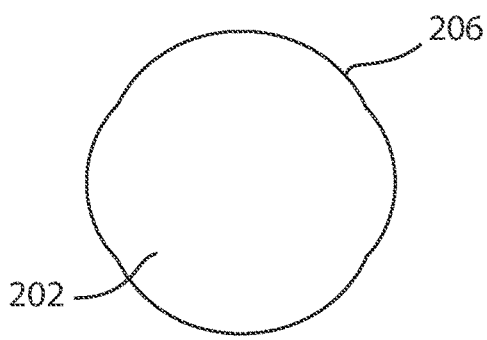
FIG. 2B is a medial view of the humeral component of FIG. 2A.
Figure 2C:
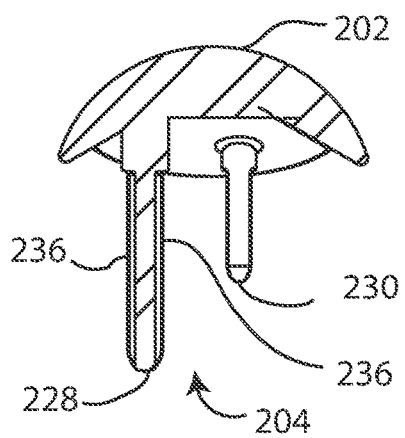
FIG. 2C is a cross sectional view of the humeral component of FIG. 2A, taken along section line 2C-2C of FIG. 2E.
Figure 2D:
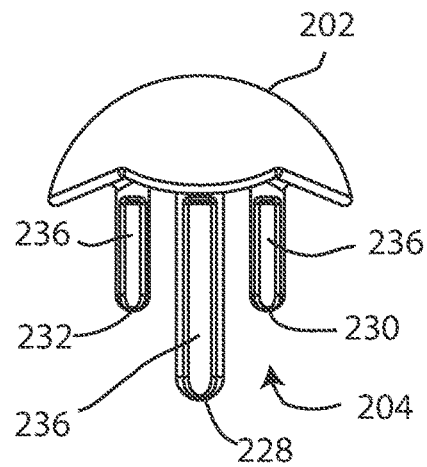
FIG. 2D is a superior view of the humeral component of FIG. 2A.
Figure 2E:
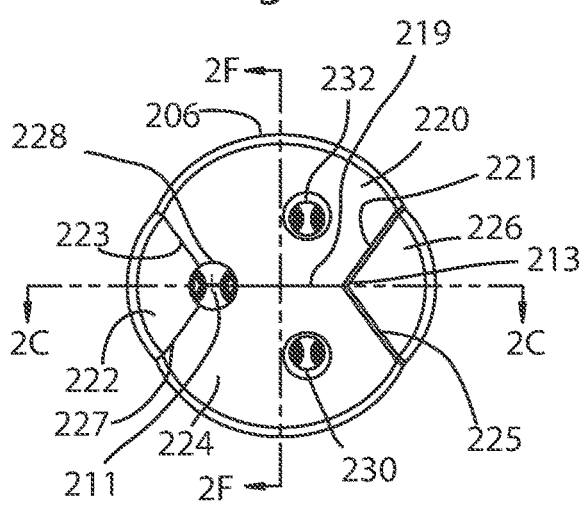
FIG. 2E is a lateral view of the humeral component of FIG. 2A.
Figure 2F:
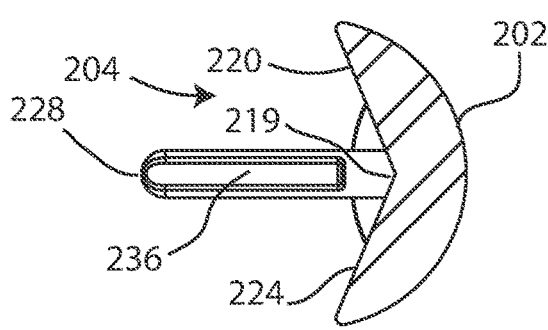
FIG. 2F is a cross sectional view of the humeral component of FIG. 2A, taken along section line 2F-2F of FIG. 2E.

In an alternate version of the technology, the prosthetic humeral component 100 may have an ellipsoid or ovoid articular surface 102, rather than a spherical articular surface. The circles of an ellipsoid or ovoid, and the corresponding caps, may be overlapped to create the same effect of covering a similar amount of surface area with a reduced volume of material. The ellipsoid or ovoid articular surface has a first radius (or first diameter) in a first plane or along a first axis which is dimensionally different from a second radius (or second diameter) in a second plane or along a second axis. The first radius may be larger or smaller than the second radius. Referring to FIGS. 1C, 1E, and 1F, the radius of articular surface 102 in FIG. 1C may be dimensionally different from the radius of articular surface 102 in FIG. 1F when the articular surface 102 is ellipsoid or ovoid instead of spherical. For example, an ellipsoid or ovoid articular surface may have a larger diameter along the superior-inferior axis in the coronal plane than in the transverse plane, or vice versa. The increased radius of curvature of an ellipsoid or ovoid bearing surface in a given direction may reduce the constraint of the humeral head within the glenohumeral joint in that direction. This reduced constraint may result in reduced eccentric forces applied to the bearing surface and reduced risk of implant loosening. The increased radius of curvature may be oriented relative to the prevailing direction of articulation of a given joint, or relative to an articulation direction in which impingement, loosening, or other stress-related effects are known to occur. These ellipsoid or ovoid shapes may also be narrower at the superior end and broader at the inferior end. The ellipsoid or ovoid shape may better replicate the normal articular surface of the humeral head, better replicating the kinematics of the shoulder during articulation, and better matching the morphology of the natural articulating surface, allowing for better fit and transition between the implant and the bone, at least in some patients.

Humeral components according to the present technology may also be designed as a hemisphere, spherical cap, ellipsoid cap, or ovoid cap with a tapered polygonal socket forming the bone-facing side. The tapered polygonal socket may be designed by extruding a polygonal shape from the flat side of the hemisphere or cap toward the articular surface while tapering the sides of the polygonal shape inward. The polygonal shape may be a triangle, square, rectangle, pentagon, or other polygonal shape, and may be regular or irregular, and may be symmetrically or asymmetrically disposed relative to the center of the hemisphere or cap. The sides of the polygonal shape may all have the same taper angle, although one or more sides may have a different taper angle. It can be appreciated that the bone-facing side 104 of humeral component 100 may be designed as a tapered rectangular socket, and similarly for humeral components 200, 300, 400, 500, 600 discussed below.

Humeral component 100 may include four planar surfaces 120, 122, 124, 126 in a concave arrangement in which the planar surfaces converge together as they approach the middle of the articular surface 102, as seen best in FIG. 1A. Other examples may include three, five, or more planar surfaces in a concave arrangement. More specifically, one example may include planar surfaces 120, 122, 124. The planar surfaces diverge as they extend away from the middle of the articular surface 102, and intersect the articular surface to establish an articular margin 106 around a perimeter of the humeral component 100. The articular margin may be described as scalloped or having one or more indentations 129. Each one of the planar surfaces intersects each other planar surface at an obtuse angle, although right angles and acute angles are also contemplated. Planar surfaces 120, 124 intersect along a line 119, planar surfaces 120, 126 intersect along a line 121, planar surfaces 120, 122 intersect along a line 123, planar surfaces 124, 126 intersect along a line 125, and planar surfaces 124, 122 intersect along a line 127. The lines 119, 121, 123, 125, 127 may also be referred to as intersections, edges, or internal corners, and may include fillet radii, as best seen in FIG. 1E. Referring to FIG. 1E, lines 119, 123, 127 intersect at a first point 111; and lines 119, 121, 125 intersect at a second point 113. Lines 123, 121 and 127, 125 also intersect when extended. Line 119 in this example may extend in a superior-inferior direction when the humeral component 100 is implanted.

The humeral component 100 may have a roughened or porous bone-facing side 104, or undersurface, which rests on the prepared bone of the humerus when the humeral component is implanted. These roughened or porous surfaces assist in bony apposition between the implant and the underlying subcondylar bone encouraging bony ingrowth into the porosity of the bone-facing side once the humeral component is implanted. From this undersurface or bone-facing side 104, at least one anchoring element 128 projects outwardly; the example shown includes three anchoring elements 128, 130, 132. The anchoring elements project into the humeral bone when the humeral component is implanted, and may anchor the humeral component to prevent loosening or micromotion. The anchoring elements may be pegs which are round, cruciate, or have fins, or have another cross sectional shape for bone fixation. The anchoring elements may include fenestrations. Some of the examples disclosed herein utilize three pegs, but the number of pegs may vary. The pegs may be parallel, converging, diverging, or skew. The pegs may be smooth, matte, rough, or porous to promote bone cement fixation or bone ingrowth. The illustrated anchoring elements 128, 130, 132 are cylindrical and parallel to one another. Anchoring element 128 is longer than anchoring elements 130, 132, and may therefore be suited for implantation in an inferior aspect of the humeral head/neck.

Humeral component 100 is bilaterally symmetric about a plane through line 119, and may therefore be implanted in right or left shoulders. Humeral component 100 may be implanted so that planar surface 126 covers a superior aspect of the humeral head, planar surface 122 covers an inferior aspect of the humeral head, planar surfaces 120 and 124 cover anterior and posterior portions of the humeral head, anchoring element 128 extends through the inferior aspect of the humeral head and optionally into the humeral neck, and anchoring elements 130, 132 extend into anterior and posterior portions of the humeral head. The outer portion, or rim, of planar surface 126 faces at least a portion of the rotator cuff, and, because planar surface 126 is indented to form the indentation 129 along the articular margin 106, a space exists between the rim of planar surface 126 and the rotator cuff. This space provides relief, or room, for the rotator cuff to function without excessive rubbing against the outer portion, or rim, of the humeral component 100, thus reducing the risk of rotator cuff damage.

In one example, the inferior-most peg may be curved and elongated, forming a stem which extends distally into the diaphysis of the humerus, following the curve of the medial neck of the humerus. This inferior peg or stem may be manufactured as one piece with the bearing surface component, or the peg or stem may be modular, supplied in varying thickness and lengths. A modular peg may be attached to the bearing portion of the component via a Morse taper, screw-in or other connection mechanism.

In another embodiment, the location of the pegs on the backside of the prosthetic component may project in a more vertical direction. This embodiment may be suitable for a surgeon utilizing a subscapularis-preserving surgical technique where the only exposure to the humerus is from the superior direction.

The prosthesis may be fixed in place with bone cement, or it may have a roughened surface or porous coating on the undersurface for cementless (press-fit) use.

The entire humeral component 100 may be made of a solid metal piece. In other examples, the prosthesis may be made of another material, such as any of the materials commonly used in orthopaedic joint arthroplasty, such as ceramic, composite, polyethylene or pyrocarbon. Combinations of materials may also be used.

Referring to FIGS. 2A-2F, another humeral component 200 includes an articular surface 202 and a bone-facing side 204 which is opposite to the articular surface. Humeral component 200 includes the following features, which may be substantially similar to, or the same as, the corresponding features of humeral component 100: planar surfaces 220, 222, 224, 226; lines 219, 221, 223, 225, 227; points 211, 213; and anchoring elements 228, 230, 232. In an alternate version of the technology, the prosthetic humeral component 200 may have an ellipsoid or ovoid articular surface 202, rather than a spherical articular surface. The planar surfaces 220, 222, 224, 226 are in a concave arrangement in which the planar surfaces converge together as they approach the middle of the articular surface 202, as seen best in FIG. 2A. Each one of the planar surfaces intersects each other planar surface at an obtuse angle, although right angles and acute angles are also contemplated. Fillet radii are present along lines 221, 225 and absent along lines 219, 223, 227. The illustrated anchoring elements 228, 230, 232 are cylindrical and parallel to one another. These anchoring elements include bilateral longitudinal grooves 236. Anchoring element 228 is longer than anchoring elements 230, 232, and may therefore be suited for implantation in an inferior aspect of the humeral head/neck.

Humeral component 200 is bilaterally symmetric about a plane through line 219, and may therefore be implanted in right or left shoulders. Humeral component 200 may be implanted so that planar surface 226 covers a superior aspect of the humeral head, planar surface 222 covers an inferior aspect of the humeral head, planar surfaces 220 and 224 cover anterior and posterior portions of the humeral head, anchoring element 228 extends through the inferior aspect of the humeral head and optionally into the humeral neck, and anchoring elements 230, 232 extend into anterior and posterior portions of the humeral head.

Referring to FIGS. 3A-3F, yet another humeral component 300 includes an articular surface 302 and a bone-facing side 304 which is opposite to the articular surface. Humeral component 300 includes the following features, which may be substantially similar to, or the same as, the corresponding features of humeral component 100: planar surfaces 320, 322, 324, 326; lines 319, 321, 323, 325, 327; fillet radii; points 311, 313; and anchoring elements 328, 330, 332. In an alternate version of the technology, the prosthetic humeral component 300 may have an ellipsoid or ovoid articular surface 302, rather than a spherical articular surface. The planar surfaces 320, 322, 324, 326 are in a concave arrangement in which the planar surfaces converge together as they approach the middle of the articular surface 302, as seen best in FIG. 3A. Each one of the planar surfaces intersects each other planar surface at an obtuse angle, although right angles and acute angles are also contemplated. The illustrated anchoring elements 330, 332 are cylindrical and parallel to one another. Anchoring element 328 is curved outwardly, and is longer than anchoring elements 330, 332, and may therefore be suited for implantation in an inferior aspect of the humeral head/neck. Anchoring element 328 also includes four longitudinal grooves 336, which are evenly arranged around anchoring element 328. Anchoring element 328 may be described as having a diamond-shaped or star-shaped cross section.

Humeral component 300 is bilaterally symmetric about a plane through line 319, and may therefore be implanted in right or left shoulders. Humeral component 300 may be implanted so that planar surface 326 covers a superior aspect of the humeral head, planar surface 322 covers an inferior aspect of the humeral head, planar surfaces 320 and 324 cover anterior and posterior portions of the humeral head, anchoring element 328 extends through the inferior aspect of the humeral head and optionally into the humeral neck, and anchoring elements 330, 332 extend into anterior and posterior portions of the humeral head.

Figure 4A:
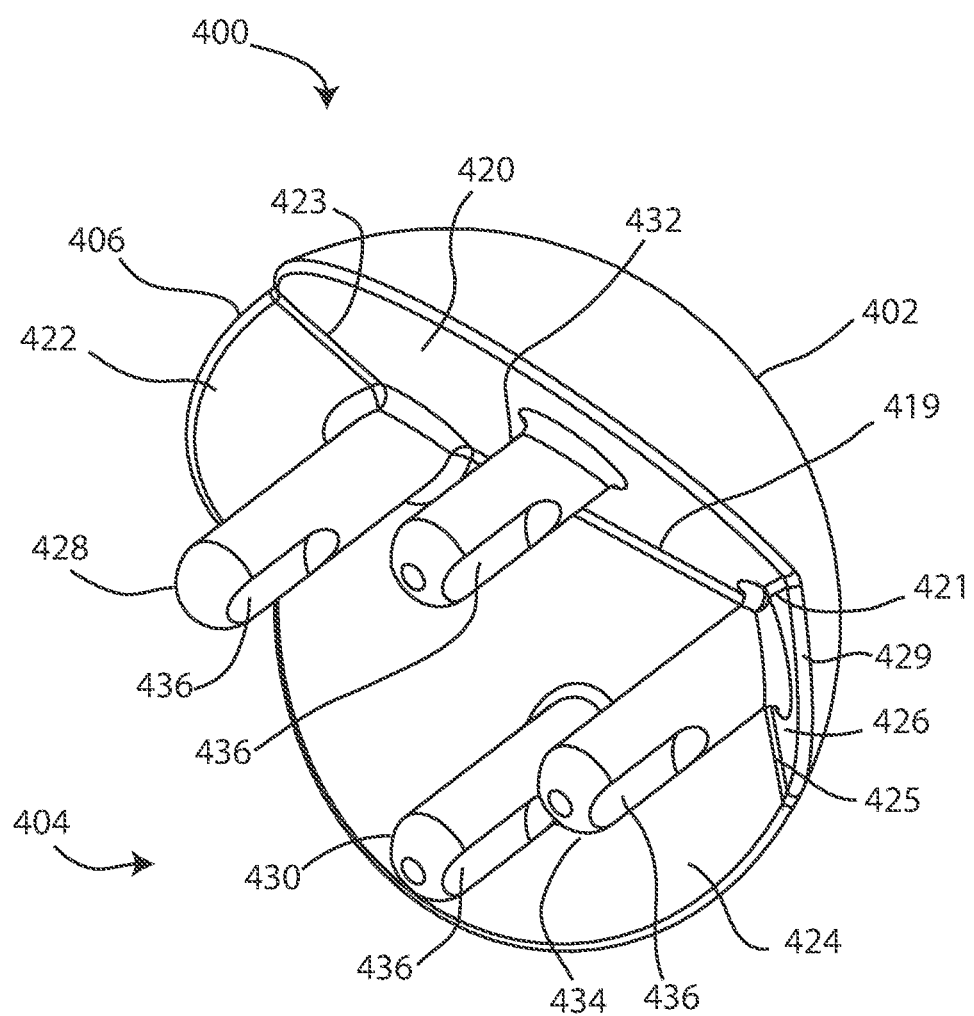
FIG. 4A is an isometric view of yet another humeral component.
Figure 4B:
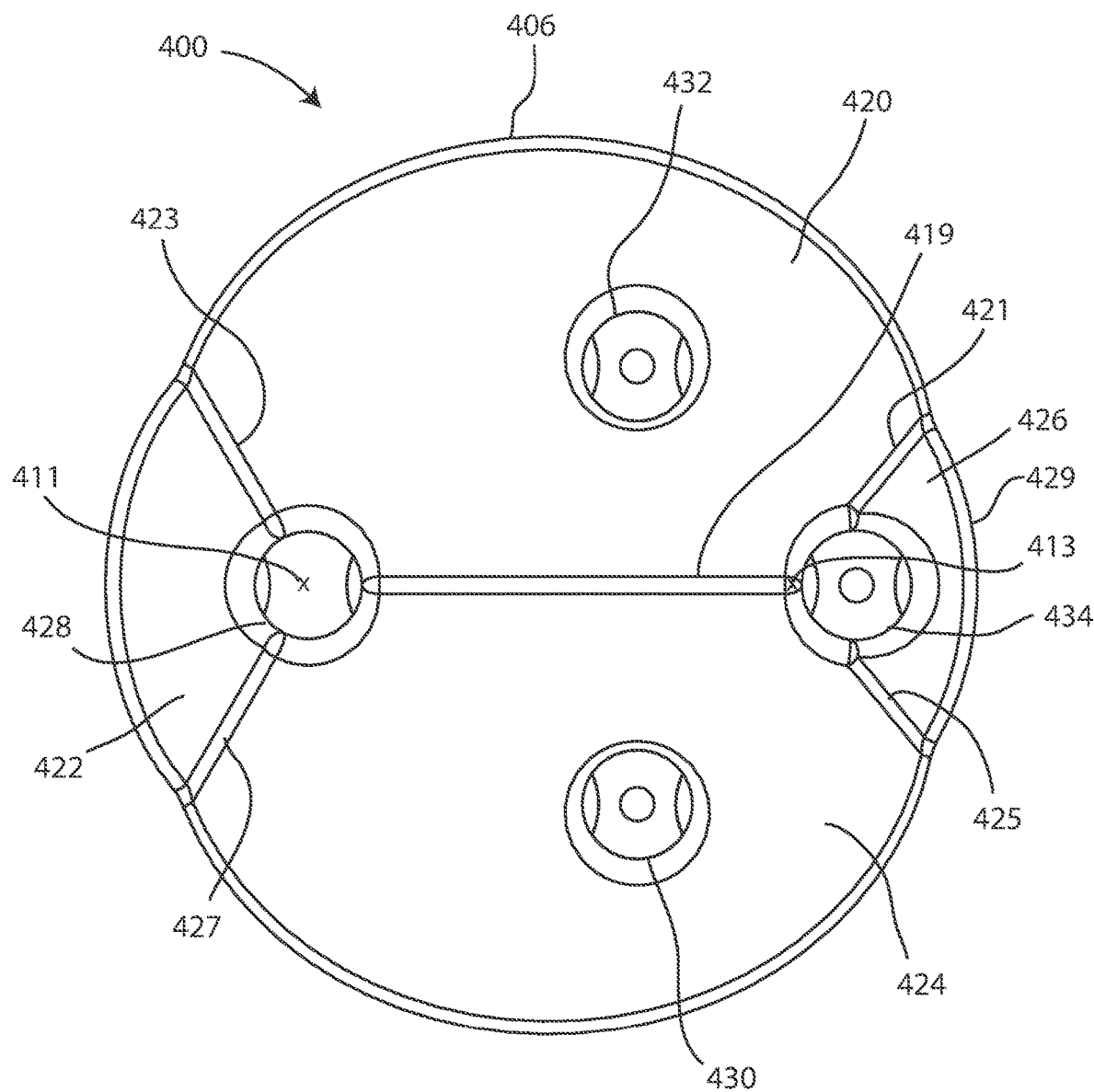
FIG. 4B is a lateral view of the humeral component of FIG. 4A.

Referring to FIGS. 4A-4B, yet another humeral component 400 includes an articular surface 402 and a bone-facing side 404 which is opposite to the articular surface. Humeral component 400 includes the following features, which may be substantially similar to, or the same as, the corresponding features of humeral component 100: planar surfaces 420, 422, 424, 426; lines 419, 421, 423, 425, 427; fillet radii; points 411, 413; and anchoring elements 428, 430, 432. In an alternate version of the technology, the prosthetic humeral component 400 may have an ellipsoid or ovoid articular surface 402, rather than a spherical articular surface. The planar surfaces 420, 422, 424, 426 are in a concave arrangement in which the planar surfaces converge together as they approach the middle of the articular surface 402, as seen best in FIG. 4A. The planar surfaces diverge as they extend away from the middle of the articular surface 402, and intersect the articular surface to establish an articular margin 406 around a perimeter of the humeral component 400. The articular margin may be described as scalloped or having one or more indentations 429. Each one of the planar surfaces intersects each other planar surface at an obtuse angle, although right angles and acute angles are also contemplated. Planar surface 426 has a smaller area than planar surface 422, and may be described as being indented, or centrally offset, particularly in comparison to planar surface 422. Humeral component 400 includes a fourth anchoring element 434. The illustrated anchoring elements 428, 430, 432, 434 are cylindrical and parallel to one another. Anchoring elements 428, 430, 432, 434 also include bilateral longitudinal grooves 436.

Humeral component 400 is bilaterally symmetric about a plane through line 419, and may therefore be implanted in right or left shoulders. Humeral component 400 may be implanted so that planar surface 426 covers a superior aspect of the humeral head, planar surface 422 covers an inferior aspect of the humeral head, planar surfaces 420 and 424 cover anterior and posterior portions of the humeral head, anchoring element 428 extends through the inferior aspect of the humeral head and optionally into the humeral neck, anchoring elements 430, 432 extend into anterior and posterior portions of the humeral head, and anchoring element 434 extends into the superior aspect of the humeral head. The outer portion, or rim, of planar surface 426 faces at least a portion of the rotator cuff, and, because planar surface 426 is indented to form the indentation 429 along the articular margin 406, a space exists between the rim of planar surface 426 and the rotator cuff. This space provides relief, or room, for the rotator cuff to function without excessively rubbing against the outer portion, or rim, of the humeral component 600, thus reducing the risk of rotator cuff damage.

Figure 5A:
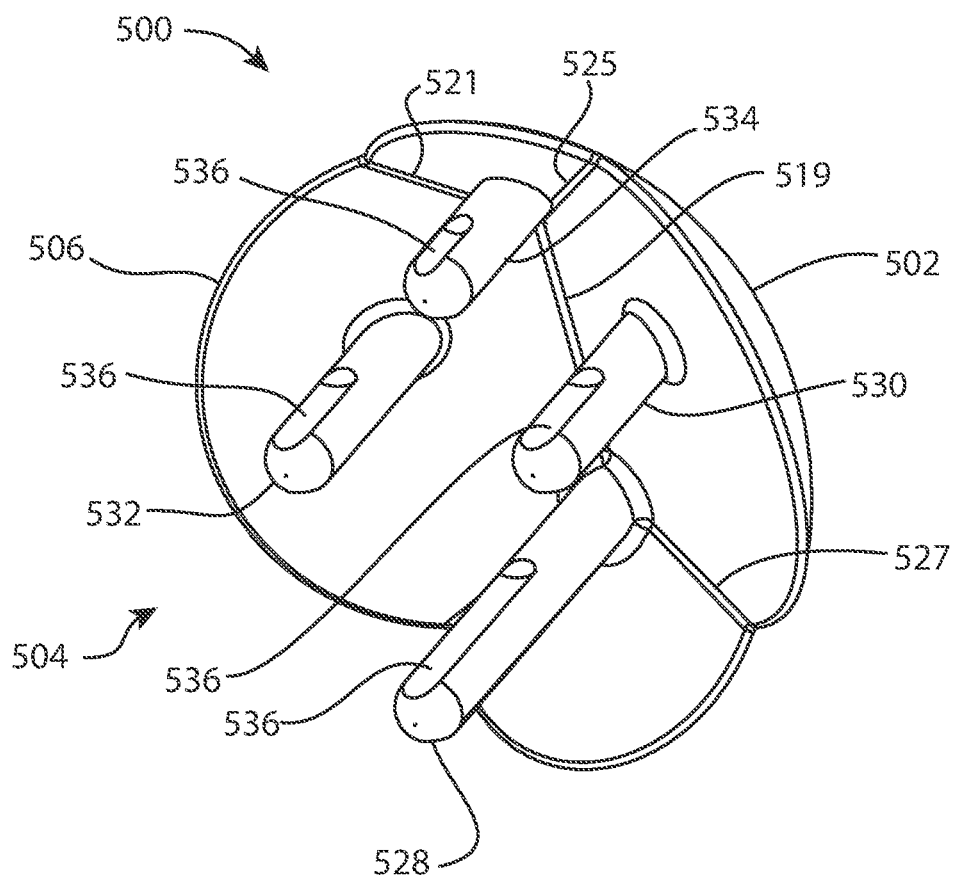
FIG. 5A is an isometric view of yet another humeral component.
Figure 5B:
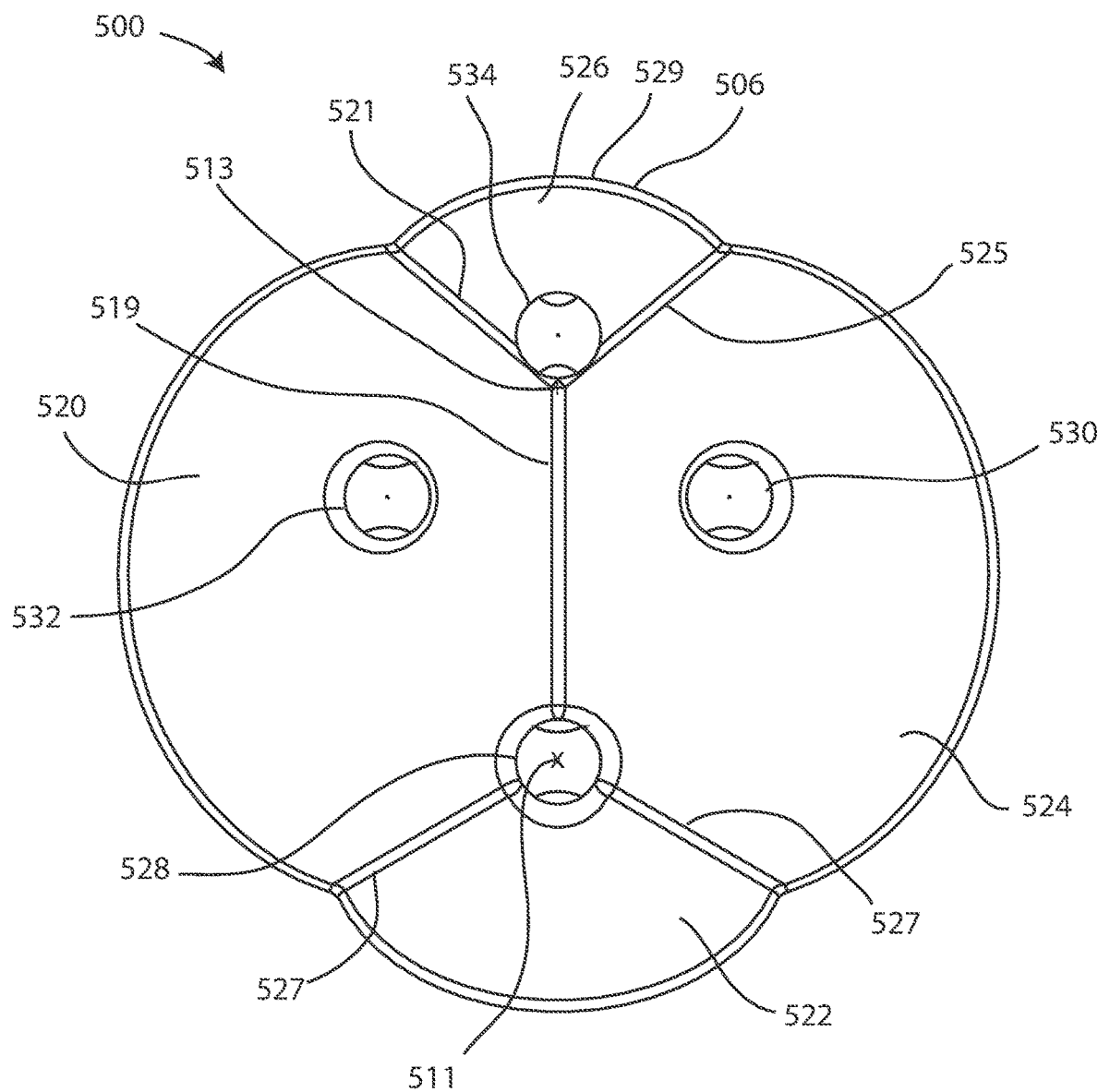
FIG. 5B is a lateral view of the humeral component of FIG. 5A.

Referring to FIGS. 5A-5B, yet another humeral component 500 includes an articular surface 502 and a bone-facing side 504 which is opposite to the articular surface. Humeral component 500 includes the following features, which may be substantially similar to, or the same as, the corresponding features of humeral component 100: planar surfaces 520, 522,524, 526; lines 519, 521, 523, 525, 527; fillet radii; points 511, 513; and anchoring elements 528, 530, 532. In an alternate version of the technology, the prosthetic humeral component 500 may have an ellipsoid or ovoid articular surface 502, rather than a spherical articular surface. The planar surfaces 520, 522, 524, 526 arc in a concave arrangement in which the planar surfaces converge together as they approach the middle of the articular surface 502, as seen best in FIG. 5A. The planar surfaces diverge as they extend away from the middle of the articular surface 502, and intersect the articular surface to establish an articular margin 506 around a perimeter of the humeral component 500. The articular margin may be described as scalloped or having one or more indentations 529. Each one of the planar surfaces intersects each other planar surface at an obtuse angle, although right angles and acute angles are also contemplated. Planar surface 526 has a smaller area than planar surface 522, and may be described as being indented, or centrally offset, particularly in comparison to planar surface 522. Humeral component 500 includes a fourth anchoring element 534. The illustrated anchoring elements 528, 530, 532, 534 are cylindrical and parallel to one another. Anchoring element 528 may be longer than anchoring elements 530, 532, 534. Anchoring elements 528, 530, 532, 534 also include bilateral longitudinal grooves 536.

Humeral component 500 is bilaterally symmetric about a plane through line 519, and may therefore be implanted in right or left shoulders. Humeral component 500 may be implanted so that planar surface 526 covers a superior aspect of the humeral head, planar surface 522 covers an inferior aspect of the humeral head, planar surfaces 520 and 524 cover anterior and posterior portions of the humeral head, anchoring element 528 extends through the inferior aspect of the humeral head and optionally into the humeral neck, anchoring elements 530, 532 extend into anterior and posterior portions of the humeral head, and anchoring element 534 extends into the superior aspect of the humeral head. The outer portion, or rim, of planar surface 526 faces at least a portion of the rotator cuff, and, because planar surface 526 is indented to form the indentation 529 along the articular margin 506, a space exists between the rim of planar surface 526 and the rotator cuff. This space provides relief, or room, for the rotator cuff to function, thus reducing the risk of rotator cuff damage.

Figure 6A:
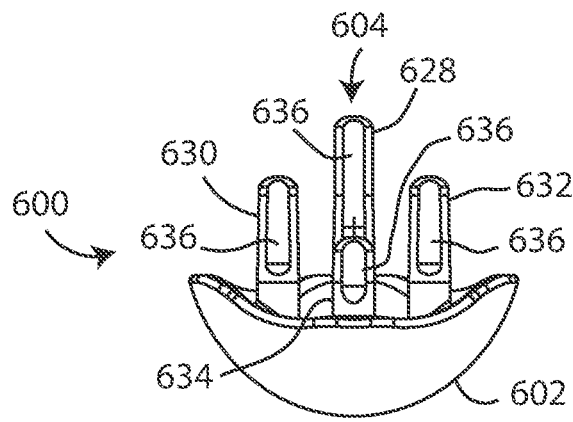
FIG. 6A is a superior view of yet another humeral component.
Figure 6B:
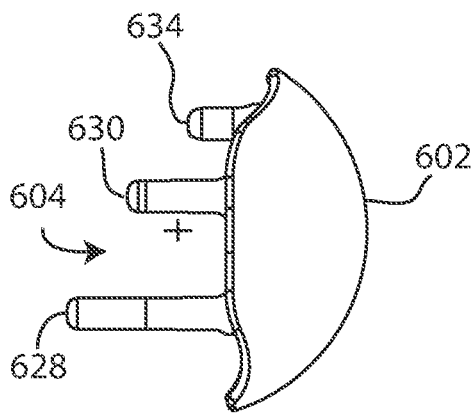
FIG. 6B is an anterior view of the humeral component of FIG. 6A.
Figure 6C:
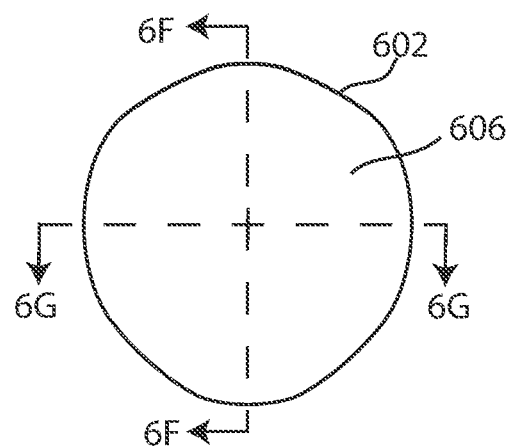
FIG. 6C is a medial view of the humeral component of FIG. 6A.
Figure 6D:
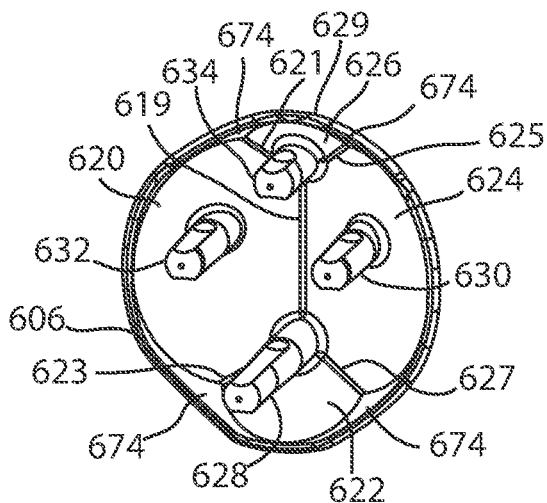
FIG. 6D is an isometric view of the humeral component of FIG. 6A.
Figure 6E:
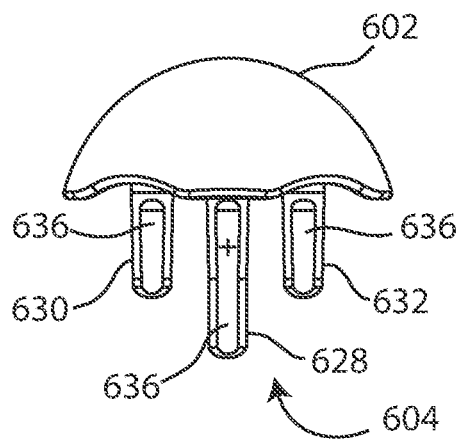
FIG. 6E is an inferior view of the humeral component of FIG. 6A.
Figure 6F:
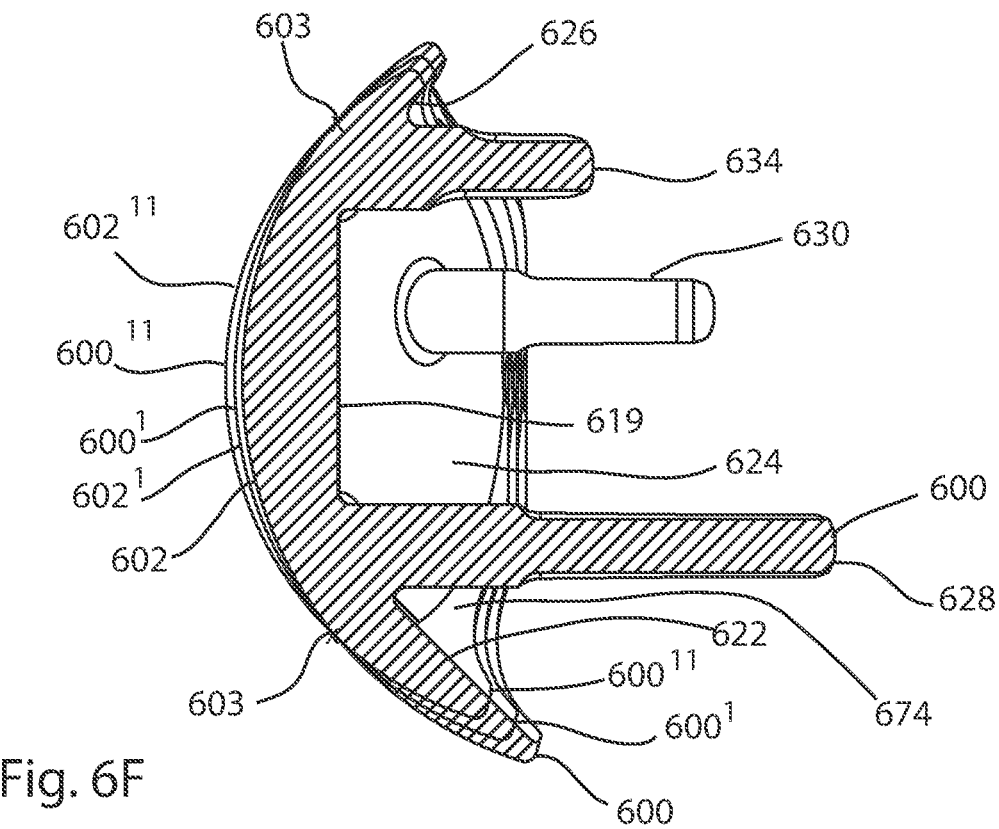
FIG. 6F is a cross sectional view of the humeral component of FIG. 6A, taken along section line 6F-6F of FIG. 6C, with superimposed cross sectional profiles of two other size humeral components.
Figure 6G:
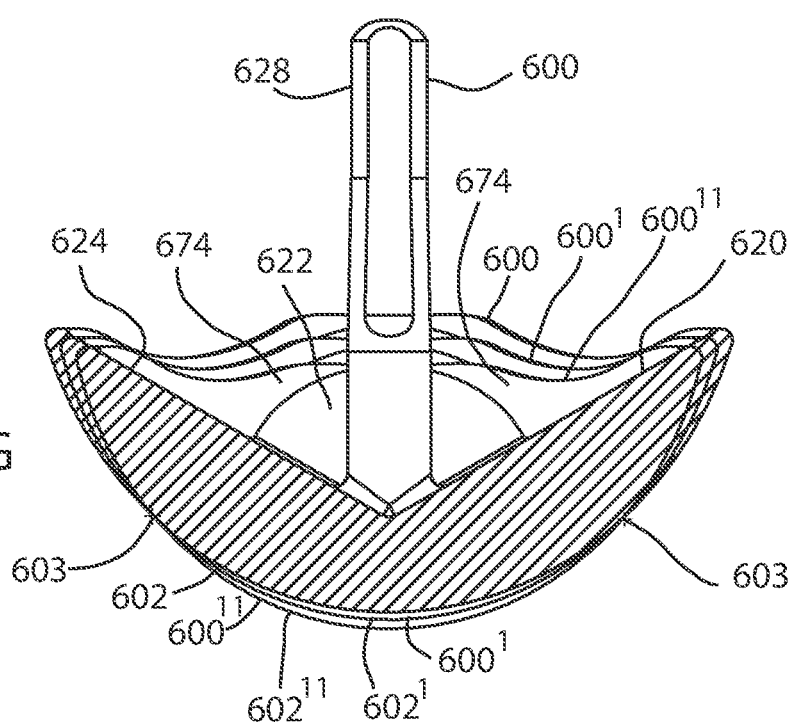
FIG. 6G is a cross sectional view of the humeral component of FIG. 6A, taken along section line 6G-6G of FIG. 6C, with superimposed cross sectional profiles of two other size humeral components.
Figure 6H:
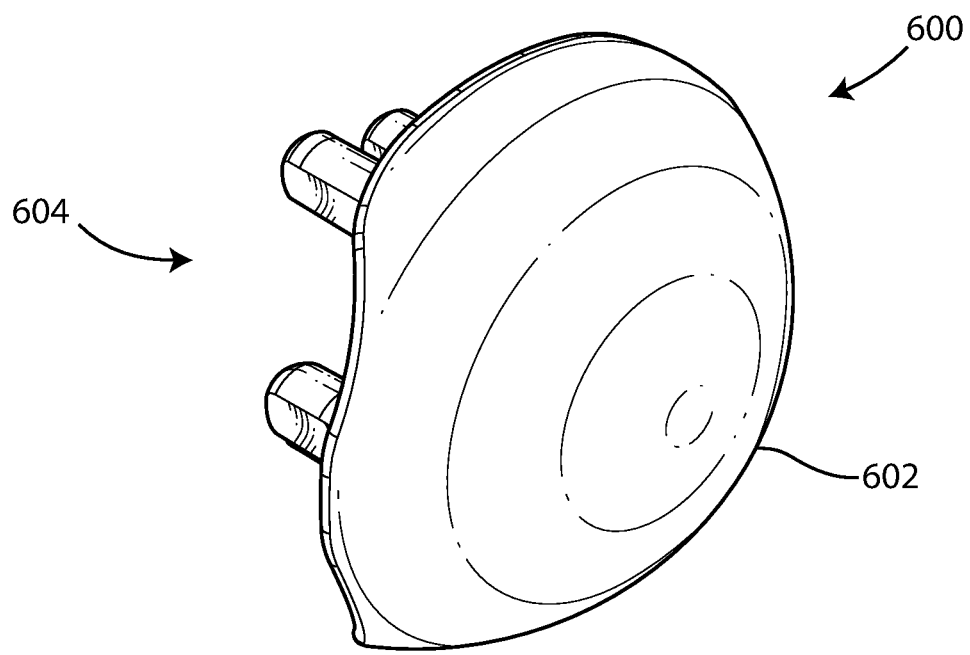
FIG. 6H is a front left perspective view of the humeral component of FIG. 6A.
Figure 6I:
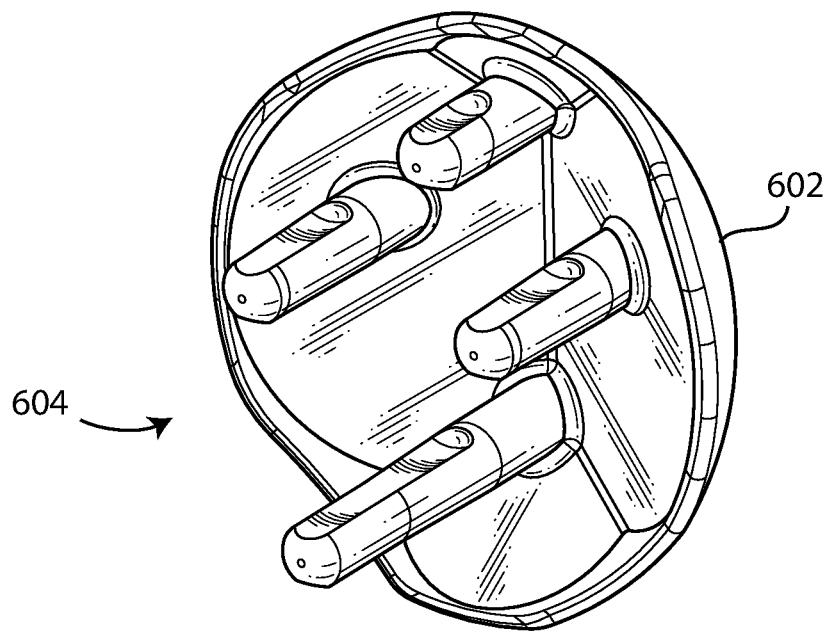
FIG. 6I is a back left perspective view of the humeral component of FIG. 6A.
Figure 6J:
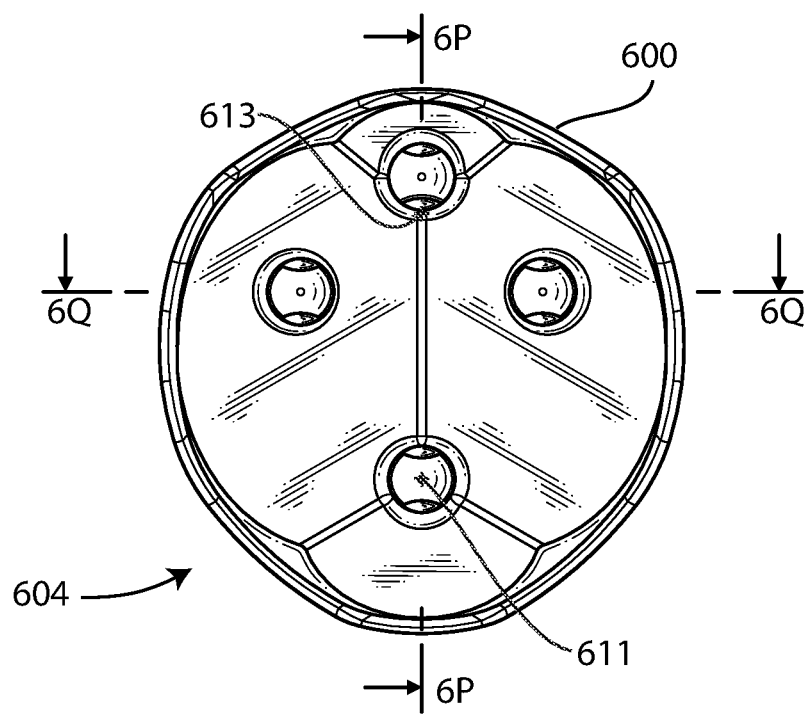
FIG. 6J is a back view of the humeral component of FIG. 6A.
Figure 6K:
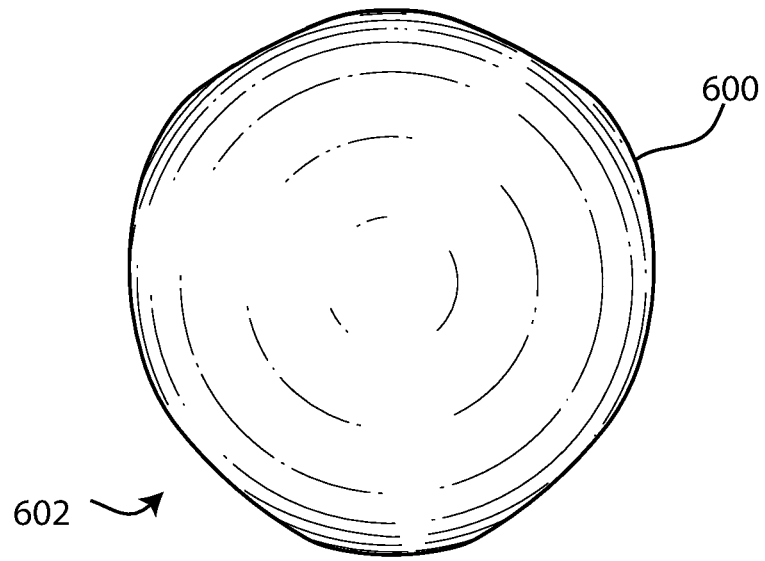
FIG. 6K is a front view of the humeral component of FIG. 6A.
Figure 6L:
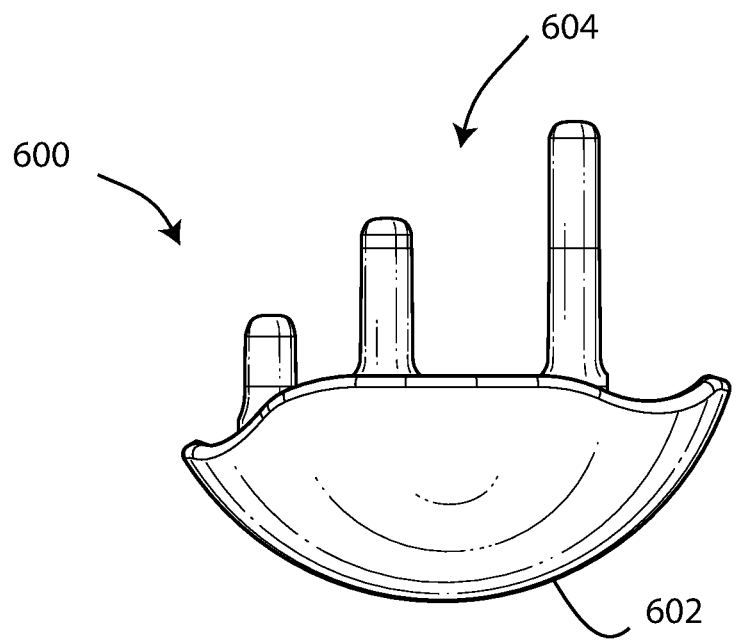
FIG. 6L is a right side view of the humeral component of FIG. 6A.
Figure 6M:
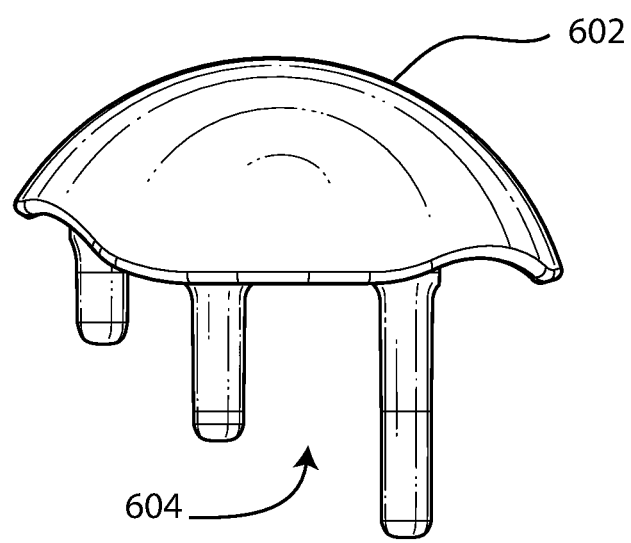
FIG. 6M is a left side view of the humeral component of FIG. 6A.
Figure 6N:
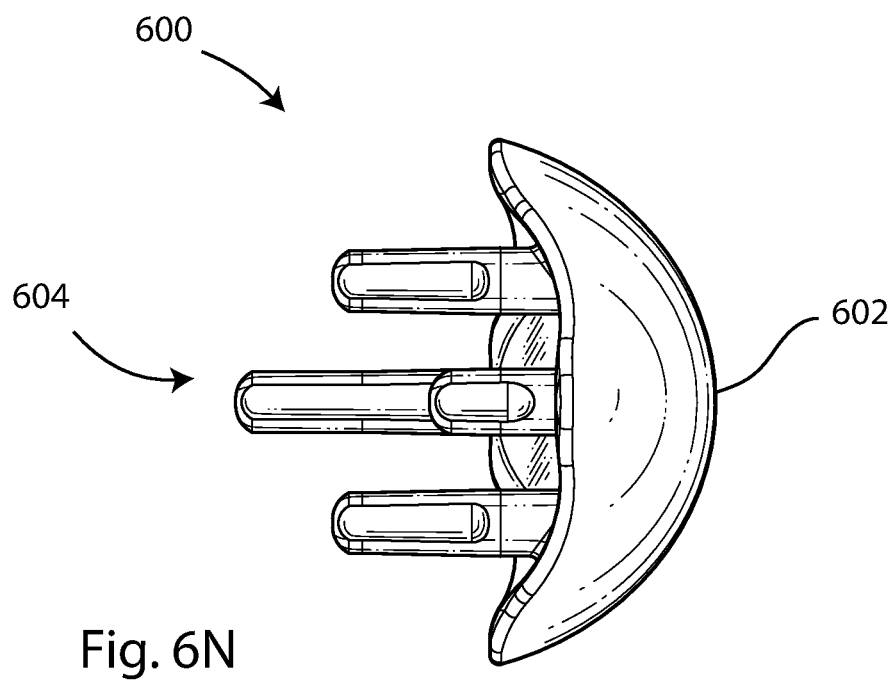
FIG. 6N is a top view of the humeral component of FIG. 6A.
Figure 6O:
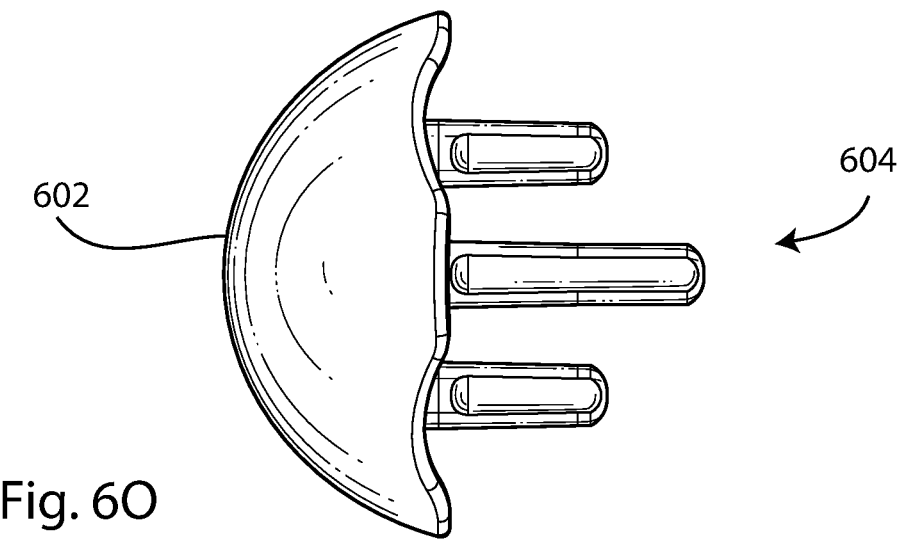
FIG. 6O is a bottom view of the humeral component of FIG. 6A.
Figure 6P:
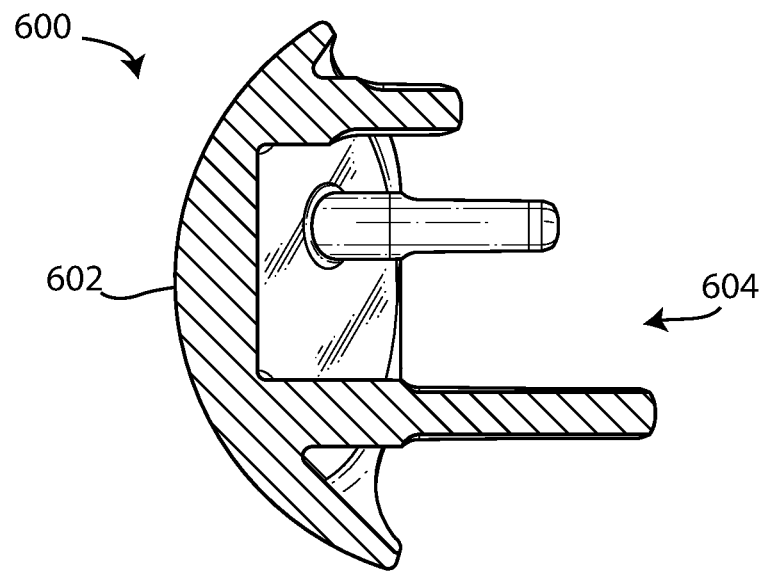
FIG. 6P is a cross sectional view of a left portion of the humeral component of FIG. 6A taken along line 6P-6P of FIG. 6J.
Figure 6Q:
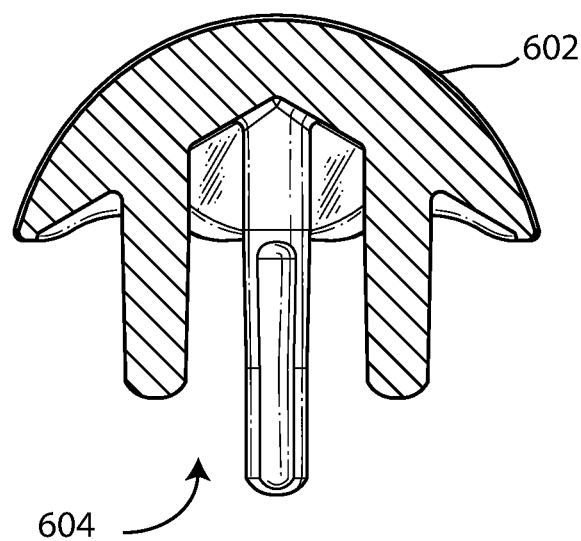
FIG. 6Q is a cross sectional view of a bottom portion of the humeral component of FIG. 6A taken along line 6Q-6Q of FIG. 6J.

Referring to FIGS. 6A-6Q, yet another humeral component 600 includes an articular surface 602 and a bone-facing side 604 which is opposite to the articular surface. Humeral component 600 includes the following features, which may be substantially similar to, or the same as, the corresponding features of humeral component 100: planar surfaces 620, 622, 624, 626; lines 619, 621, 623, 625, 627; fillet radii; points 611, 613; and anchoring elements 628, 630, 632. In an alternate version of the technology, the prosthetic humeral component 600 may have an ellipsoid or ovoid articular surface 602, rather than a spherical articular surface. The planar surfaces 620, 622, 624, 626 are in a concave arrangement in which the planar surfaces converge together as they approach the middle of the articular surface 602, as seen best in FIG. 6A. The planar surfaces diverge as they extend away from the middle of the articular surface 602, and intersect the articular surface to establish an articular margin 606 around a perimeter of the humeral component 600. The articular margin may be described as scalloped or having one or more indentations 629. Each one of the planar surfaces intersects each other planar surface at an obtuse angle, although right angles and acute angles are also contemplated. Planar surface 626 has a smaller area than planar surface 622, and may be described as being indented, or centrally offset, particularly in comparison to planar surface 622. Humeral component 600 includes a fourth anchoring element 634 and a conical surface 674. The illustrated anchoring elements 628, 630, 632, 634 are cylindrical and parallel to one another. Anchoring element 628 may be longer than anchoring elements 630, 632, 634. Anchoring element 634 may be shorter than anchoring elements 628, 630, 632. Anchoring elements 628, 630, 632, 634 also include bilateral longitudinal grooves 636. The conical surface 674 is present around an outermost portion of the bone-facing side 604, and is best seen in FIG. 6D in the vicinity of the outermost portions of lines 621, 623, 625, 627.

Humeral component 600 is bilaterally symmetric about a plane through line 619, and may therefore be implanted in right or left shoulders. Humeral component 600 may be implanted so that planar surface 626 covers a superior aspect of the humeral head, planar surface 622 covers an inferior aspect of the humeral head, planar surfaces 620 and 624 cover anterior and posterior portions of the humeral head, anchoring element 628 extends through the inferior aspect of the humeral head and optionally into the humeral neck, anchoring elements 630, 632 extend into anterior and posterior portions of the humeral head, and anchoring element 634 extends into the superior aspect of the humeral head. The outer portion, or rim, of planar surface 626 faces at least a portion of the rotator cuff, and, because planar surface 626 is indented to form the indentation 629 along the articular margin 606, a space exists between the rim of planar surface 626 and the rotator cuff. This space provides relief, or room, for the rotator cuff to function, thus reducing the risk of rotator cuff damage.

FIGS. 6F and 6G illustrate humeral component 600 in cross sectional views. In each view, two additional smaller size humeral components 600', 600" are superimposed on humeral component 600 to show certain aspects of the design rationale governing the progression from one size to the next. The illustrated design rationale may apply to any of the humeral components disclosed herein. If humeral component 600 is referred to as a large size, then humeral component 600' is a medium size, and humeral component 600" is a small size. However, these small, medium, and large size designations are for the purposes of illustration only. It is understood that a full size range of humeral components may include more than three sizes, including sizes larger than humeral component 600, sizes smaller than humeral component 600", and/or sizes in between those illustrated herein.

The superimposed cross sections of humeral components 600, 600', 600" reveal that the planar surfaces 620, 622, 624, 626; lines 619, 621, 623, 625, 627; fillet radii; points 611, 613; anchoring elements 628, 630, 632, 634, and conical surface 674 are all identical among the three different sizes. In other words, the same bone preparation—saw cuts, drilled holes, and conical ream—may be performed for all humeral component sizes, and any size humeral component may be implanted onto a particular prepared humerus.

The superimposed cross sections of humeral components 600, 600', 600" also show that the various articular surfaces 602, 602', 602" are neither concentric nor tangent. Instead, each articular surface 602, 602', 602" passes through a defined circle 603, which appears as a pair of points 603 in each FIGS. 6F and 6G. This defined circle 603 may be thought of as a gage circle which has a fixed relationship to the features of the bone-facing side 604. The defined circle may lie in the same plane as line 619, for example, or planar surfaces 744, 844 described below. The articular surface 602" of the small humeral component 600" protrudes farther above the circle 603 than do the articular surfaces 602', 602 of the medium and large humeral components 600', 600. Later in this specification, it will be shown that this defined circle 603 may correspond to a depth stop feature on a planar reamer.

Referring to FIGS. 7A-7F, yet another humeral component 700 includes an articular surface 702 and a bone-facing side 704 which is opposite to the articular surface. The articular surface is smooth and polished, and may be spherical, elliptical, or ovoid. Humeral component 700 may be designed with four overlapping circles of a sphere, or as a hemisphere with a tapered, triangular, flat-bottom socket forming the bone-facing side.

Figure 7A:
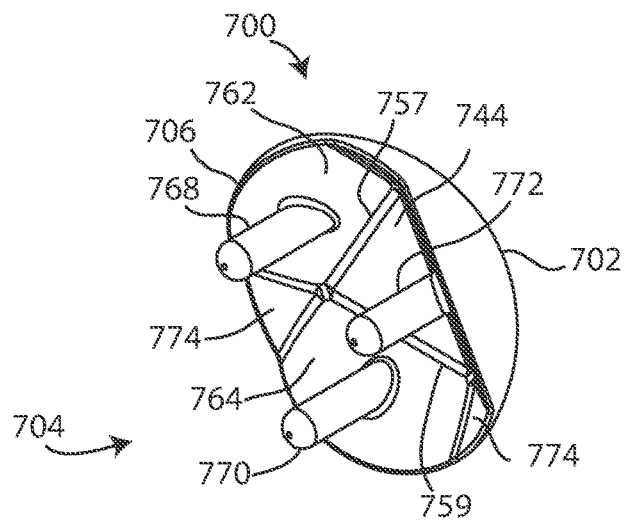
FIG. 7A is an isometric view of yet another humeral component.
Figure 7B:
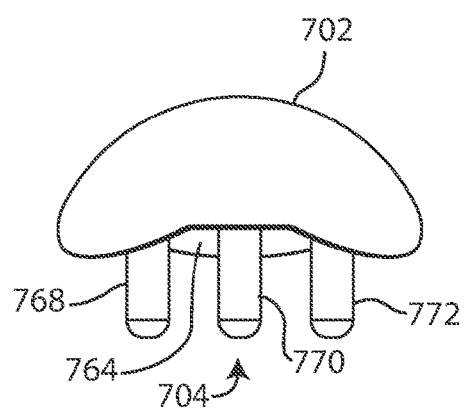
FIG. 7B is a superior view of the humeral component of FIG. 7A.
Figure 7C:
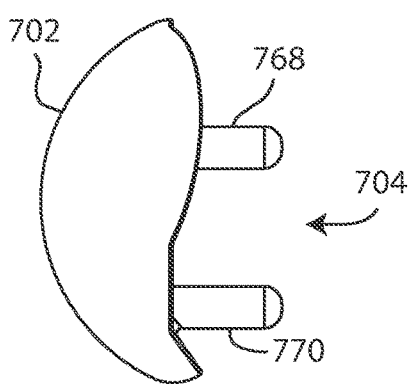
FIG. 7C is an anterior view of the humeral component of FIG. 7A.
Figure 7D:
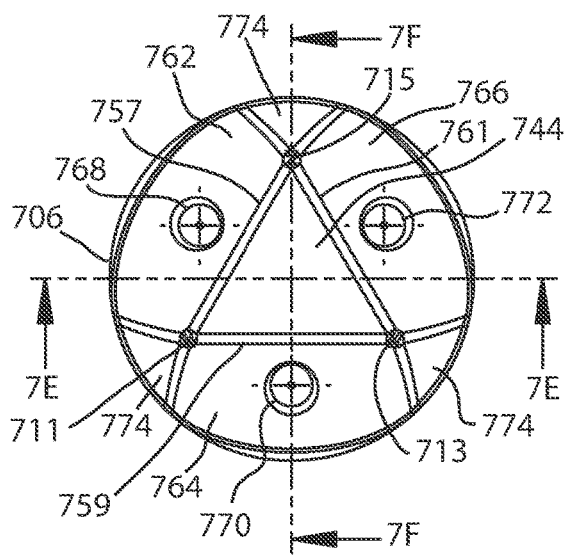
FIG. 7D is a lateral view of the humeral component of FIG. 7A.
Figure 7E:
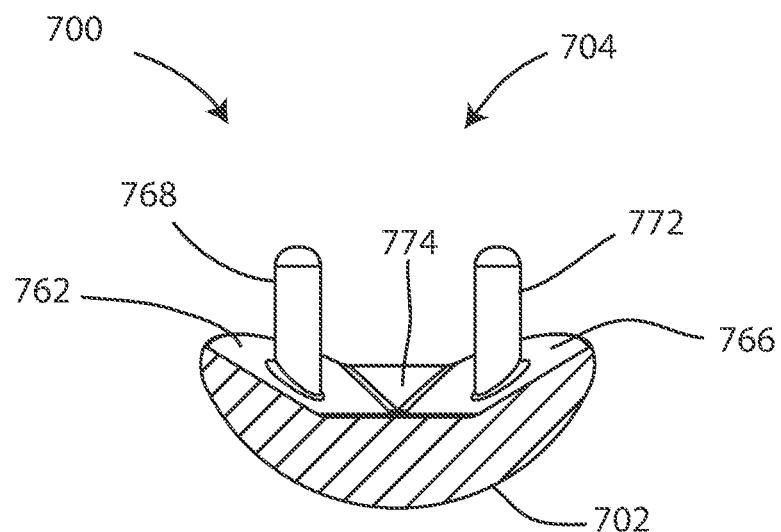
FIG. 7E is a cross sectional view of the humeral component of FIG. 7A, taken along section line 7E-7E of FIG. 7D.
Figure 7F:
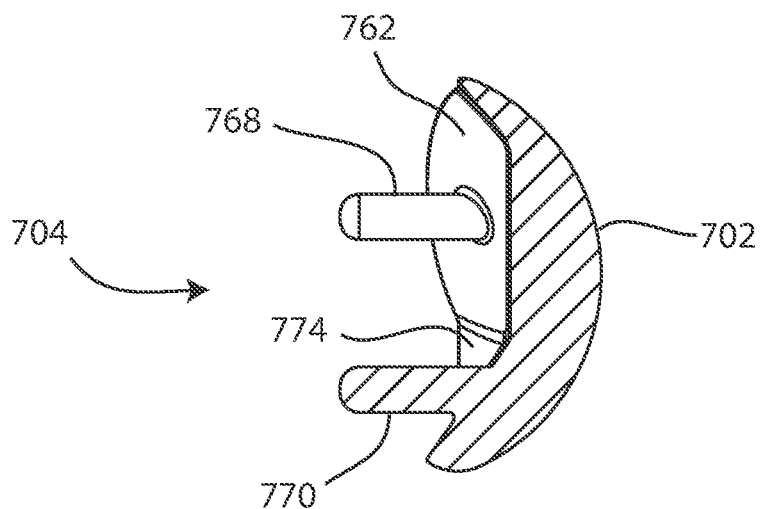
FIG. 7F is a cross sectional view of the humeral component of FIG. 7A, taken along section line 7F-7F of FIG. 7D.

Humeral component 700 may include four planar surfaces 744, 762, 764, 766 in a concave arrangement in which the planar surfaces 762, 764, 766 converge together as they approach the middle of the articular surface 702 and the planar surface 744, as seen best in FIG. 7A. Other examples may include three, five, or more planar surfaces in a concave arrangement. Each one of the planar surfaces intersects each other planar surface at an obtuse angle, although right angles and acute angles are also contemplated. Planar surfaces 744, 762 intersect along a line 757, planar surfaces 744, 764 intersect along a line 759, and planar surfaces 744, 766 intersect along a line 761. Planar surfaces 762, 764; 764, 766; and 766, 762 also intersect when extended. The lines 757, 759, 761 may also be referred to as intersections, edges, or internal corners, and may include fillet radii, as best seen in FIG. 7D. Referring to FIG. 7D, lines 757, 759 intersect at a first point 711; lines 759, 761 intersect at a second point 713; and lines 757, 761 intersect at a third point 715. Humeral component 700 also includes a conical surface 774, which is present in the vicinity of the outermost portions of lines 757, 759, 761, as best seen in FIG. 7D.

The humeral component 700 may have a roughened bone-facing side 704, or undersurface, which rests on the prepared bone of the humerus when the humeral component is implanted. From this undersurface or bone-facing side 704, at least one anchoring element 768 projects outwardly. The example shown includes three anchoring elements 768, 770, 772 protruding from planar surfaces 762, 764, 766, respectively. The anchoring elements project into the humeral bone when the humeral component is implanted, and may anchor the humeral component to prevent loosening or micromotion. The anchoring elements may be pegs which are round, cruciate, or have fins, or have another cross sectional shape for bone fixation. The anchoring elements may include fenestrations. Some of the examples disclosed herein utilize three pegs, but the number of pegs may vary. The pegs may be parallel, converging, diverging, or skew. The pegs may be smooth, matte, rough, or porous to promote bone cement fixation or bone ingrowth. The illustrated anchoring elements 768, 770, 772 are cylindrical and parallel to one another.

Humeral component 700 is bilaterally symmetric about a plane through section line 7F-7F of FIG. 7D, and trilaterally symmetric about an axis normal to planar surface 744. Humeral component 700 may therefore be implanted in right or left shoulders. Humeral component 700 may be implanted so that planar surface 764 covers an inferior aspect of the humeral head, planar surfaces 762 and 766 cover anterior-superior and posterior-superior portions of the humeral head, anchoring element 770 extends through the inferior aspect of the humeral head and optionally into the humeral neck, and anchoring elements 768, 772 extend into anterior and posterior portions of the humeral head. However, due to its trilateral symmetry, humeral component 700 may also be implanted so that planar surface 762 or planar surface 766 covers the inferior aspect of the humeral head instead of planar surface 764.

Referring to FIGS. 8A-8D, yet another humeral component 800 includes an articular surface 802 and a bone-facing side 804 which is opposite to the articular surface.

Figure 8A:
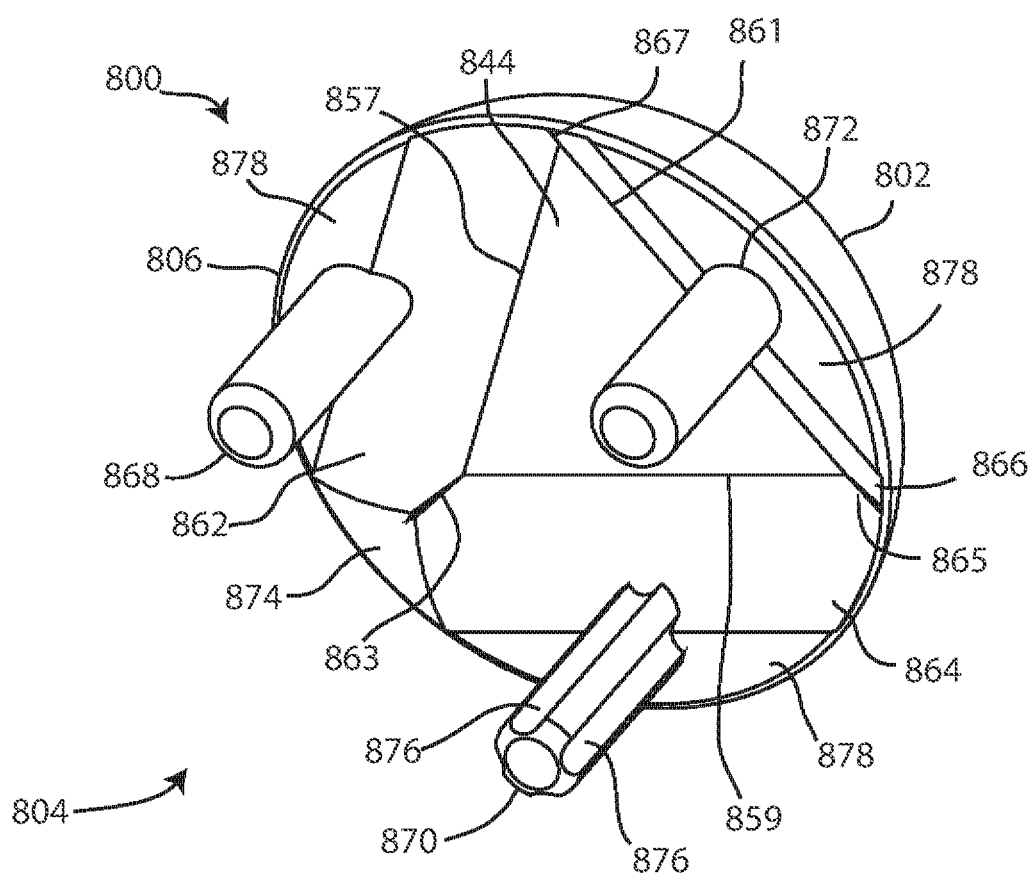
FIG. 8A is an isometric view of yet another humeral component.

Humeral component 800 includes the following features, which may be substantially similar to, or the same as, the corresponding features of humeral component 700: planar surfaces 844, 862, 864, 866; lines 857, 859, 861; points 811, 813, 815; conical surface 874; anchoring elements 868, 870, 872. In an alternate version of the technology, the prosthetic humeral component 800 may have an ellipsoid or ovoid articular surface 802, rather than a spherical articular surface. The planar surfaces 844, 862, 864, 866 are in a concave arrangement in which the planar surfaces 862, 864, 866 converge together as they approach the middle of the articular surface 802 and the planar surface 844, as seen best in FIG. 8A. Each one of the planar surfaces intersects each other planar surface at an obtuse angle, although right angles and acute angles are also contemplated. Planar surfaces 862, 864 intersect along a line 863, planar surfaces 864, 866 intersect along a line 865, and planar surfaces 862, 866 intersect along a line 867. No fillet radii are shown in this example. The illustrated anchoring elements 868, 870, 872 are cylindrical and parallel to one another. Anchoring element 870 also includes four longitudinal grooves 876 which are equally spaced around the anchoring element. Anchoring element 870 may be described as having a cruciate or plus-shaped cross section. Humeral component 800 includes a planar surface 878, which is present in the vicinity of the outermost portions of planar surfaces 862, 864, 866, as best seen in FIG. 8A. Planar surface 878 may be parallel to planar surface 844.

Figure 8B:
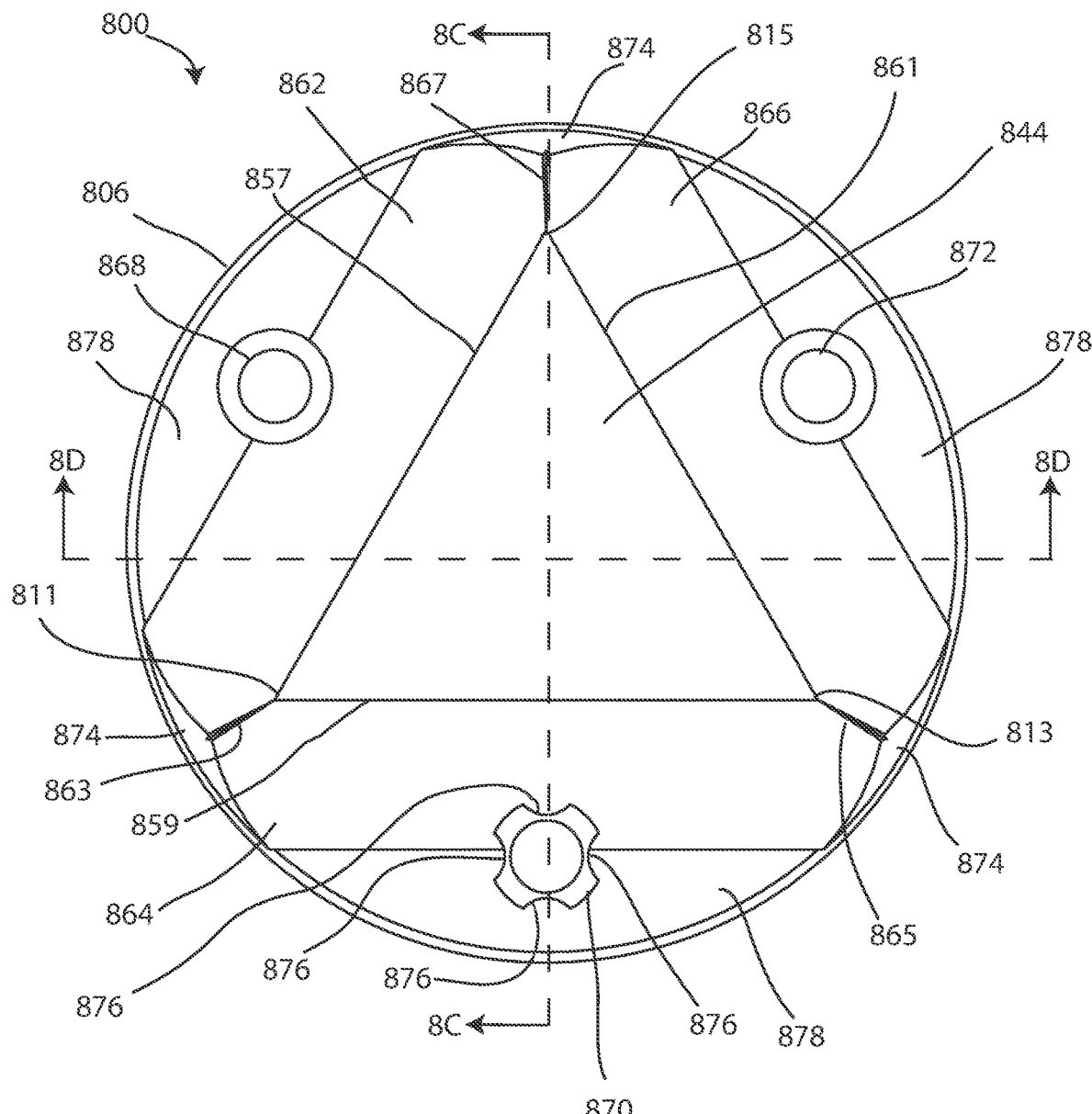
FIG. 8B is a lateral view of the humeral component of FIG. 8A.
Figure 8C:
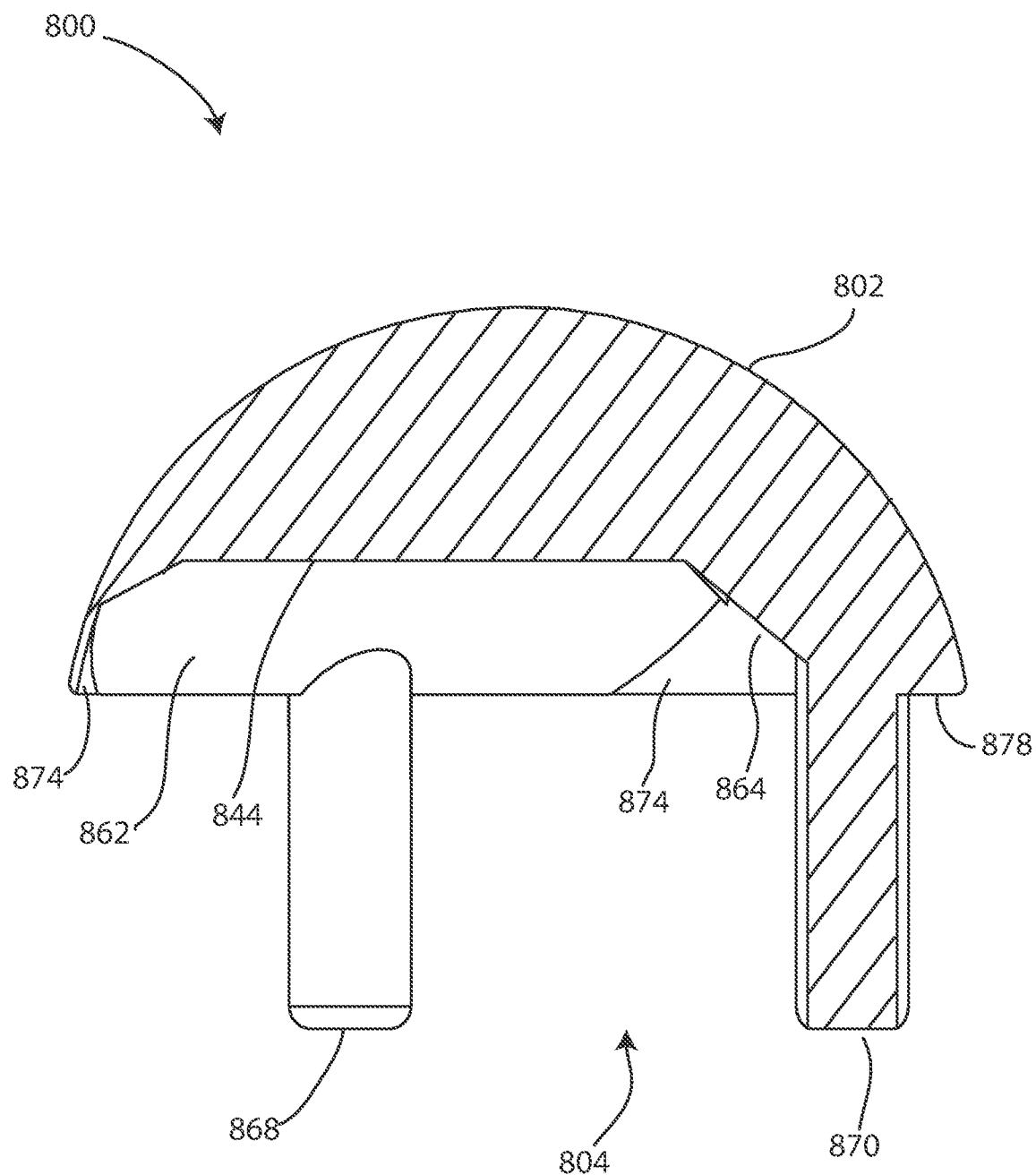
FIG. 8C is a cross sectional view of the humeral component of FIG. 8A, taken along section line 8C-8C of FIG. 8B.
Figure 8D:
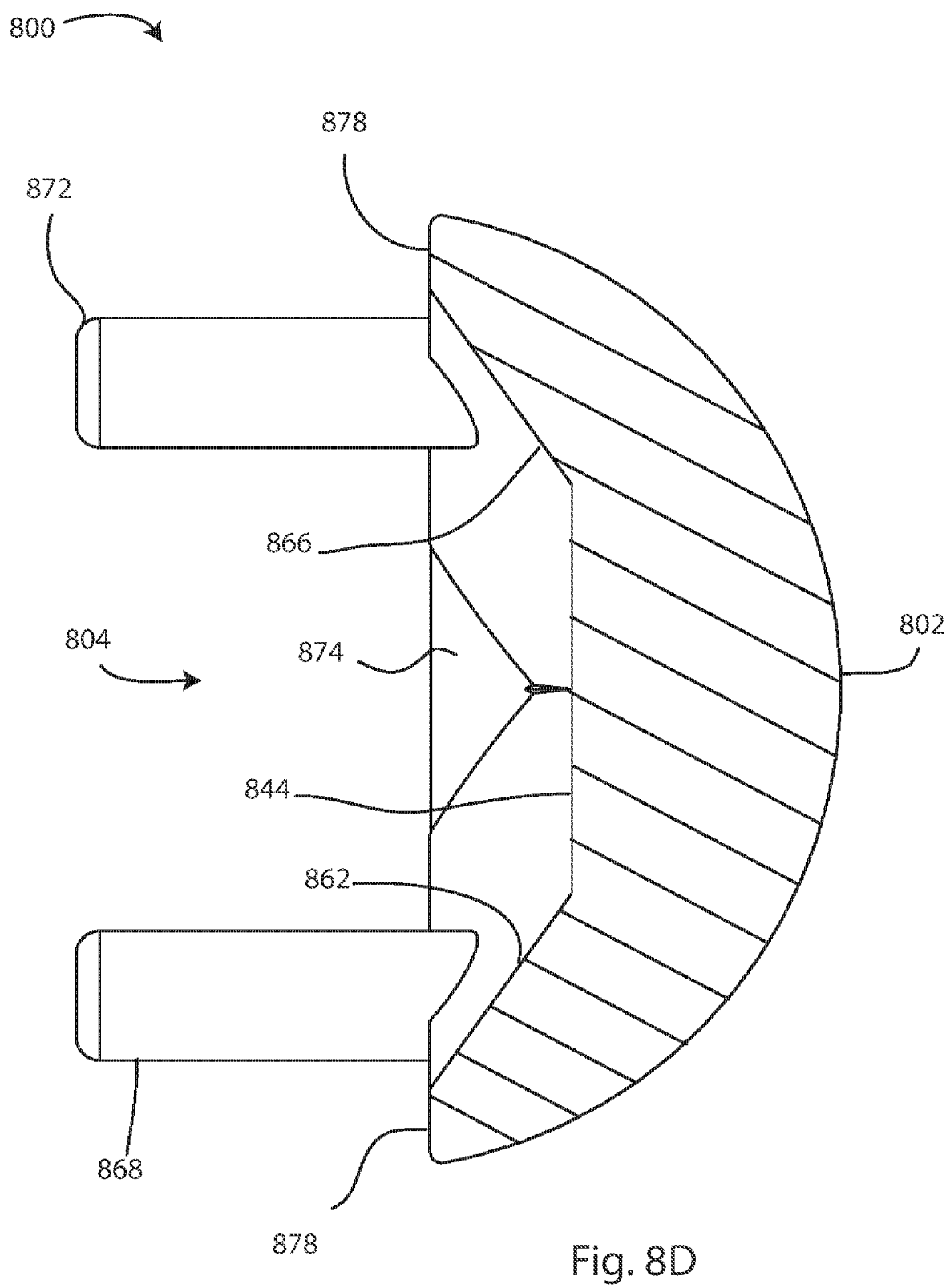
FIG. 8D is a cross sectional view of the humeral component of FIG. 8A, taken along section line 8D-8D of FIG. 8B.

Humeral component 800 is bilaterally symmetric about a plane through section line 8C-8C of FIG. 8B, and trilaterally symmetric about an axis normal to planar surface 844. Humeral component 800 may therefore be implanted in right or left shoulders. Humeral component 800 may be implanted so that planar surface 864 covers an inferior aspect of the humeral head, planar surfaces 862 and 866 cover anterior-superior and posterior-superior portions of the humeral head, anchoring element 870 extends through the inferior aspect of the humeral head and optionally into the humeral neck, and anchoring elements 868, 872 extend into anterior and posterior portions of the humeral head. However, due to its trilateral symmetry, humeral component 800 may also be implanted so that either planar surface 862 or 866 covers the inferior aspect of the humeral head instead of planar surface 864.

Figure 9A:
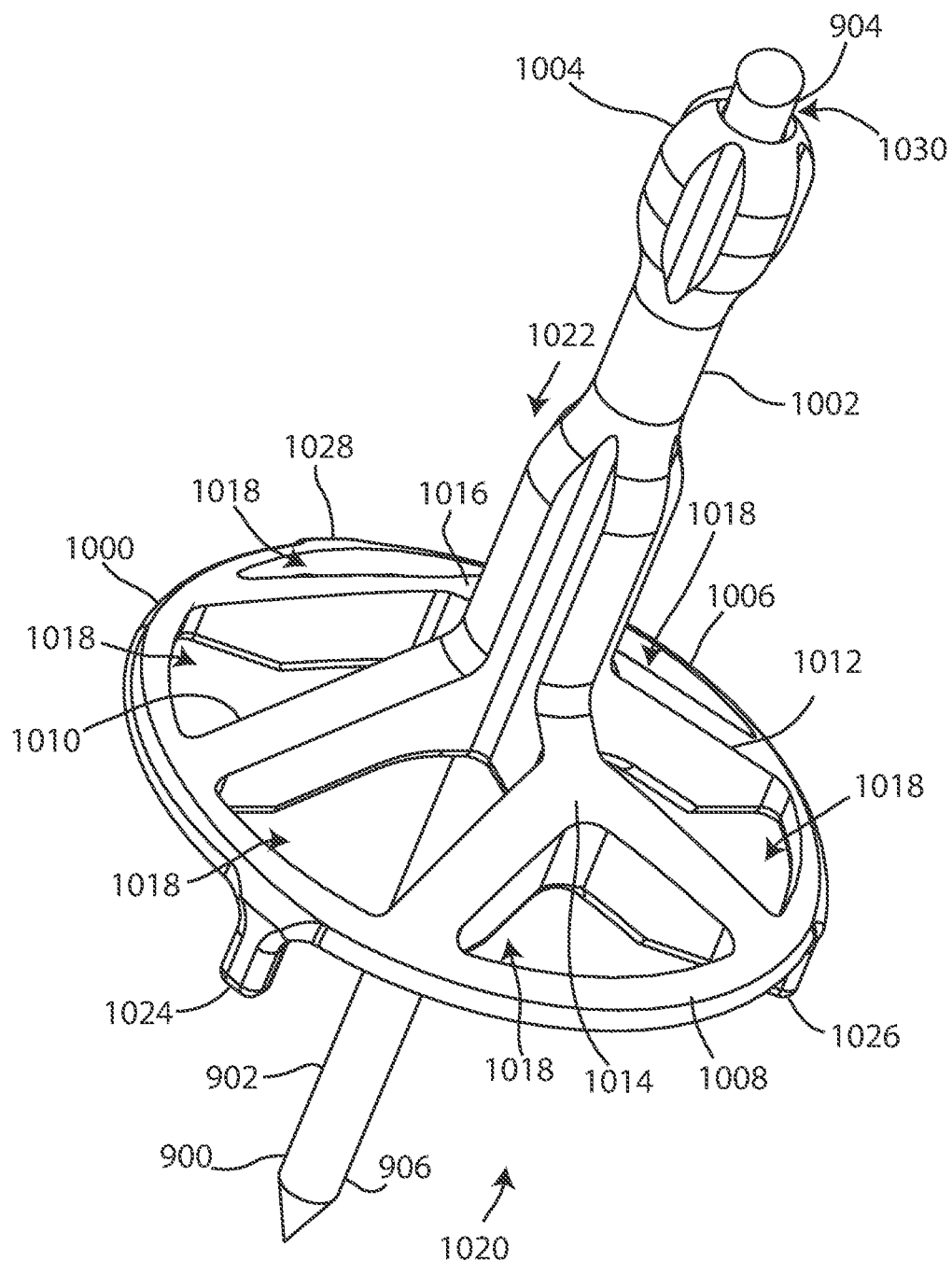
FIG. 9A is an isometric view of a pin and a template.

Referring to FIG. 9A, a guide wire or pin 900 and a template 1000 arc shown in an operative arrangement. The template 1000 may be used to establish the desired orientation of the implanted humeral component relative to the intact proximal humeral anatomy, and may guide insertion of the pin 900 into the humeral head. The desired orientation of the humeral component may relate to an axis which is normal to a central portion of the intact articular surface of the humeral head, or parallel to the intact humeral neck axis.

The pin 900 is a slender elongated shaft 902 which extends between a proximal end 904 and a distal tip 906. The shaft 902 may be circular in cross-section as shown, or non-circular in cross-section. The proximal end 904 may include a torque connector for connection to a T-handle, drill, or other torque source. The distal tip 906 may be threaded, fluted for cutting, pointed, faceted as in a trocar tip, rounded, or blunt.

Figure 9B:
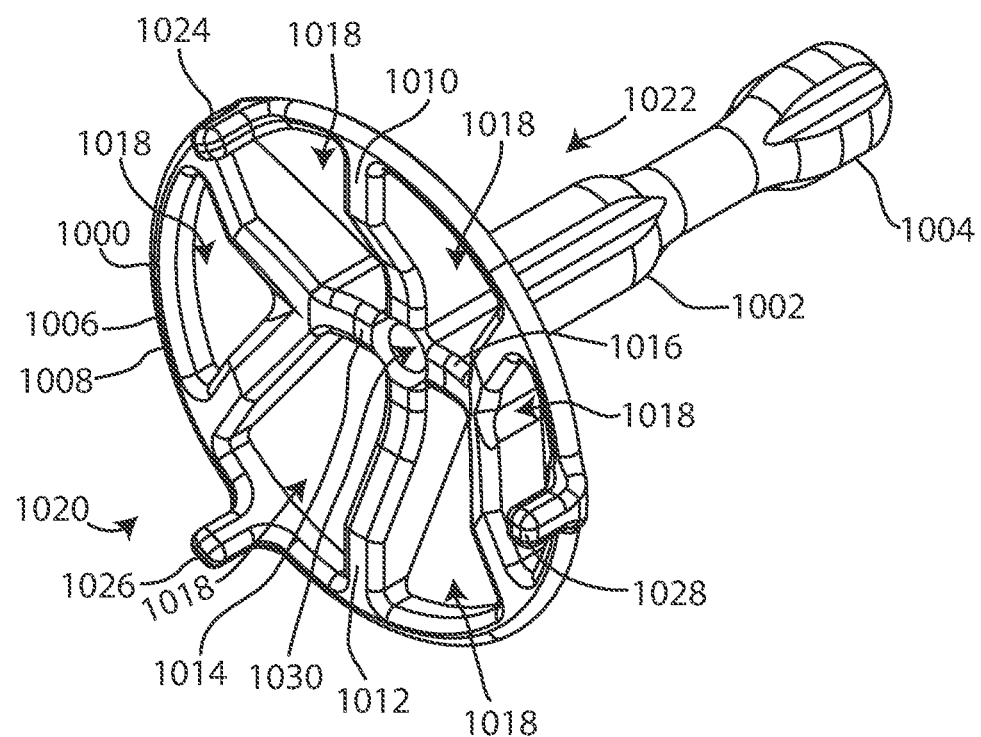
FIG. 9B is another isometric p z view of the template of FIG. 9A from a different viewpoint.

Referring to FIGS. 9A-9B, the template 1000 includes a shaft 1002 which extends between a proximal end 1004 and a distal working portion 1006. The proximal end 1004 may include a handle or a coupling. The working portion 1006 includes a round perimeter rim 1008 which may be connected to the shaft 1002 by one or more arms 1010. The example shown includes bilateral straight arms 1010, 1012 interposed between bilateral bifurcated arms 1014, 1016. One or more apertures 1018 may extend between the arms; six apertures 1018 are shown in the example. The working portion 1006 has a bone-facing side 1020 and an opposite side 1022. The bone-facing side may be concave as shown, convex, or flat. The opposite side 1022 may complement the bone-facing side 1020. One or more projections 1024 may extend from the rim 1008; three projections 1024, 1026, 1028 are shown, equally spaced around the rim 1008. The shaft 1002 may include a central cannulation 1030 which receives the pin 900.

Figure 28:
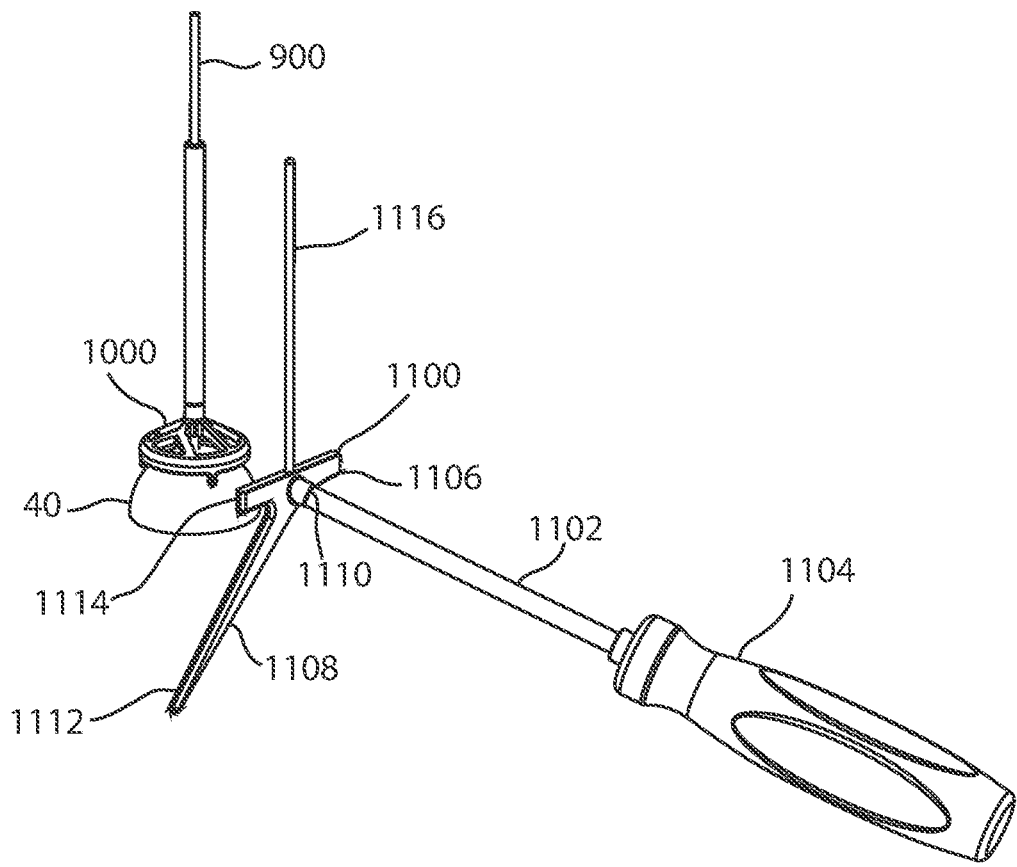
FIG. 28 is an isometric view of the template, pin, and simplified humeral head of FIG. 27 operatively arranged relative to an alignment guide.

Referring to FIG. 28, an alignment guide 1100 is shown in use with the pin 900 and the template 1000 relative to a simplified humeral head 40. The alignment guide 1100 may provide additional anatomical referencing beyond that provided by the template 1000, in order to set the desired orientation of the implanted humeral component relative to the intact proximal humeral and forearm anatomy.

The alignment guide 1100 includes a shaft 1102 which extends between a proximal handle 1104 and a distal working portion 1106. In use, the shaft 1102 is aligned with the patient's forearm in consideration of aligning the pin 900 in the desired rotational anteversion and retroversion of the patient. The working portion 1106 includes a plate 1108 and at least one socket 1110 for releasably or permanently coupling to the shaft 1102. The plate 1108 may include a humeral shaft extension 1112, an articular bar 1114, and a post 1116. The articular bar 1114 may cross the humeral shaft extension 1112 at an oblique angle to form a "T" shape. The post 1116 may extend perpendicular to the articular bar 1114 opposite the humeral shaft extension 1112. The socket 1110 may be located in the area where the articular bar 1114 crosses the humeral shaft extension 1112. The working portion 1106 may include a second socket (not visible in FIG. 28) on an opposite side of the plate 1108 from the socket 1110. The shaft 1102 may be releasably coupled to either socket to provide configurations suitable for right or left shoulder procedures.

Figure 10A:
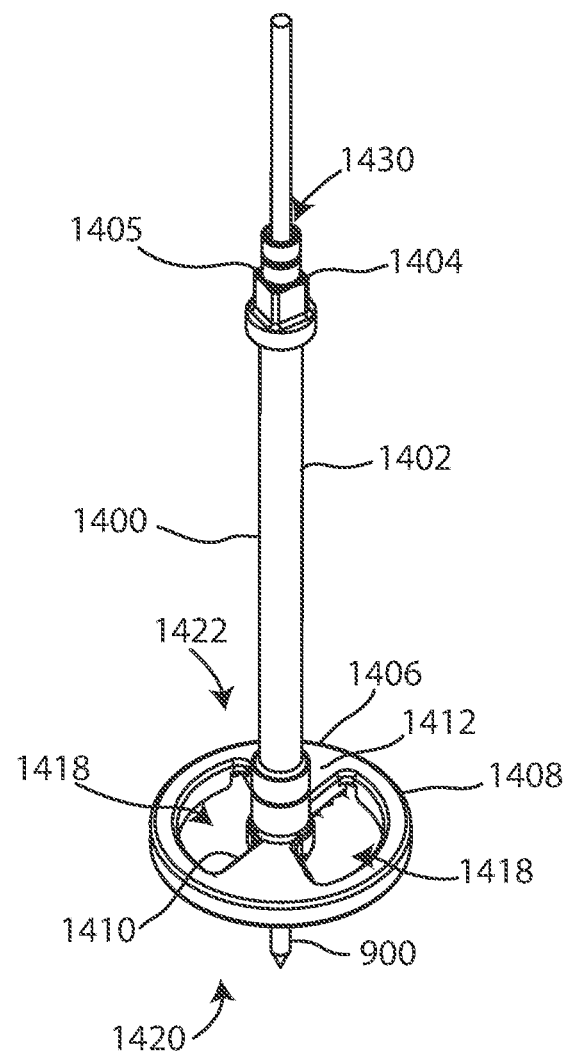
FIG. 10A is an isometric view of the pin of FIG. 9A and a planar reamer.
Figure 10B:
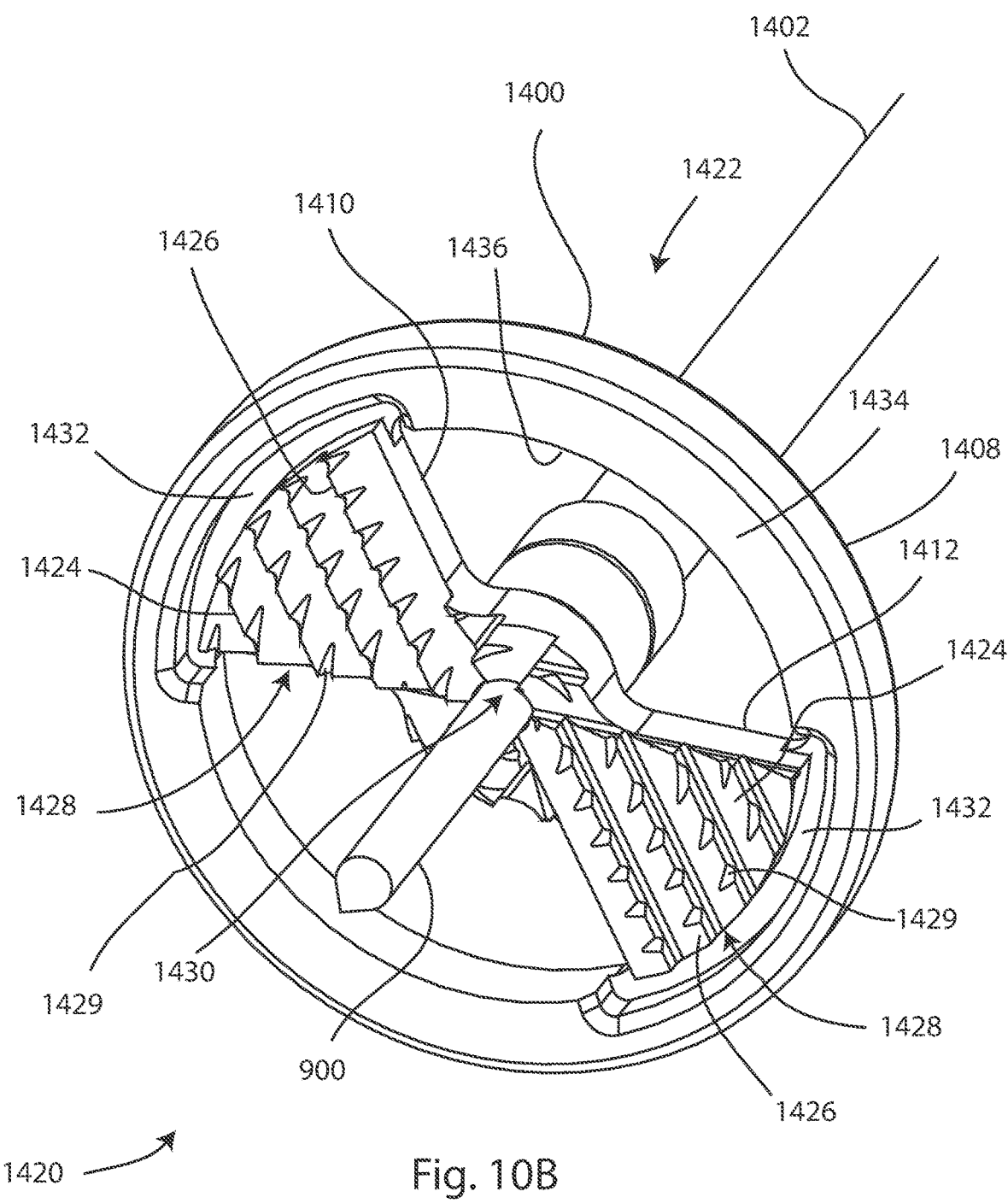
FIG. 10B is another isometric view of a portion of the pin and planar reamer of FIG. 10A from a different viewpoint.

Referring to FIGS. 10A-10B, the pin 900 and a planar reamer 1400 are shown in an operative arrangement. The planar reamer 1400 may be used to cut a planar bone resection 44 which is perpendicular to the axis of the pin 900 and which may have an outer diameter corresponding to the defined circle 603. The bone resection 44 may correspond to planar surfaces 744, 844, or it may correspond to lines 119, 219, 319, 419, 519, 619.

The planar reamer 1400 includes a shaft 1402 which extends between a proximal end 1404 and a distal working portion 1406. The proximal end 1404 may include a handle or a coupling; a torque coupling 1405 is shown for coupling the planar reamer 1400 to a T-handle, drill, or other torque driver. The working portion 1406 includes a round perimeter rim 1408 which may be connected to the shaft 1402 by one or more arms 1410. The example shown includes bilateral arms 1410, 1412. One or more apertures 1418 may extend between the arms; two apertures are shown in the example. The working portion 1406 has a bone-facing side 1420 and an opposite side 1422. The bone-facing side 1420 is flat. Cutting features 1424 are present on the bone-facing side 1420. In this example, the cutting features 1424 include a series of alternating teeth 1426 and grooves 1428 with concentric circular patterns of crossing grooves 1429, which may be referred to as chip breakers. Relief channels 1432 may be included around the outer portion of each arm 1410, 1412 to provide clearance for the tools used to fabricate the cutting features 1424 and/or to delimit an outer diameter of the cutting features. A continuous smooth planar surface 1434 extends completely around the perimeter rim 1408 on the bone-facing side 1420, forming a boundary within which all of the cutting features 1424 are contained. The surface 1434 may be coplanar with the cutting features 1424, for example the peaks of the teeth 1426 or the valleys of the grooves 1428. Alternatively, the surface 1434 may lie above or below the cutting features. The surface 1434 functions as a depth stop in use, as will be described later. An inner edge 1436 of the surface 1434, excluding any interruption caused by the relief channels 1432, may correspond to the defined circle 603 described above. The opposite side 1422 may complement the bone-facing side 1420. The shaft 1402 may include a central cannulation 1430 which receives the pin 900.

Another example of a planar reamer has a plurality of arms that extend radially from the shaft to the rim like spokes on a wheel. This example may or may not have the continuous smooth planar surface that extends completely around the perimeter rim on the bone-facing side. This example may have one or more radially extending cutting teeth per arm. Because this example has through openings between the cutting teeth, the bone and articular cartilage fragments are more easily cleared and the reamer is less likely to clog while reaming.

Figure 11A:
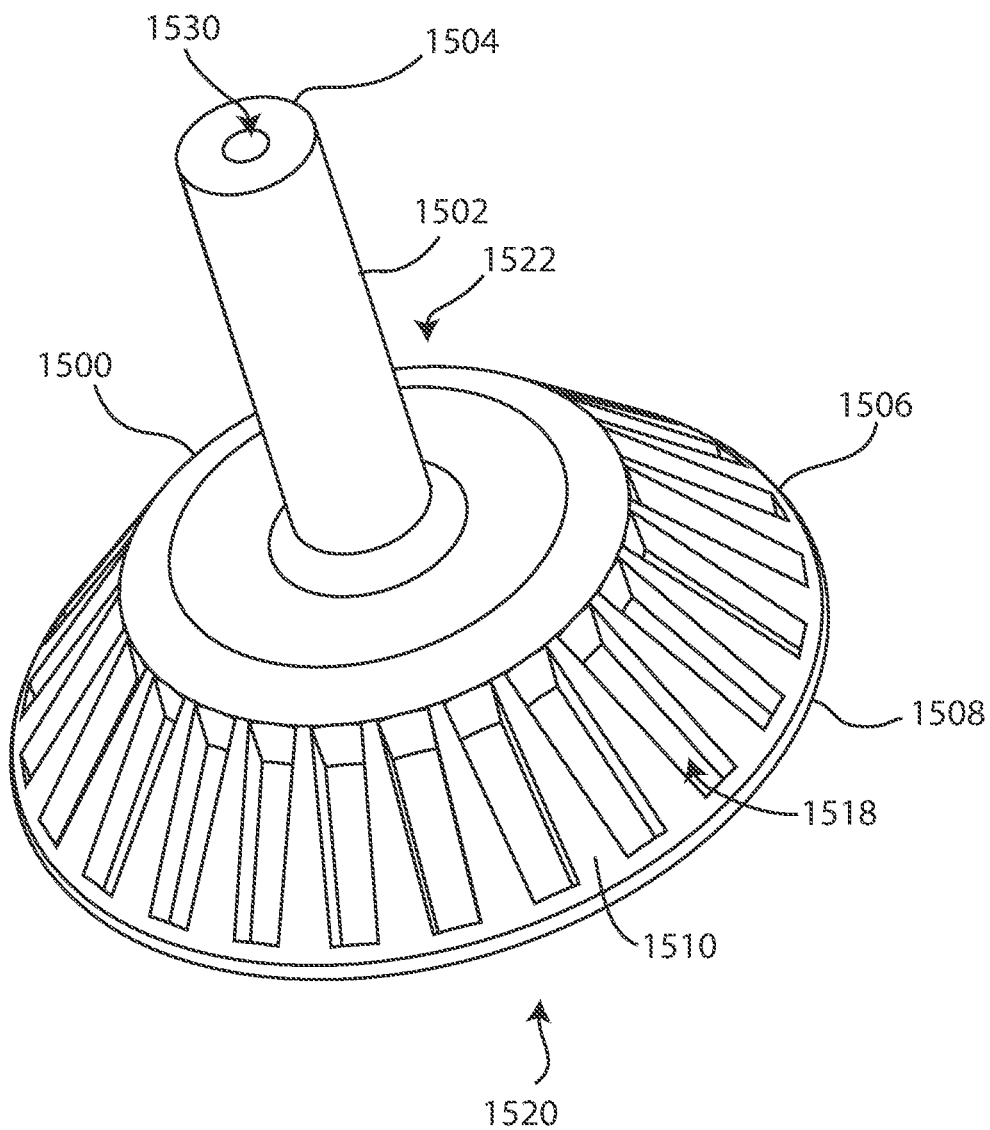
FIG. 11A is an isometric view of a conical reamer.
Figure 11B:
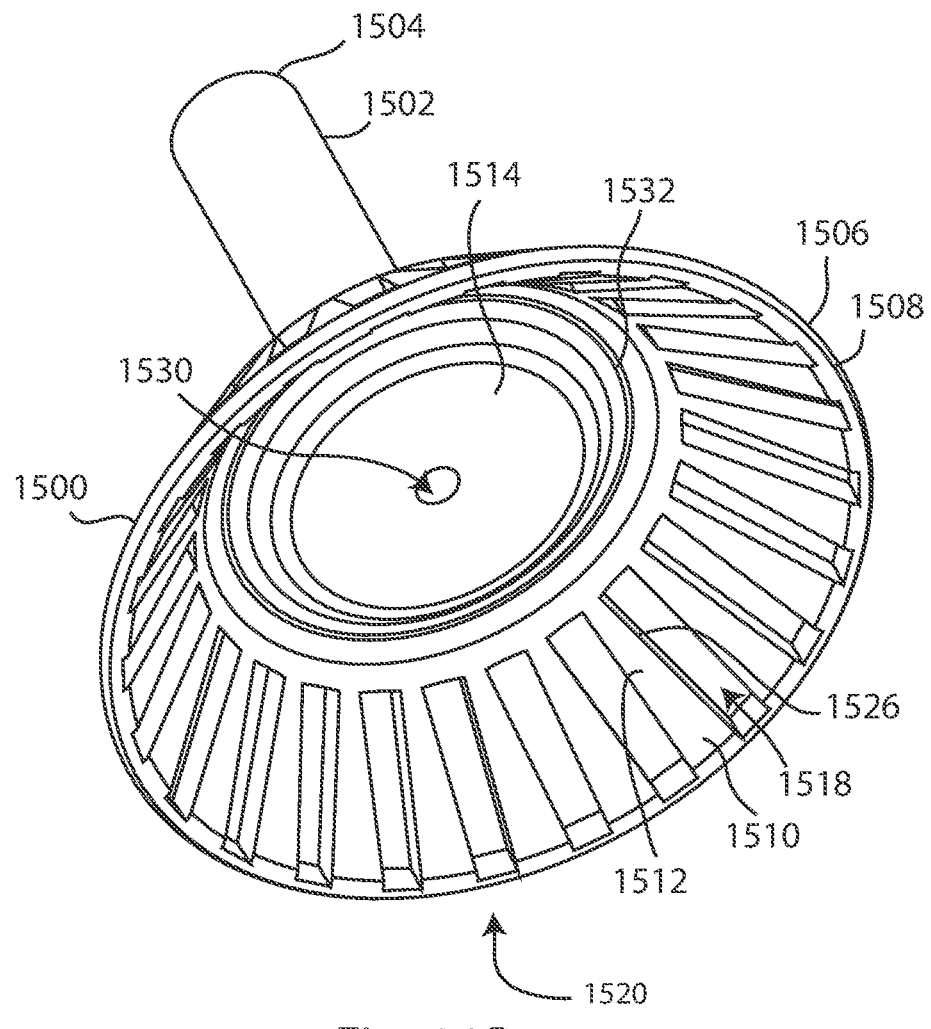
FIG. 11B is another isometric view of the conical reamer of FIG. 11A from a different viewpoint.

Referring to FIGS. 11A-11B, a conical reamer 1500 includes a shaft 1502 which extends between a proximal end 1504 and a distal working portion 1506. The conical reamer 1500 may be used to cut a conical bone resection 74 which corresponds to conical surface 674, 774, 874. The proximal end 1504 may include a handle or a coupling; a blunt proximal end is shown. The working portion 1506 includes a round perimeter rim 1508 which may be connected to the shaft 1502 by one or more arms 1510. The example shown includes a plurality of radially extending arms 1510. One or more apertures 1518 may extend between the arms; a plurality of apertures is shown in the example. However, a roughened file-like tissue-cutting surface may also extend the working portion 1506 allowing rasp-like tissue removal. The working portion 1506 has a bone-facing side 1520 and an opposite side 1522. The bone-facing side includes a conical surface 1512 surrounding a central planar surface 1514 which is perpendicular to the shaft 1502. Cutting features 1524 are present on the bone-facing side. In this example, the cutting features 1524 include a series of radial teeth 1526 on the leading side of each arm 1510 (depending on the direction of rotation, clockwise or counterclockwise). A relief channel 1532 may be included between the central planar surface 1514 and the conical surface 1512. The planar surface 1514 functions as a depth stop in use, as will be described later. The opposite side 1522 may complement the bone-facing side 1520. The shaft 1502 may include a central cannulation 1530 which receives the pin 900.

Specific preparations of the proximal humeral bone surface are disclosed in order to accommodate the multi-planar undersurfaces of the prosthetic components so the undersurfaces rests flush against the bone. The proximal humeral bone may be prepared with the use of a cutting guide which rests on the head of the humerus. The cutting guide has slots which guide a cutting tool such as an oscillating saw blade to make bone cuts corresponding to the particular design of the undersurface of the humeral prosthesis. The humeral cutting guide may be designed to be used by a surgeon utilizing a standard subscapularis tenotomy or lesser tuberosity osteotomy, but may also be adapted to a surgeon utilizing a subscapularis-preserving technique. Various cutting guides will now be described.

Referring to FIGS. 12A-12J, a cutting guide 1600 may be referred to as a cut and drill guide or as an all in one guide. The cutting guide 1600 may be used to guide a cutting tool, such as a saw blade, to cut four planar bone resections 20, 22, 24, 26 corresponding to planar surfaces 120, 122, 124, 126 of humeral component 100, or the planar surfaces of humeral components 200, 300, 400, 500, 600. The cutting guide 1600 may also be used to guide a cutting tool, such as a drill or reamer, to cut bone holes 28, 30, 32 corresponding to anchoring elements 128, 130, 132 of humeral component 100, or the anchoring elements of humeral components 200, 300, 400, 500, 600. The cutting guide 1600 may also serve the function of the template 1000.

Figure 12B:
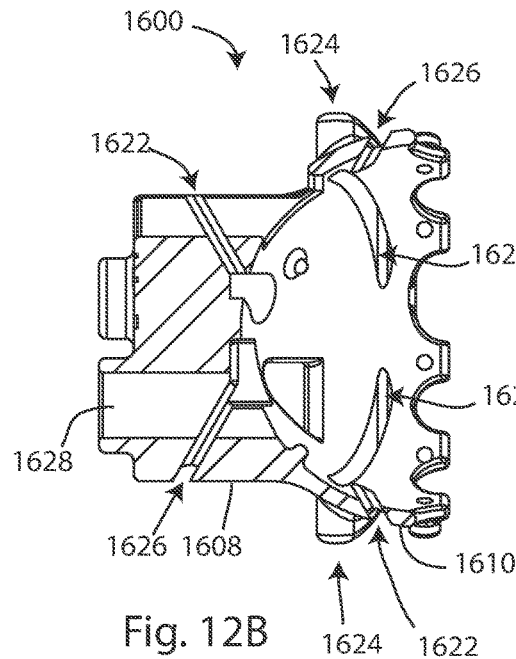
FIG. 12B is a cross sectional view of the cutting guide of FIG. 12A, taken along section line 12B-12B of FIG. 12A.
Figure 12A:
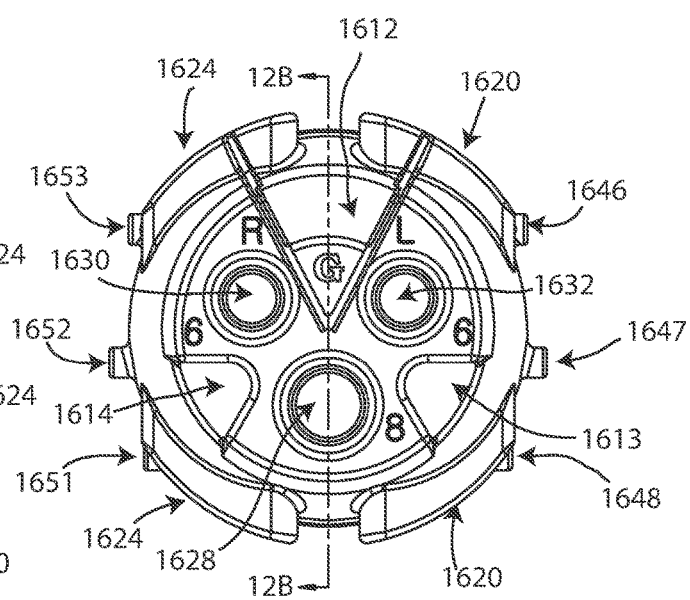
FIG. 12A is a top view of a cutting guide.
Figure 12C:
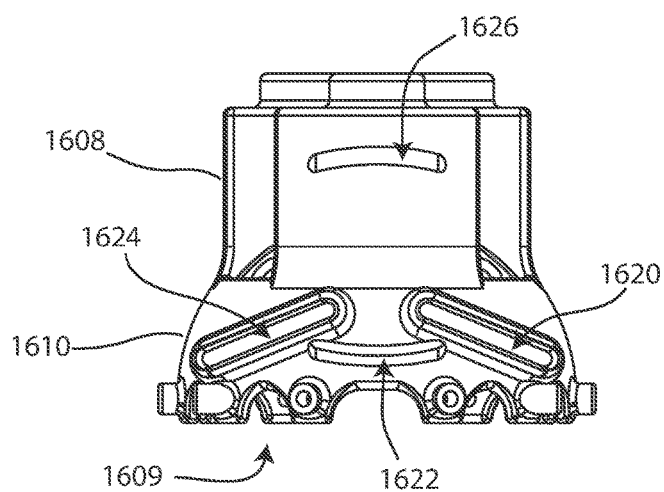
FIG. 12C is a front view of the cutting guide of FIG. 12A.
Figure 12D:
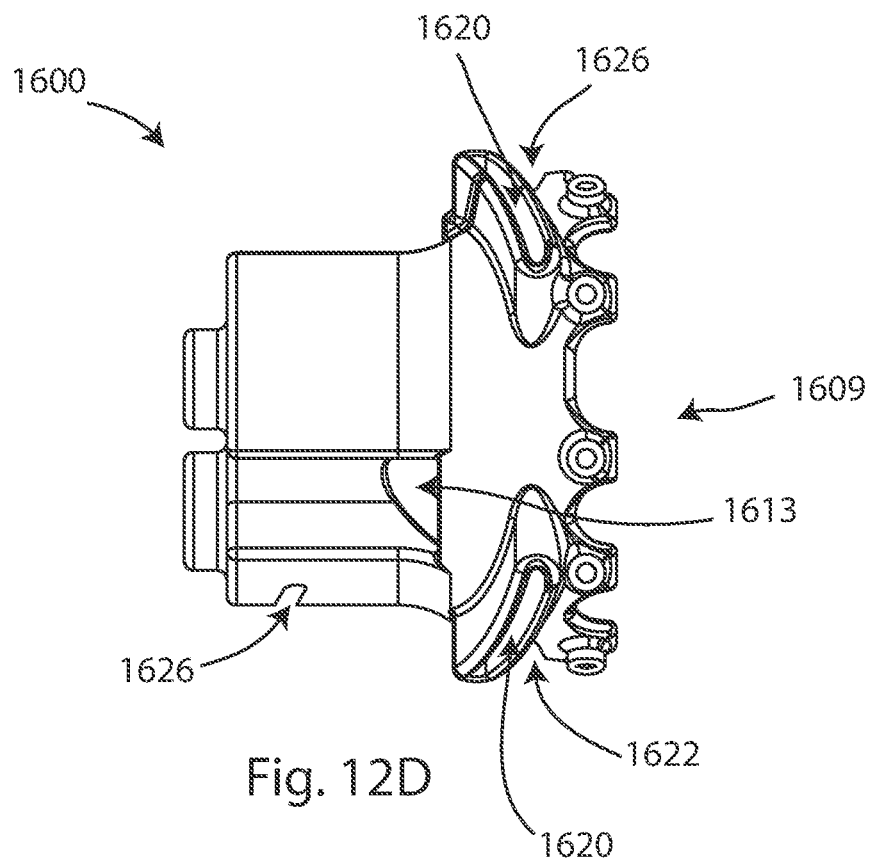
FIG. 12D is a side view of the cutting guide of FIG. 12A.
Figure 12E:
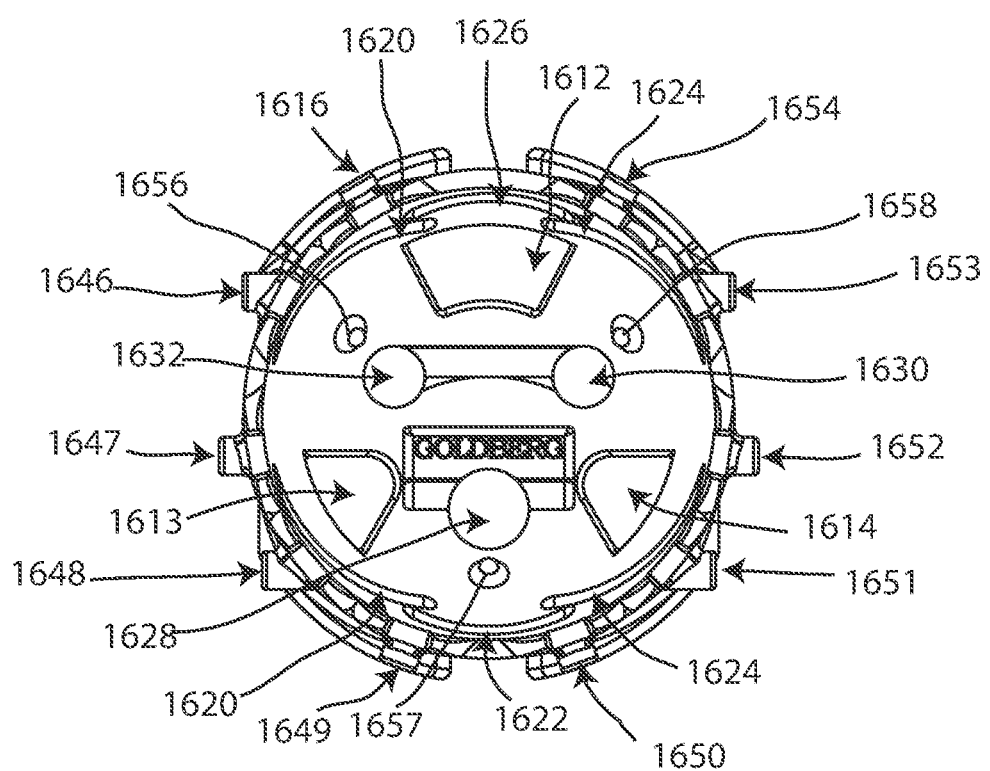
FIG. 12E is a bottom view of the cutting guide of FIG. 12A.
Figure 12F:
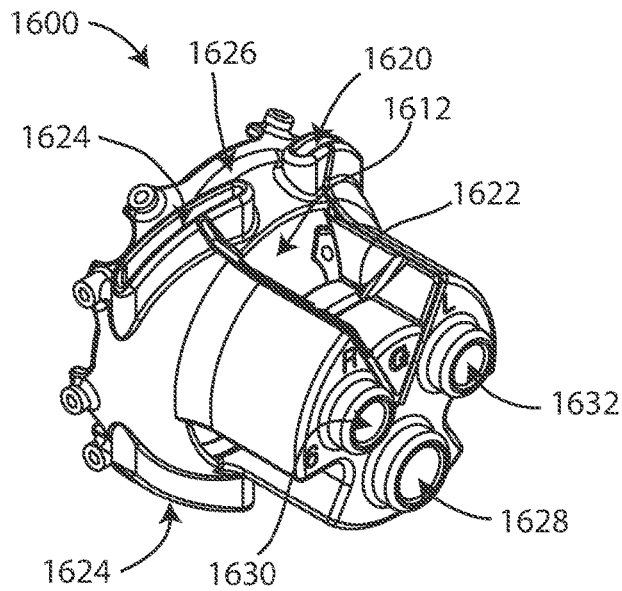
FIGS. 12F, 12G, 12H, 12I, and FIG. 12J are isometric views of the cutting guide of FIG. 12A from several different viewpoints.
Figure 12G:
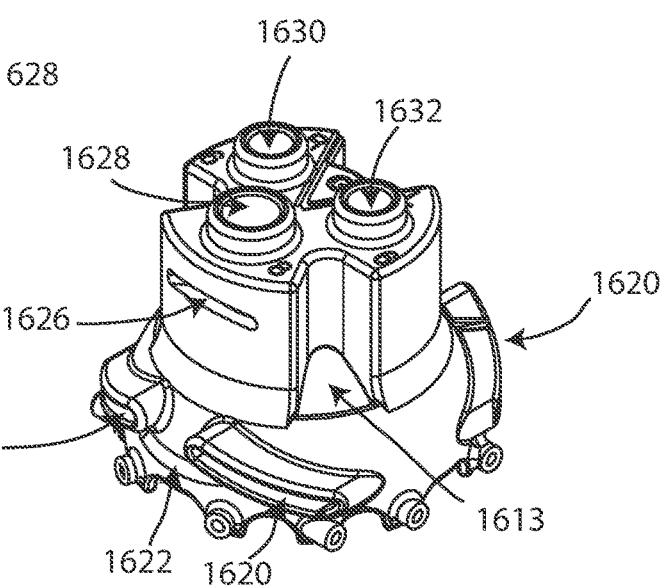
Figure 12H:
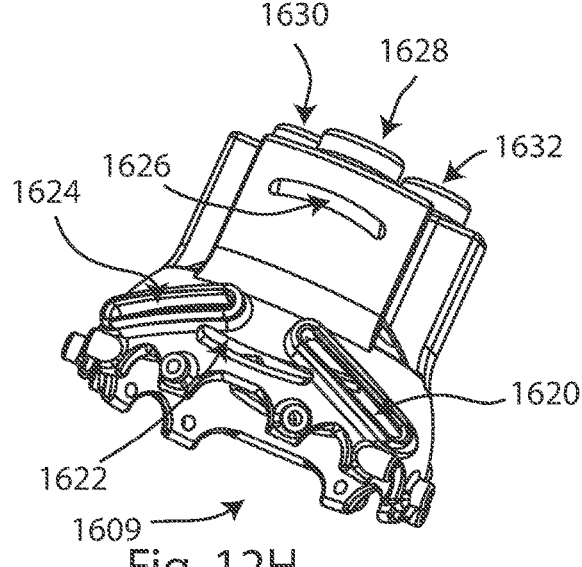
Figure 12I:
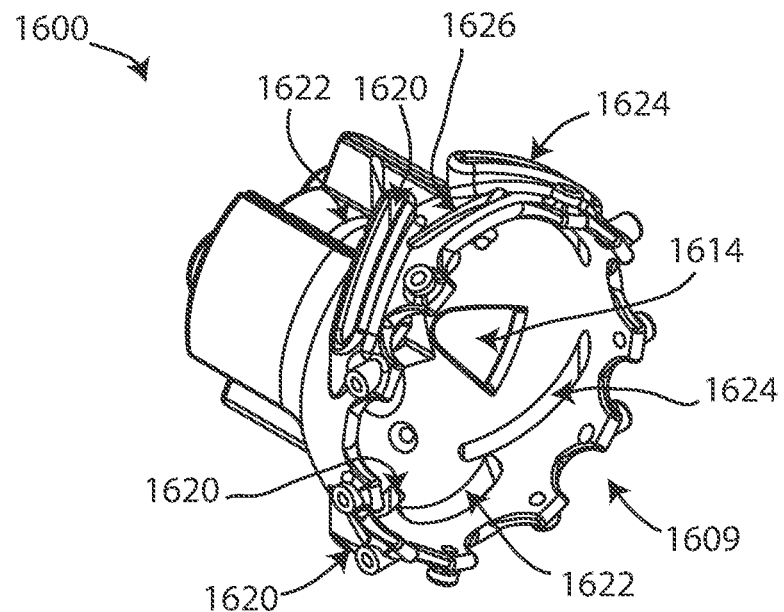
Figure 12J:
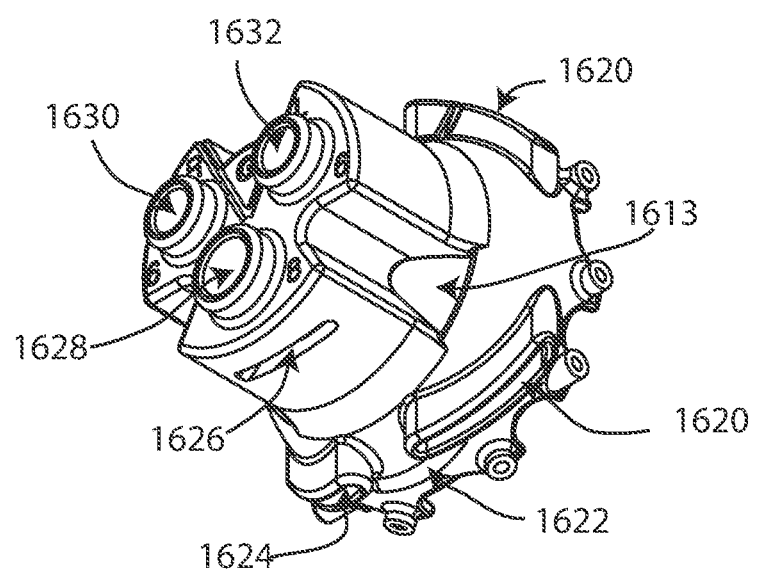

The cutting guide 1600 includes a cylindrical body 1608 terminating at one end in a spherical shell or cup 1610. The cutting guide 1600 has a bone-facing side 1609 which includes the perimeter rim and concave interior of the spherical cup 1610. Three holes 1628, 1630, 1632 extend lengthwise through the cutting guide 1600, corresponding to the relative arrangement of anchoring elements 128, 130, 132 of humeral component 100, or the anchoring elements of humeral components 200, 300, 400, 500, 600. A fourth hole (not shown) may be included in the cutting guide 1600, corresponding to anchoring elements 434, 534, 634 of humeral components 400, 500, 600. One or more apertures 1612 may also extend lengthwise through the cutting guide 1600 to provide visualization windows and/or to reduce weight. Three apertures 1612, 1613, 1614 are shown in the example, interposed between the holes 1628, 1630, 1632. Four slots 1620, 1622, 1624, 1626 extend obliquely through the cutting guide 1600, corresponding to the relative arrangement of planar surfaces 120, 122, 124, 126 of humeral component 100, or the planar surfaces of humeral components 200, 300, 400, 500, 600. It will be appreciated that the number and arrangement of holes and/or slots in the illustrated cutting guide 1600 may be modified to correspond to the number and arrangement of anchoring elements and/or planar surfaces of humeral components 700, 800. One or more holes 1616 may extend through the cutting guide 1600 near the rim of the spherical cup 1610 to receive pins to fix the cutting guide 1600 to the humeral head prior to making any bone resections or holes; ten holes 1616, 1646, 1647, 1648, 1649, 1650, 1651, 1652, 1653, 1654 are shown. Holes 1646, 1647, 1648, 1651, 1652, 1653 are all parallel, and holes 1646, 1653; 1647, 1652; and 1648, 1651 are coaxial. Referring to FIG. 12E, one or more projections 1656 may extend from the interior of the spherical cup 1610 to engage the articular surface of the humeral head. The example shows three projections 1656, 1657, 1658.

Figure 13A:
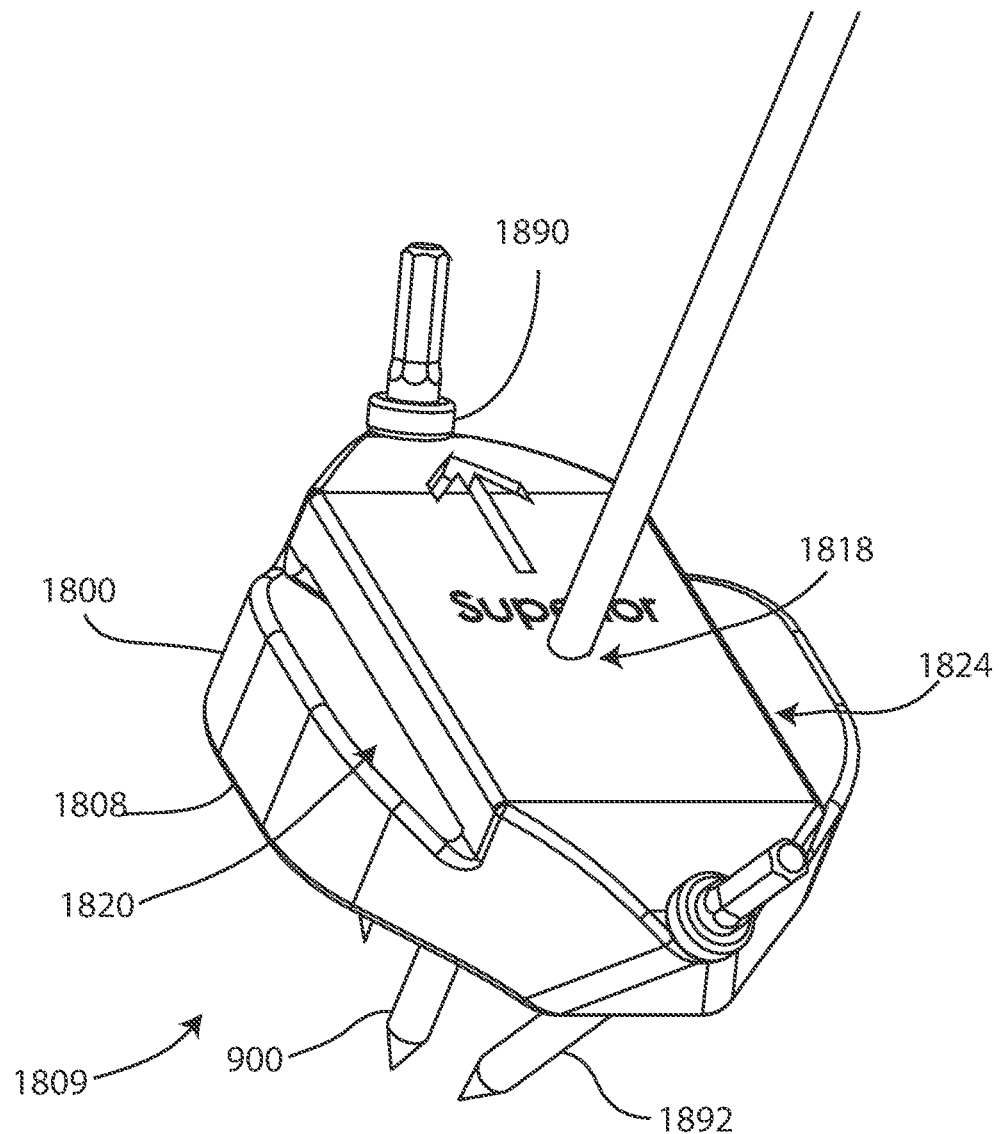
FIG. 13A is an isometric view of another cutting guide with the pin of FIG. 9A and two fasteners.
Figure 13B:
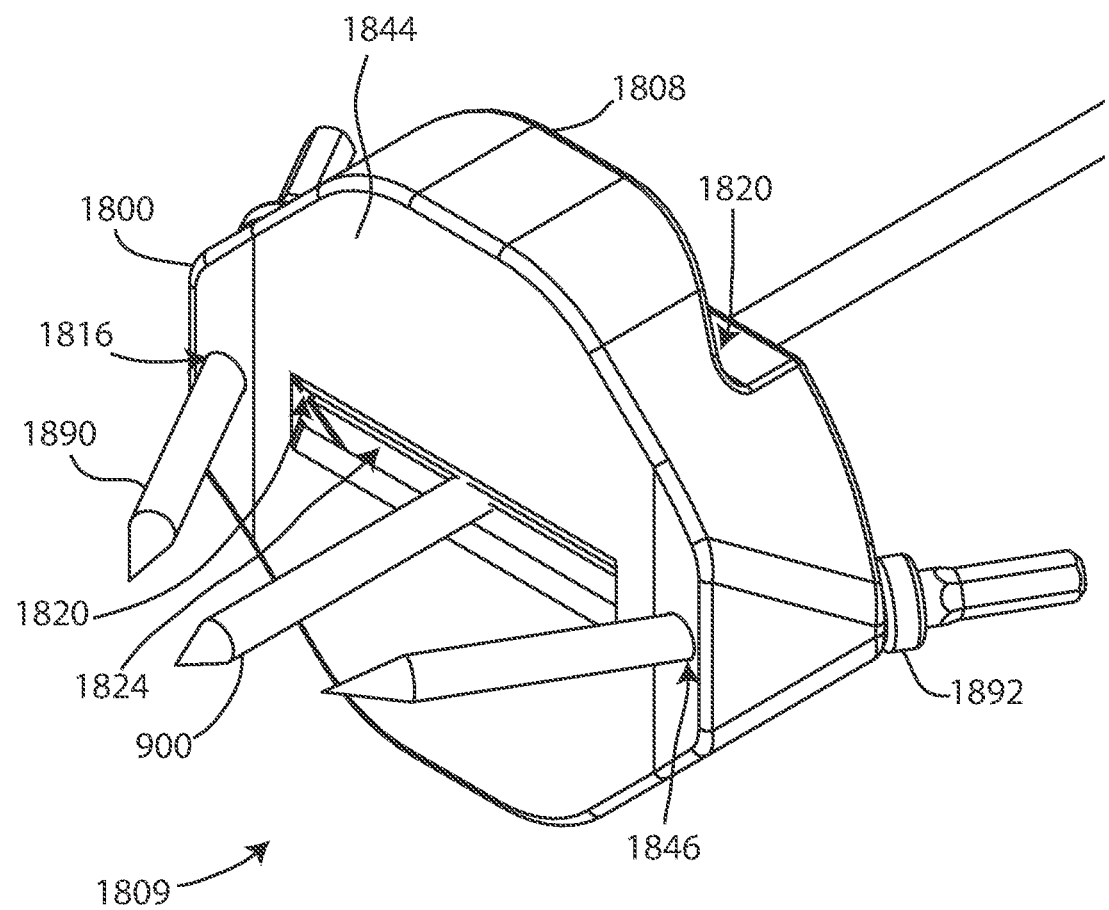
FIG. 13B is another isometric view of the cutting guide, pin, and fasteners of FIG. 13A from a different viewpoint.

Referring to FIGS. 13A-13B, a cutting guide 1800, the pin 900, and two fasteners 1890, 1892 are shown in an operative arrangement. The cutting guide 1800 may be referred to as an anterior-posterior or A-P cutting guide or as a medial-lateral or M-L cutting guide. The cutting guide 1800 may be used to guide a cutting tool, such as a saw blade, to cut two planar bone resections 20, 24 corresponding to planar surfaces 120, 124 of humeral component 100, or the planar surfaces of humeral components 200, 300, 400, 500, 600.

The cutting guide 1800 includes a body 1808 with a bone-facing side 1809. The bone-facing side 1809 includes a planar surface 1844. Two slots 1820, 1824 extend obliquely through the cutting guide 1800, corresponding to the relative arrangement of planar surfaces 120, 124 of humeral component 100, or the planar surfaces of humeral components 200, 300, 400, 500, 600. The slots 1820, 1824 may intersect at the planar surface 1844. One or more holes 1816 may extend through the cutting guide 1800 near opposing apices or ends of the body 1808 to receive fasteners 1890, 1892 to fix the cutting guide 1800 to the humeral head prior to making any bone resections; two converging holes 1816, 1846 are shown. A central hole 1818 may extend through the cutting guide 1800 to receive pin 900.

Referring to FIGS. 14A-14B, a cutting guide 1900 and two fasteners 1990, 1992 are shown in an operative arrangement. The cutting guide 1900 may be referred to as an anterior-posterior or A-P cutting guide or as a medial-lateral or M-L cutting guide. The cutting guide 1900 may be used to guide a cutting tool, such as a saw blade, to cut two planar bone resections 20, 24 corresponding to planar surfaces 120, 124 of humeral component 100, or the planar surfaces of humeral components 200, 300, 400, 500, 600.

The cutting guide 1900 includes a shaft 1902 which extends between a proximal handle 1904 and a distal working portion 1906. The distal working portion 1906 may be releasably or permanently coupled to the shaft 1902. The distal working portion 1906 includes the following features, which may be substantially similar to, or the same as, the corresponding features of the cutting guide 1800: body 1908; bone-facing side 1909; planar surface 1944; slots 1920, 1924; and converging holes 1916, 1946. The slots 1920, 1924 extend obliquely through the cutting guide corresponding to the relative arrangement of planar surfaces 120, 124 of humeral component 100, or the planar surfaces of humeral components 200, 300, 400, 500, 600. The slots 1920, 1924 may intersect at the planar surface 1944. A central socket or hole 1918 may receive shaft 1902.

Figure 15A:
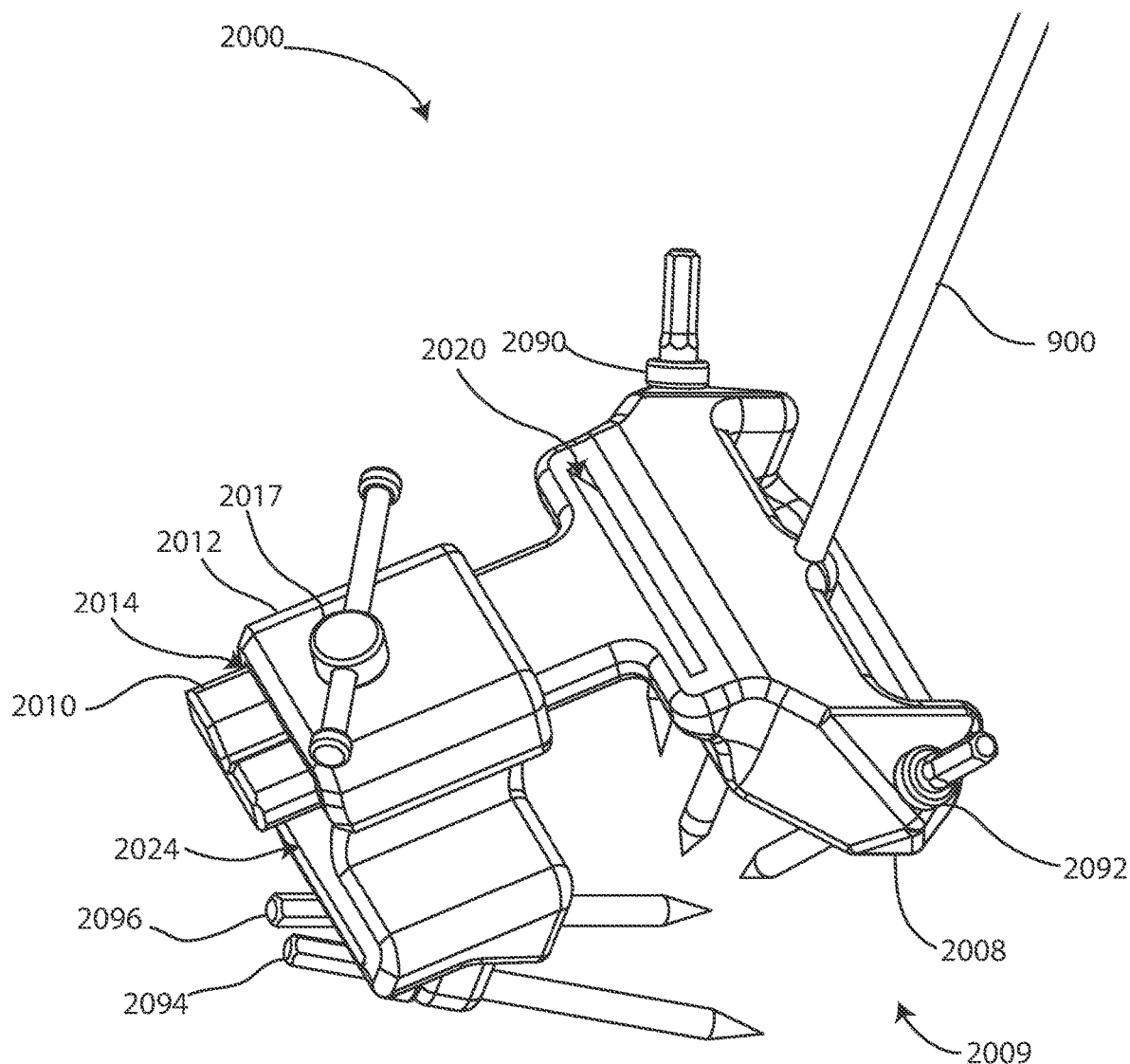
FIG. 15A is an isometric view of yet another cutting guide with the pin of FIG. 9A and four fasteners.
Figure 15B:
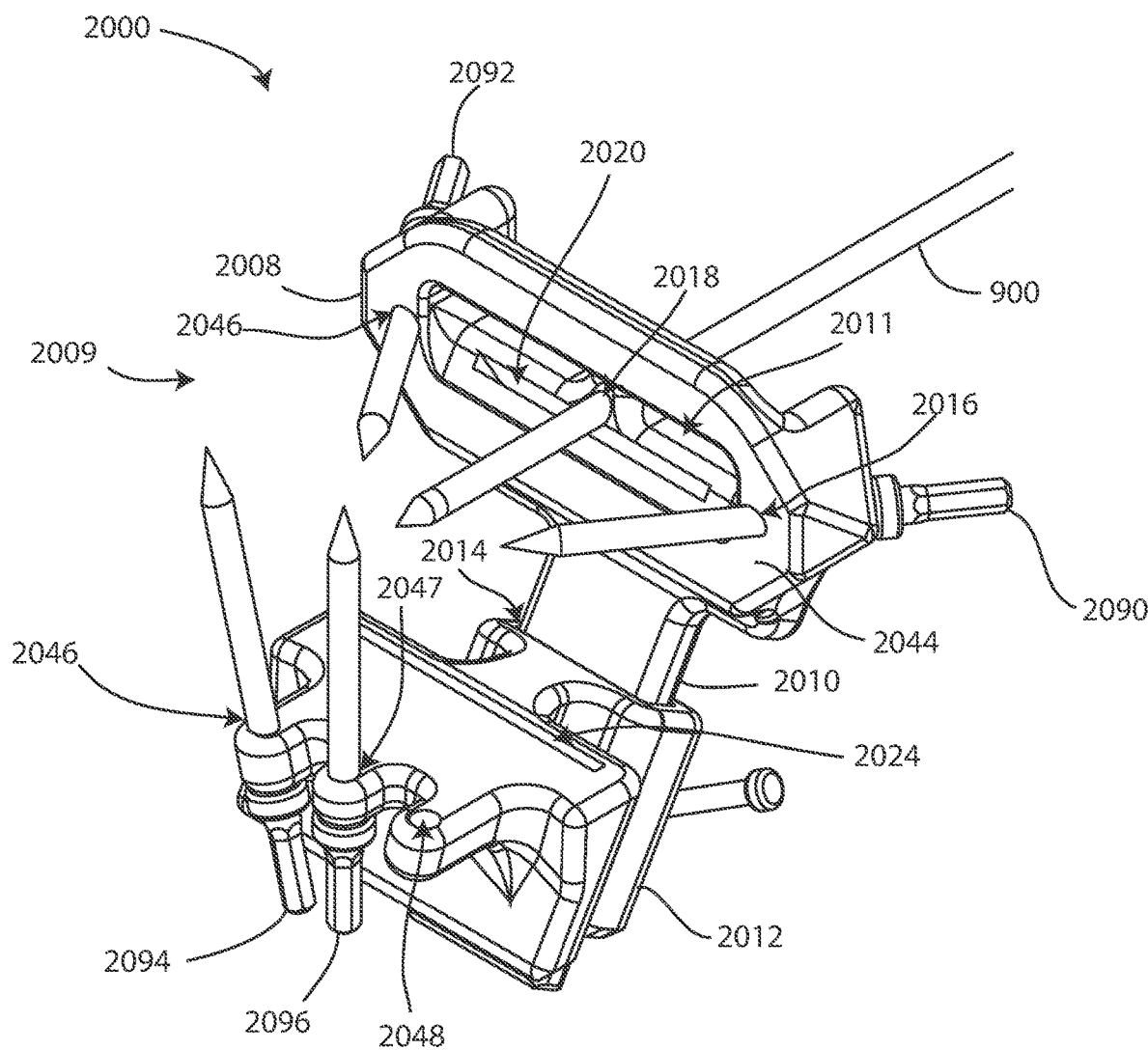
FIG. 15B is another isometric view of the cutting guide, pin, and fasteners of FIG. 15A from a different viewpoint.

Referring to FIGS. 15A-15B, a cutting guide 2000, pin 900, and four fasteners 2090, 2092, 2094, 2096 are shown in an operative arrangement. The cutting guide 2000 may be referred to as a modular anterior-posterior or A-P cutting guide, or as a modular medial-lateral or M-L cutting guide. The cutting guide 2000 may be used to guide a cutting tool, such as a saw blade, to cut two planar bone resections 20, 24 corresponding to planar surfaces 120, 124 of humeral component 100, or the planar surfaces of humeral components 200, 300, 400, 500, 600.

The cutting guide 2000 includes a first body 2008 with a bone-facing side 2009. The bone-facing side 2009 includes a planar surface 2044. A slot 2020 extends obliquely through the first body 2008, corresponding to the planar surface 120 of humeral component 100, or the planar surface of humeral components 200, 300, 400, 500, 600. One or more holes 2016 may extend through the first body 2008 near opposing apices or ends of the body to receive fasteners 2090, 2092 to fix the first body 2008 to the humeral head prior to making any bone resections; two converging holes 2016, 2046 are shown. A central hole 2018 may extend through the first body 2008 to receive pin 900. The first body 2008 includes a protrusion 2010 which extends from the first body next to the slot 2020. The protrusion 2010 may have a rectangular, notched, dovetail, or other cross sectional shape typical of a guide rail. A window 2011 or loop extends from the first body opposite the slot 2020.

The cutting guide 2000 includes a rectangular second body 2012 with a slot 2014 that is complementary to the protrusion 2010 and sized for a clearance fit. The slot 2014 slidingly receives the protrusion 2010. The second body 2012 includes a fastener 2017 which locks the second body to the protrusion 2010 at a desired location. A slot 2024 extends through the second body. When the second body 2012 is operatively assembled to the first body 2008 and the cutting guide 2000 is secured to a humeral head, slot 2024 corresponds to the planar surface 124 of humeral component 100, or the planar surface of humeral components 200, 300, 400, 500, 600. One or more holes 2046 may extend through the second body 2012 to receive fasteners 2094, 2096 to fix the second body to the humerus prior to making any bone resections; three diverging holes 2046, 2047, 2048 are shown.

Figure 16:
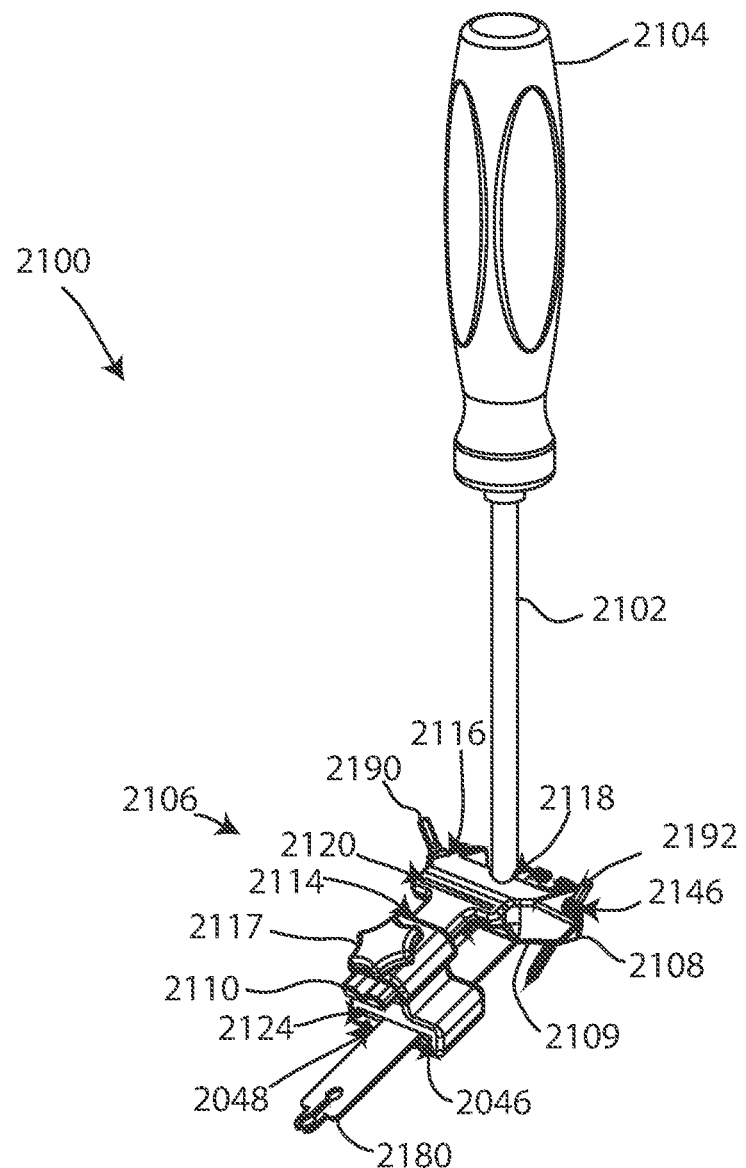
FIG. 16 is an isometric view of yet another cutting guide with two fasteners and a saw blade.

Referring to FIG. 16, a cutting guide 2100, pin 900, and four fasteners 2090, 2092, 2094, 2096 are shown in an operative arrangement. The cutting guide 2100 may be referred to as a modular anterior-posterior or A-P cutting guide or as a modular medial-lateral or M-L cutting guide. The cutting guide 2100 may be used to guide a cutting tool, such as a saw blade, to cut two planar bone resections 20, 24 corresponding to planar surfaces 120, 124 of humeral component 100, or the planar surfaces of humeral components 200, 300, 400, 500, 600.

The cutting guide 2100 includes a shaft 2102 which extends between a proximal handle 2104 and a distal working portion 2106. The working portion 2106 includes a first body 2108 and a rectangular second body 2112. The first body 2108 includes the following features, which may be substantially similar to, or the same as, the corresponding features of the first body 2008: bone-facing side 2109;

planar surface 2144; slot 2120; converging holes 2116, 2146; protrusion 2110; and window 2111 or loop. A central socket or hole 2118 may receive shaft 2102. The second body 2112 includes the following features, which may be substantially similar to, or the same as, the corresponding features of the second body 2012: slot 2114; fastener 2116; slot 2124; holes 2146, 2147, 2148.

Figure 17A:
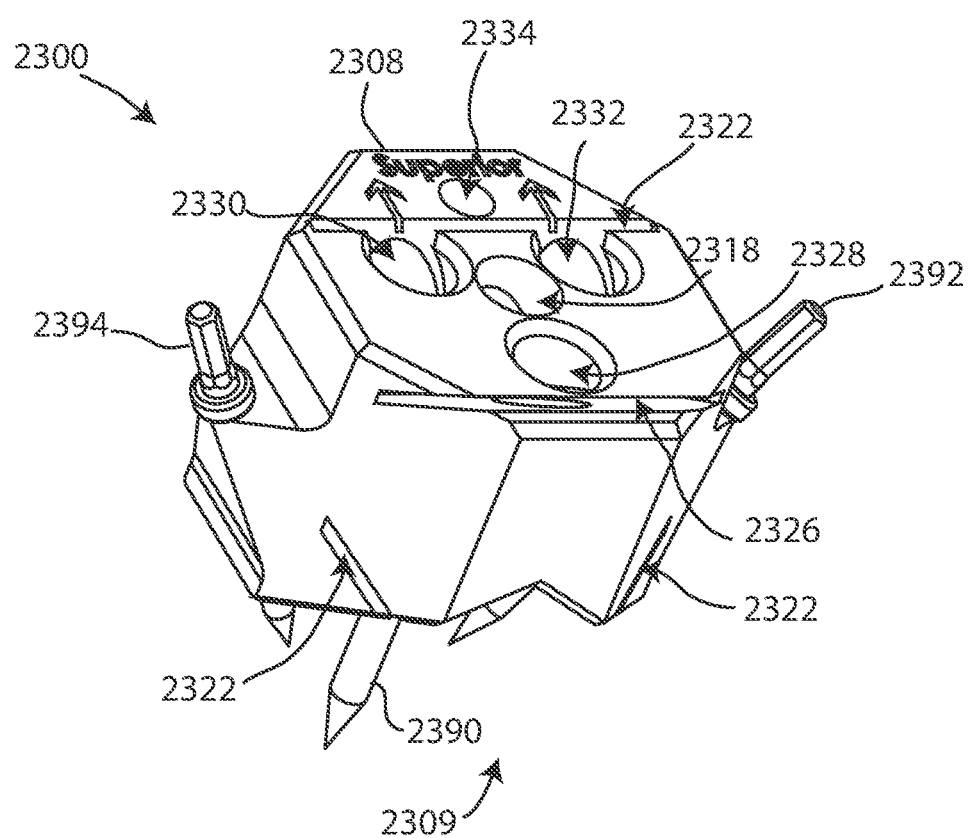
FIG. 17A is an isometric view of yet another cutting guide with three fasteners.
Figure 17B:
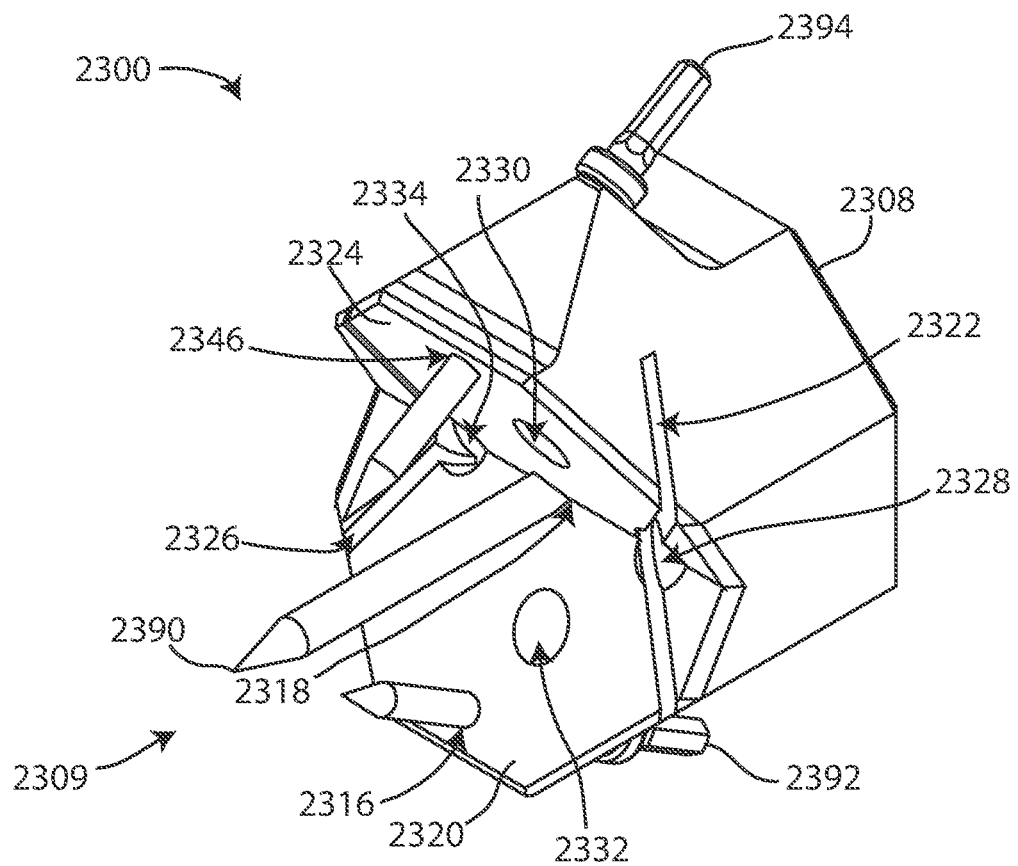
FIG. 17B is another isometric view of the cutting guide and fasteners of FIG. 17A from a different viewpoint.
Figure 17C:
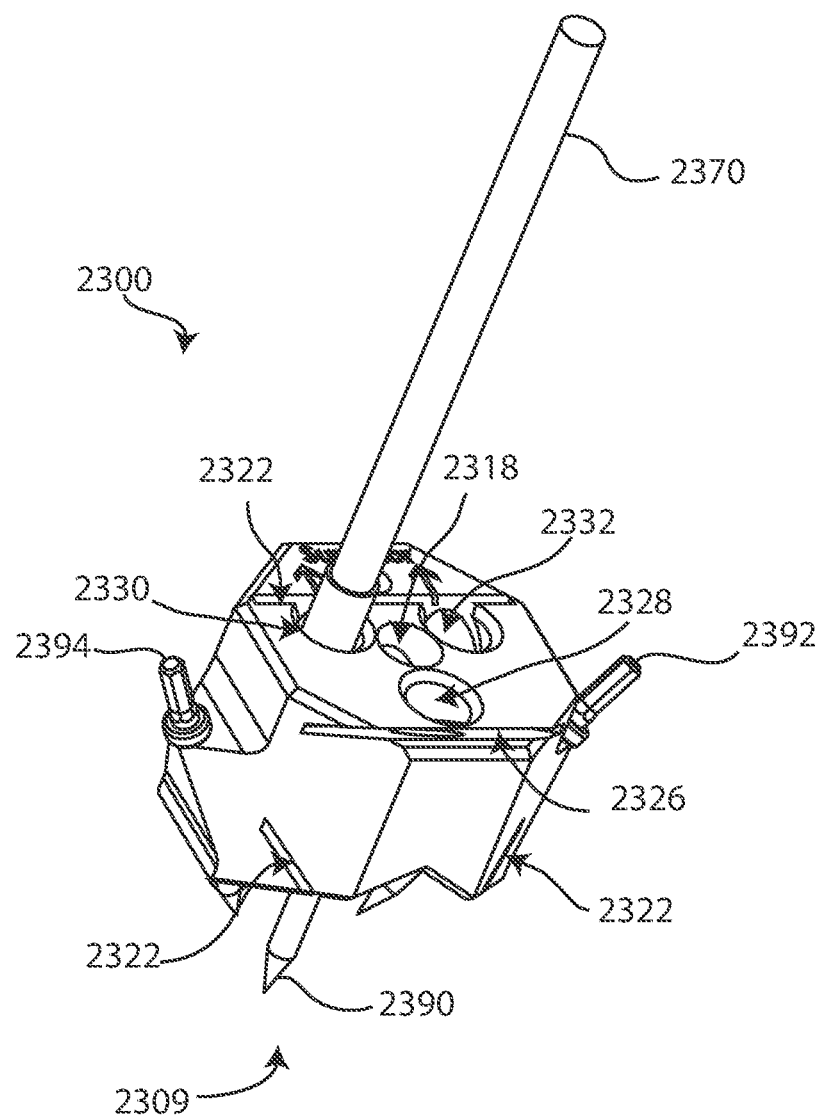
FIG. 17C is another isometric view of the cutting guide and fasteners of FIG. 17A with a drill, from the viewpoint of FIG. 17A.

Referring to FIGS. 17A-17C, a cutting guide 2300 and three fasteners 2390, 2392, 2394 are shown in an operative arrangement. The cutting guide 2300 may be referred to as a cut and drill guide or as a superior-inferior or S-I cutting guide. The cutting guide 2300 may be used to guide a cutting tool, such as a saw blade, to cut two planar bone resections 22, 26 corresponding to planar surfaces 122, 126 of humeral component 100, or the planar surfaces of humeral components 200, 300, 400, 500, 600. The cutting guide 2300 may also be used to guide a cutting tool, such as a drill or reamer, to cut bone holes 28, 30, 32 corresponding to anchoring elements 128, 130, 132 of humeral component 100, or the anchoring elements of humeral components 200, 300, 400, 500, 600.

The cutting guide 2300 includes a body 2308 with a bone-facing side 2309. The bone-facing side 2309 includes intersecting planar surfaces 2320, 2324. Three holes 2328, 2330, 2332 extend lengthwise through the cutting guide 2300, corresponding to the relative arrangement of anchoring elements 128, 130, 132 of humeral component 100, or the anchoring elements of humeral components 200, 300, 400, 500, 600. A fourth hole 2334 may be included in the cutting guide 2300, corresponding to anchoring elements 434, 534, 634. Two slots 2322, 2326 extend obliquely through the cutting guide 2300, corresponding to the relative arrangement of planar surfaces 122, 126 of humeral component 100, or the planar surfaces of humeral components 200, 300, 400, 500, 600. One or more holes 2316 may extend through the cutting guide 2300 near opposing apices or ends of the body 2308 to receive fasteners 2392, 2394 to fix the cutting guide 2300 to the humeral head prior to making any bone resections; two converging holes 2316, 2346 are shown. A central hole 2318 may extend through the cutting guide 2300 to receive fastener 2390. Fastener 2390 may be countersunk or otherwise recessed into the cutting guide 2300 to avoid occluding the slots 2322, 2326. Cutting guide 2300 may be secured by fastener 2390 alone, by fasteners 2392, 2394, by any two of fasteners 2390, 2392, 2394, or by all three fasteners.

Figure 18:
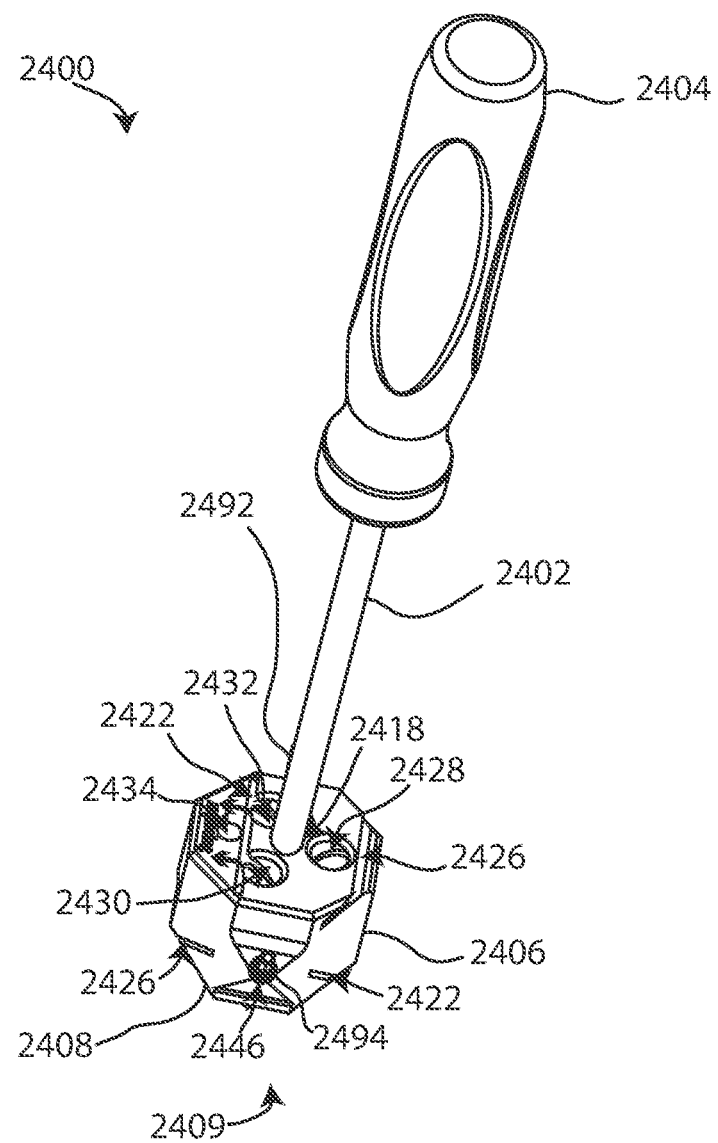
FIG. 18 is an isometric view of yet another cutting guide with two fasteners.

Referring to FIG. 18, a cutting guide 2400 and two fasteners 2492, 2494 are shown in an operative arrangement. The cutting guide 2400 may be referred to as a cut and drill guide or as a superior-inferior or S-I cutting guide. The cutting guide 2400 may be used to guide a cutting tool, such as a saw blade, to cut two planar bone resections 22, 26 corresponding to planar surfaces 122, 126 of humeral component 100, or the planar surfaces of humeral components 200, 300, 400, 500, 600. The cutting guide 2400 may also be used to guide a cutting tool, such as a drill or reamer, to cut bone holes 28, 30, 32 corresponding to anchoring elements 128, 130, 132 of humeral component 100, or the anchoring elements of humeral components 200, 300, 400, 500, 600.

The cutting guide 2400 includes a shaft 2402 which extends between a proximal handle 2404 and a distal working portion 2406. The distal working portion 2406 may be releasably or permanently coupled to the shaft 2402 by threads or by releasable connection mechanisms. The distal working portion 2406 includes the following features, which may be substantially similar to, or the same as, the corresponding features of the cutting guide 2300: body 2408; bone-facing side 2409; intersecting planar surfaces 2420, 2424 (not visible in FIG. 18); holes 2428, 2430, 2432, 2434; slots 2422, 2426; and converging holes 2416, 2446. The slots 2422, 2426 extend obliquely through the cutting guide 2400, corresponding to the relative arrangement of planar surfaces 122, 126 of humeral component 100, or the planar surfaces of humeral components 200, 300, 400, 500, 600. A central socket or hole 2418 may receive shaft 2402.

Figure 19A:
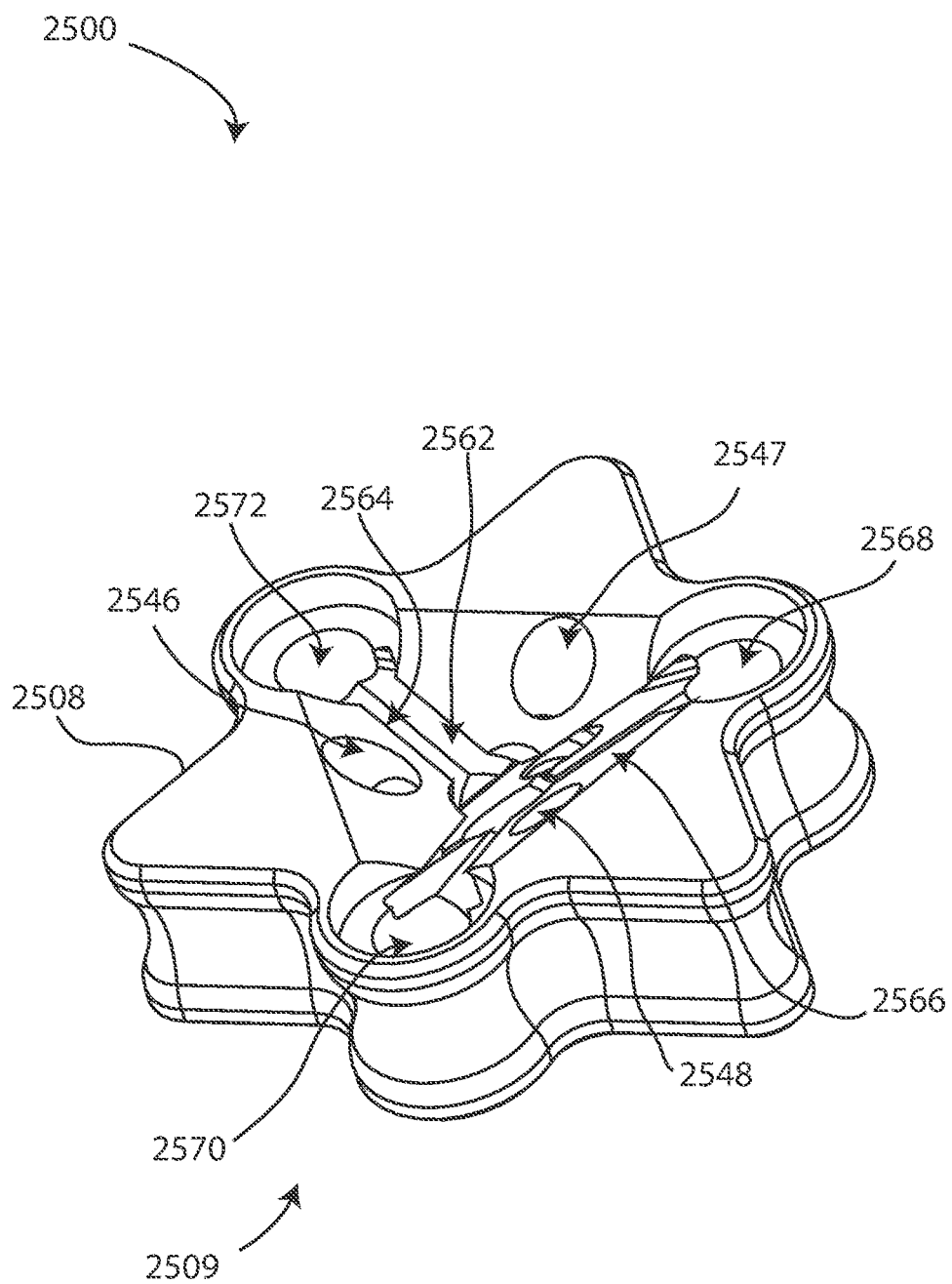
FIG. 19A is an isometric view of yet another cutting guide.
Figure 19B:
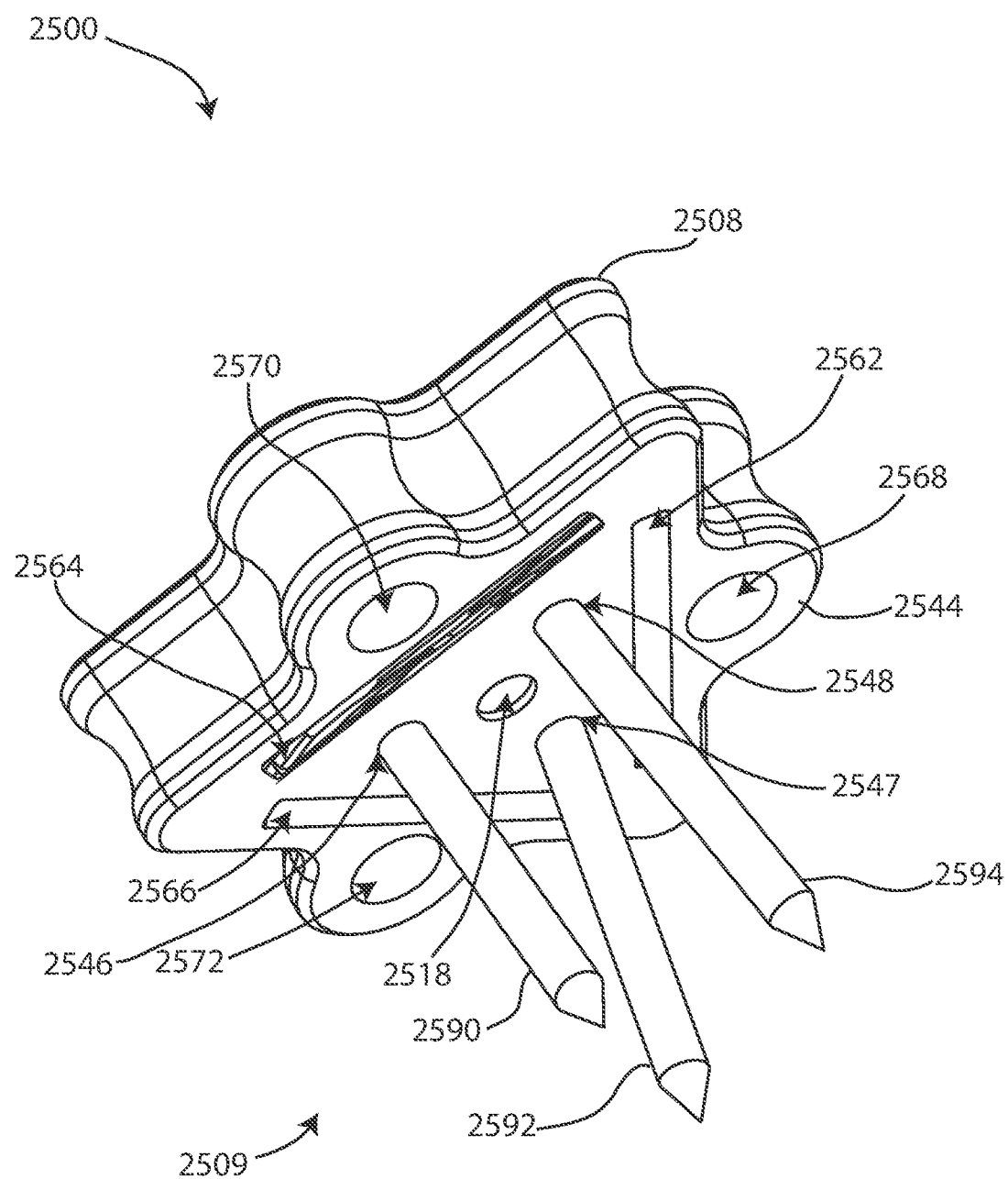
FIG. 19B is another isometric view of the cutting guide of FIG. 19A with three fasteners, from a different viewpoint.

Referring to FIGS. 19A-19B, a cutting guide 2500 and three fasteners 2590, 2592, 2594 are shown in FIG. 19B in an operative arrangement. The cutting guide 2500 may be referred to as a cut and drill guide. The cutting guide 2500 may be used to guide a cutting tool, such as a saw blade, to cut three planar bone resections 62, 64, 66 corresponding to planar surfaces 762, 764, 766 of humeral component 700, or planar surfaces 862, 864, 866 of humeral component 800. The cutting guide 2500 may also be used to guide a cutting tool, such as a drill or reamer, to cut bone holes 68, 70, 72 corresponding to anchoring elements 768, 770, 772 of humeral component 700, or anchoring elements 868, 870, 872 of humeral component 800.

The cutting guide 2500 includes a star-shaped body 2508 with a bone-facing side 2509 which includes a planar surface 2544. Three holes 2568, 2570, 2572 extend lengthwise through the cutting guide 2500, corresponding to the relative arrangement of anchoring elements 768, 770, 772 of humeral component 700, or anchoring elements 868, 870, 872 of humeral component 800. Three slots 2562, 2564, 2566 extend obliquely through the cutting guide 2500, corresponding to the relative arrangement of planar surfaces 762, 764, 766 of humeral component 700, or planar surfaces 862, 864, 866 of humeral component 800. One or more holes 2516 may extend through a central portion of the cutting guide 2500 to receive fasteners 2590, 2592, 2594 to fix the cutting guide 2500 to the humeral head prior to making any bone resections or holes; three skew holes 2546, 2547, 2548 are shown. The fasteners 2590, 2592, 2594 may be countersunk or otherwise recessed into the cutting guide 2500 to avoid occluding the slots 2562, 2564, 2566. A central hole 2518 may extend through the cutting guide 1800 to receive pin 900.

Figure 20A:
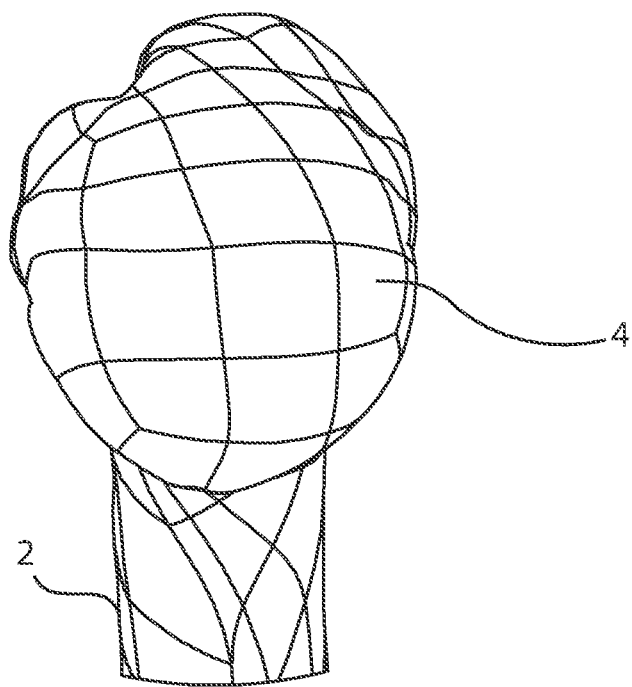
FIG. 20A is an isometric view of an intact proximal humerus along the humeral neck axis.
Figure 20B:
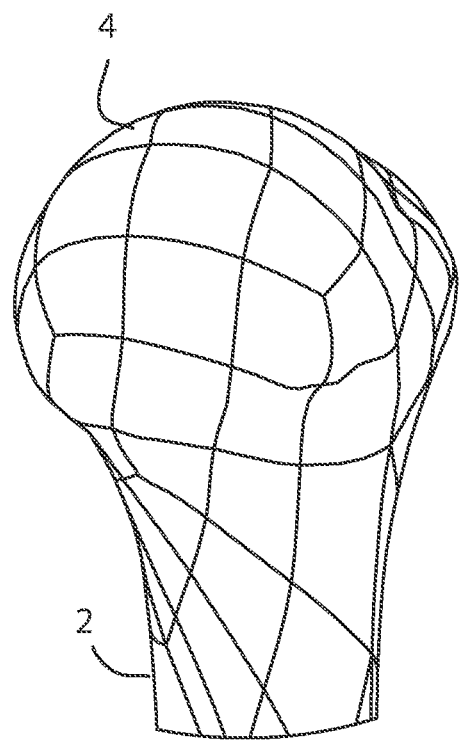
FIG. 20B is an isometric view of the proximal humerus of FIG. 20A from a postero-medial viewpoint.
Figure 21A:
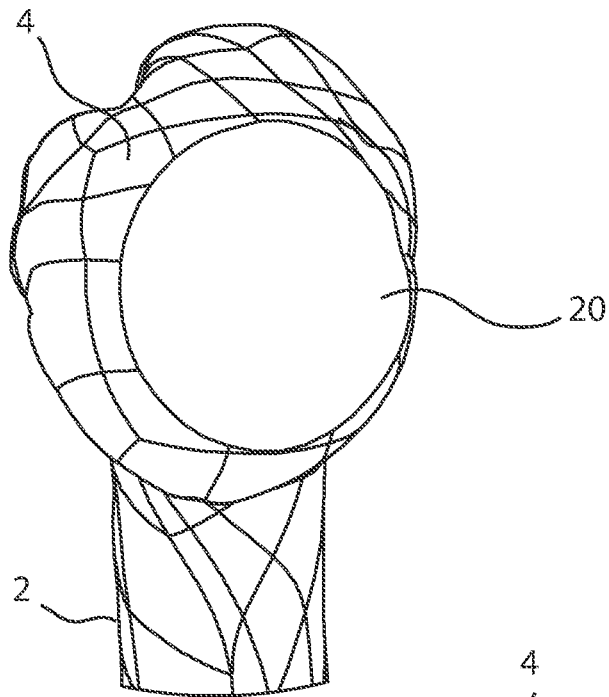
FIG. 21A is an isometric view of the proximal humerus of FIG. 20A along the humeral neck axis after a posterior bone resection has been made.
Figure 21B:
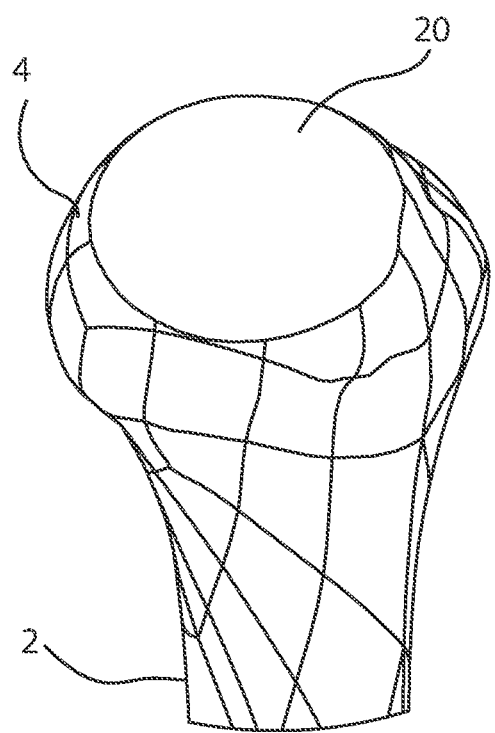
FIG. 21B is an isometric view of the proximal humerus of FIG. 21A from a postero-medial viewpoint.
Figure 22A:
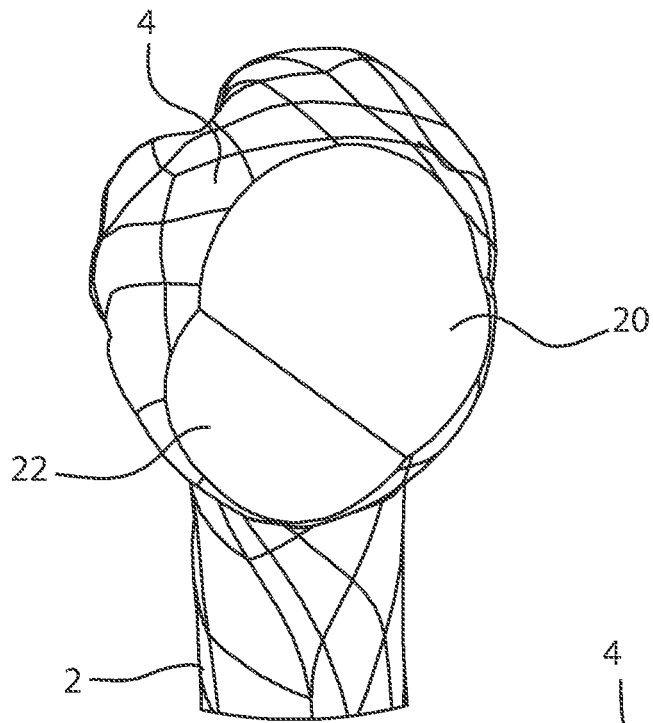
FIG. 22A is an isometric view of the proximal humerus of FIG. 21A along the humeral neck axis after an inferior bone resection has been made.
Figure 22B:
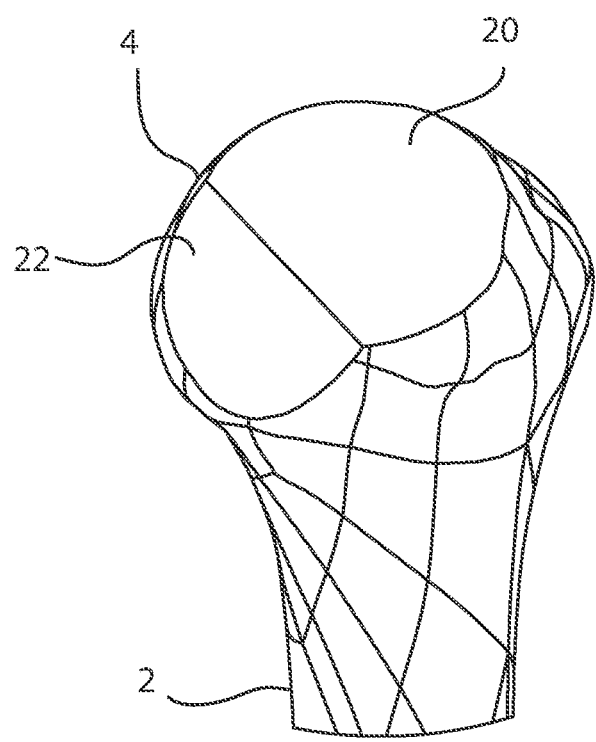
FIG. 22B is an isometric view of the proximal humerus of FIG. 22A from a postero-medial viewpoint.
Figure 23A:
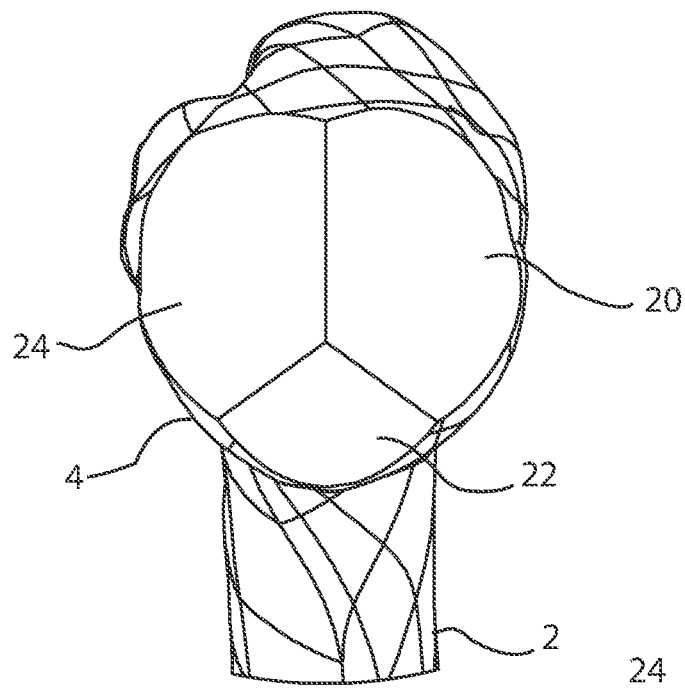
FIG. 23A is an isometric view of the proximal humerus of FIG. 22A along the humeral neck axis after an anterior bone resection has been made.
Figure 23B:
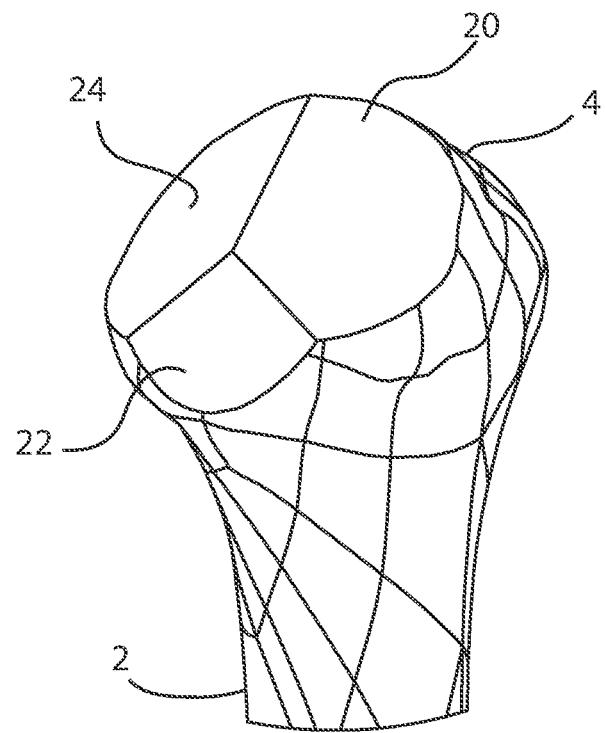
FIG. 23B is an isometric view of the proximal humerus of FIG. 23A from a postero-medial viewpoint.
Figure 24A:
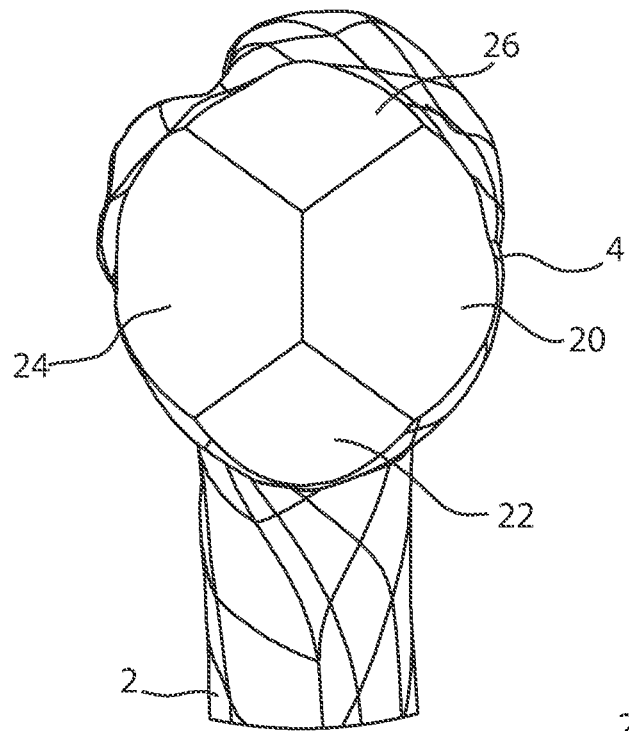
FIG. 24A is an isometric view of the proximal humerus of FIG. 23A along the humeral neck axis after a superior bone resection has been made.
Figure 24B:
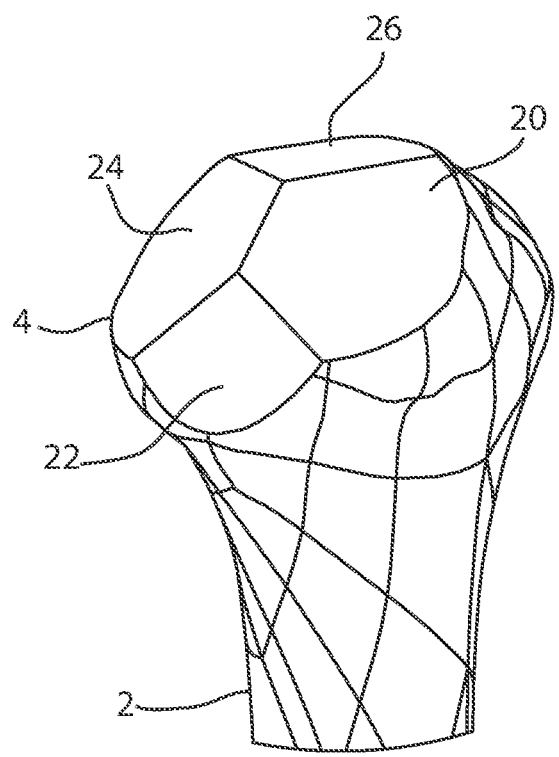
FIG. 24B is an isometric view of the proximal humerus of FIG. 24A from a postero-medial viewpoint.
Figure 25A:
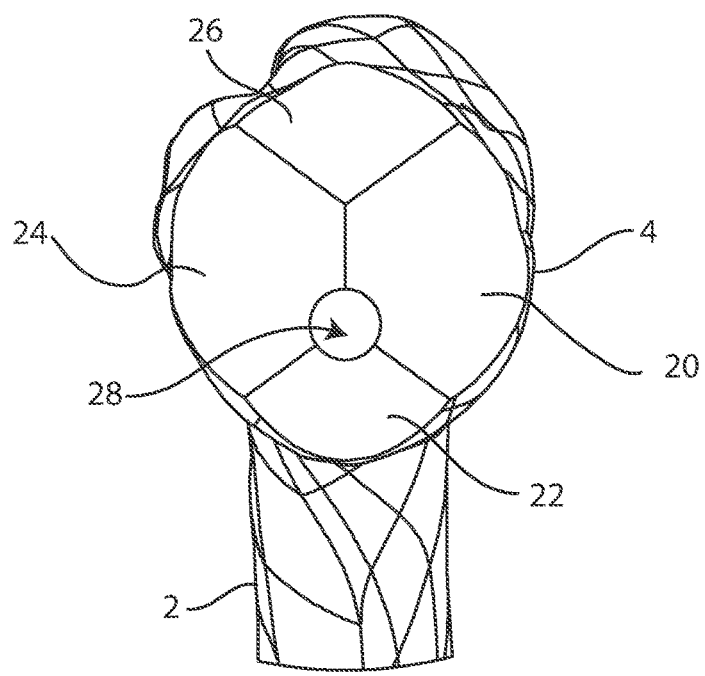
FIG. 25A is an isometric view of the proximal humerus of FIG. 24A along the humeral neck axis after an inferior bone hole has been made.
Figure 25B:
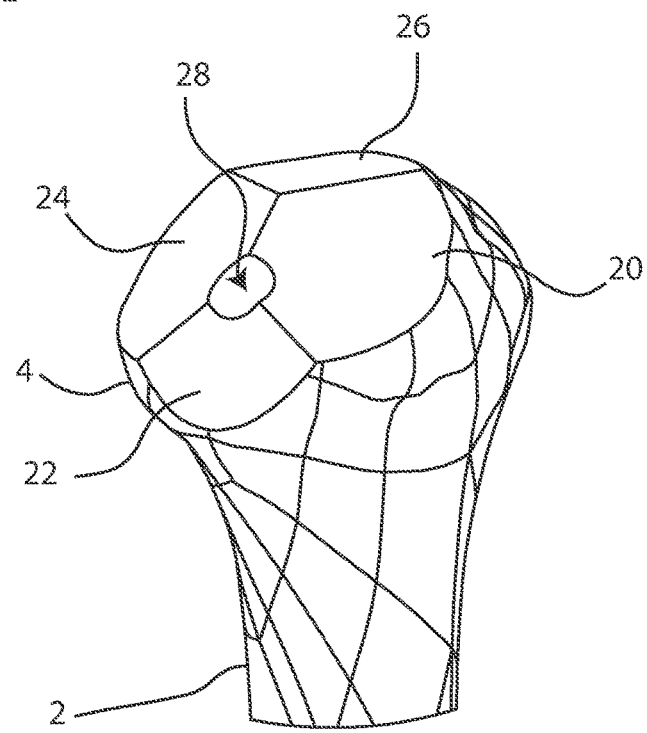
FIG. 25B is an isometric view of the proximal humerus of FIG. 25A from a postero-medial viewpoint.
Figure 26A:
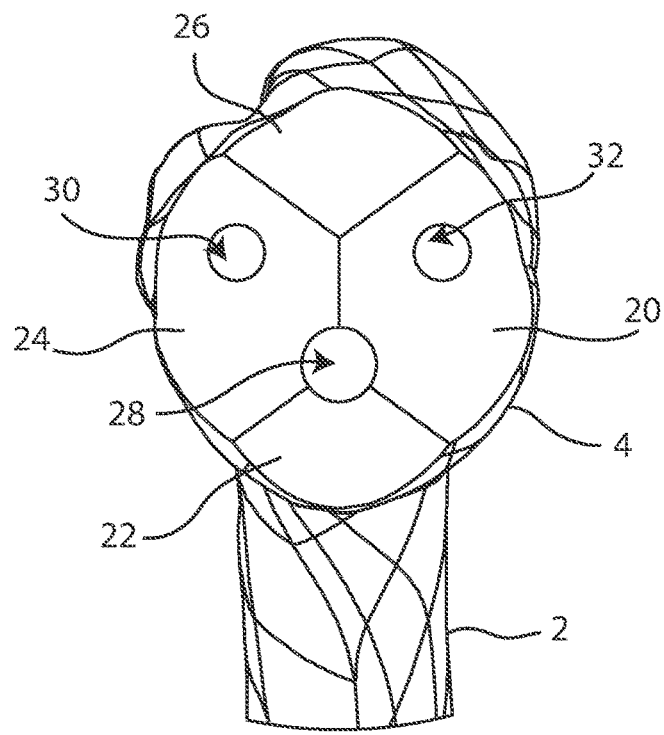
FIG. 26A is an isometric view of the proximal humerus of FIG. 25A along the humeral neck axis after anterior and posterior bone holes have been made.
Figure 26B:
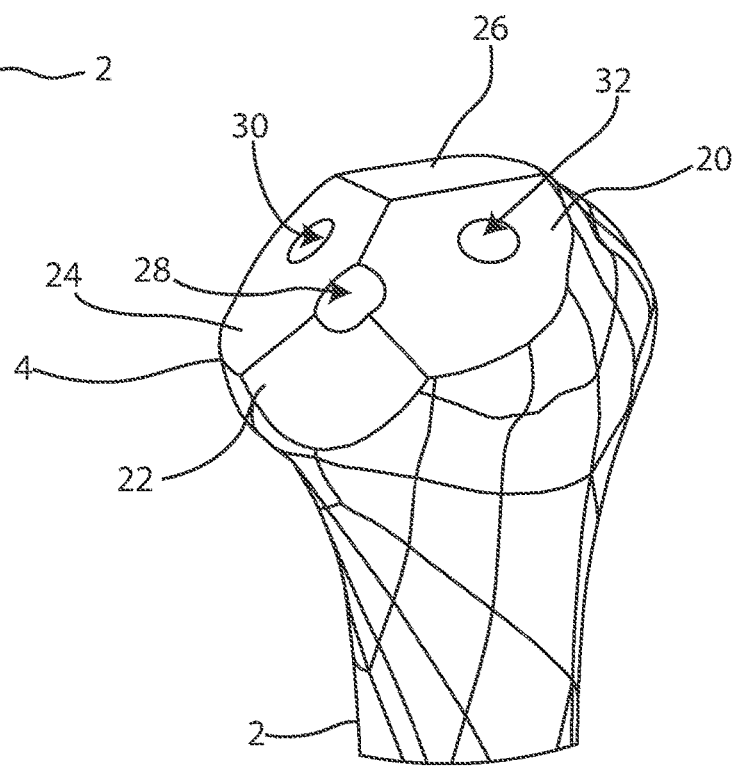
FIG. 26B is an isometric view of the proximal humerus of FIG. 26A from a postero-medial viewpoint.
Figure 42:
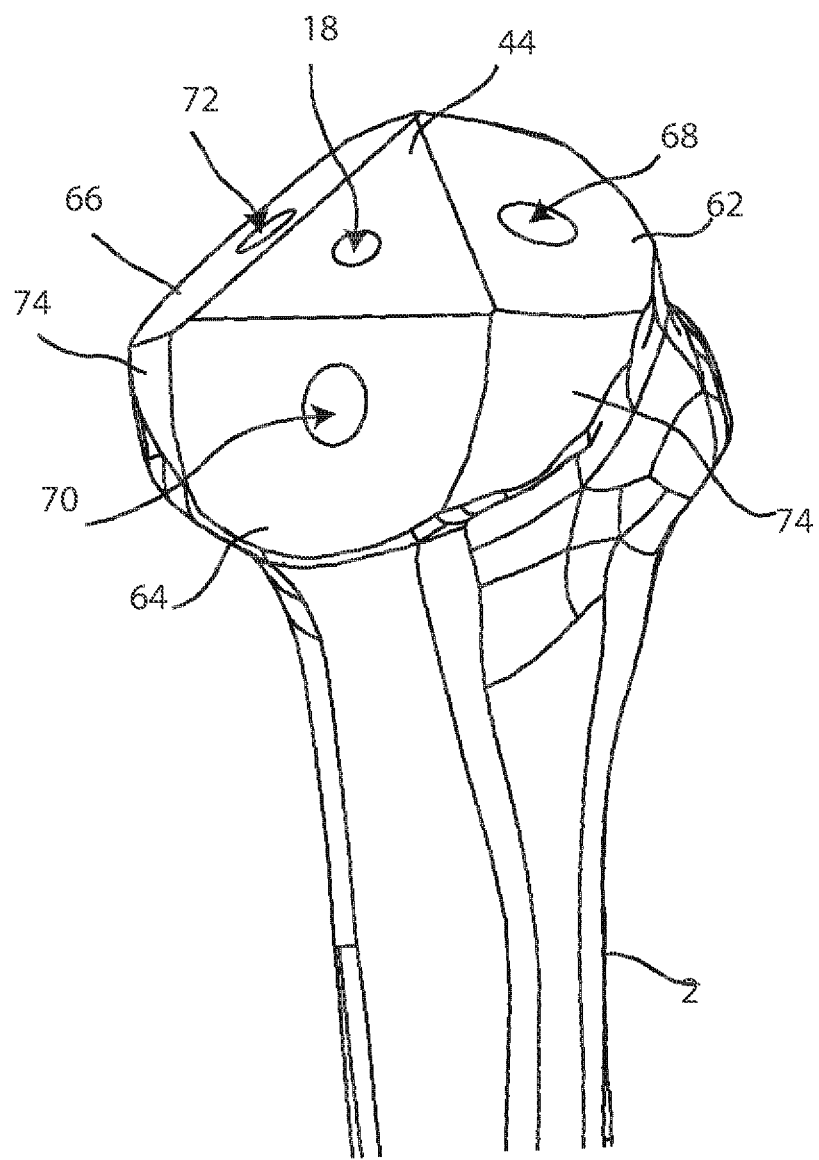
FIG. 42 is an isometric view of the proximal humerus of FIG. 41, after a conical resection has been made.

Referring to FIGS. 20A-20B, a proximal humerus 2 includes a humeral head 4. Referring to FIGS. 21A-26B, a method of preparing a proximal humerus for implantation of a humeral component 100, 200, 300, 400, 500, 600 may include some or all of the steps of cutting a first planar bone resection 20 to remove a posterior aspect of the humeral head 4; cutting a second planar bone resection 22 to remove an inferior aspect of the humeral head 4; cutting a third planar bone resection 24 to remove an anterior aspect of the humeral head 4; cutting a fourth planar bone resection 26 to remove a superior aspect of the humeral head 4; cutting a first bone hole 28 in an inferior aspect of the humeral head 4; cutting second bone hole 30 in an anterior aspect of the humeral head 4; cutting a third bone hole 32 in a posterior aspect of the humeral head 4; and cutting a conical bone resection 74 on the humeral head 4 (as shown in FIG. 42). The steps may be performed in any order, and additional steps may be performed.

With continued reference to FIGS. 21A-26B, with brief reference to FIGS. 12A-12J, another method of preparing a proximal humerus for implantation of a humeral component 100, 200, 300, 400, 500, 600 may include some or all of the steps of placing the bone-facing side 1609 of the cutting guide 1600 against an intact humeral head 4; aligning the cutting guide 1600 in a desired orientation relative to the intact proximal humeral anatomy so that the projections 1656, 1657, 1658 contact the humeral head; securing the cutting guide 1600 to the proximal humerus by driving at least one pin through any of the holes 1616, 1646, 1647, 1648, 1649, 1650, 1651, 1652, 1653, 1654; cutting four planar bone resections 20, 22, 24, 26 by actuating a saw through each slot 1620, 1622, 1624, 1626; cutting three bone holes 28, 30, 32 by actuating a drill through each hole 1628, 1630, 1632; removing the pins, the cutting guide 1600, and bone fragments or debris; and optionally cutting a conical bone resection 74 with conical reamer 1500.

Additional methods of preparing a proximal humerus for implantation of a humeral component may include some or all of the steps of establishing a humeral head axis; cutting anterior and posterior planar bone resections; cutting superior and inferior planar bone resections; and cutting bone holes. Each step is described below as a separate method.

Figure 27:
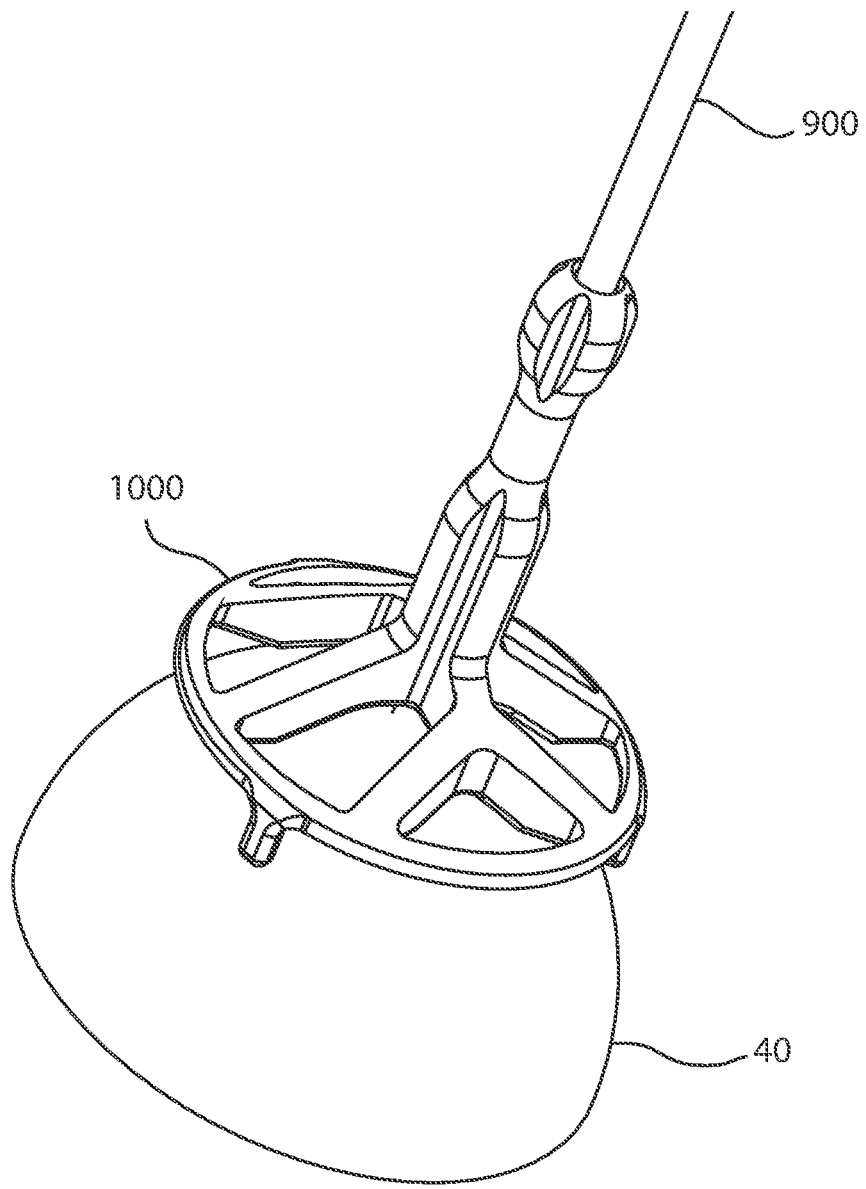
FIG. 27 is an isometric view of the template and pin of FIG. 9A operatively arranged relative to a simplified humeral head represented by a hemisphere.
Figure 29:
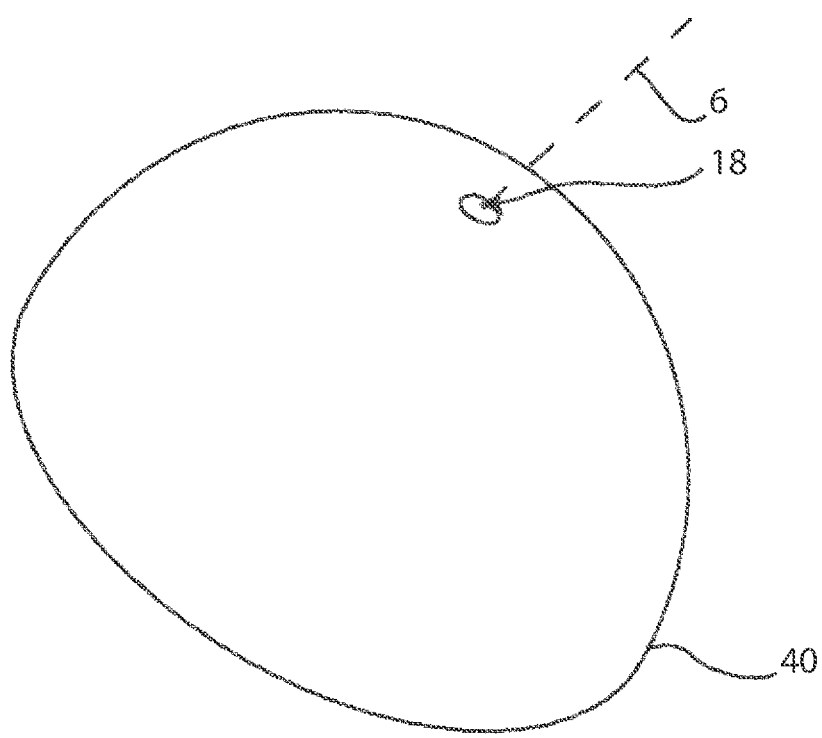
FIG. 29 is an isometric view of the simplified humeral head of FIG. 27 after a central pin hole has been made.

Referring to FIGS. 27-29, with brief reference to FIGS. 9A-9B, a method of establishing a humeral head axis 6 may include some or all of the steps of placing the bone-facing side 1020 of the template 1000 against an intact humeral head 40, which is shown in simplified form as a hemisphere; aligning the humeral shaft extension 1112 of the alignment guide 1100 with the humeral shaft; aligning the articular bar 1114 of the alignment guide 1100 with the articular margin of the humeral head 40; aligning the template 1000 in a desired orientation relative to the intact proximal humeral anatomy so that the projections 1024, 1026, 1028 contact the humeral head 40, wherein aligning the template 1000 may include aligning the shaft 1002 parallel with the post 1116; driving the pin 900 through the cannulation 1030 and into the humeral head 40; and removing the template 1000 and alignment guide 1100. FIG. 29 shows the simplified humeral head 40 with a central bone hole 18 created by driving the pin 900 into the humeral head 40. The humeral head axis 6 is the central longitudinal axis of the hole 18, and may be normal to a central portion of the intact articular surface of the humeral head 40, or parallel to the humeral neck axis.

Figure 30:
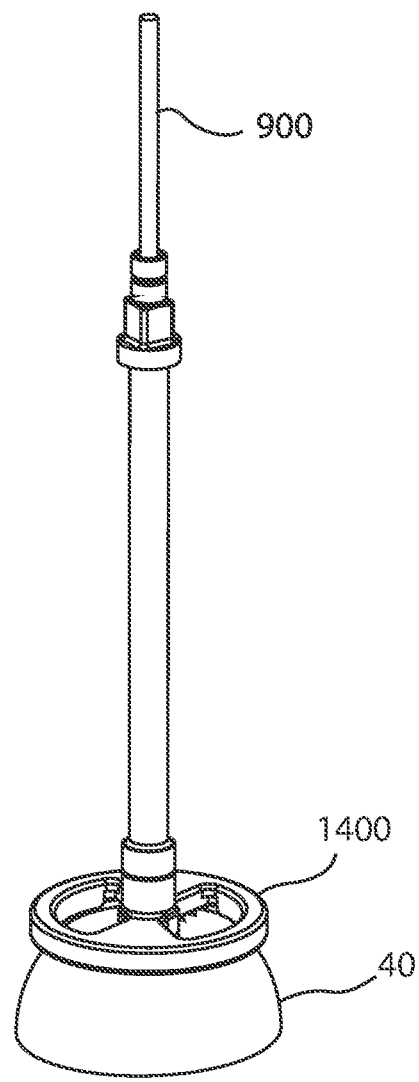
FIG. 30 is an isometric view of the planar reamer and pin of FIG. 10A operatively arranged relative to the simplified humeral head of FIG. 29.
Figure 31:
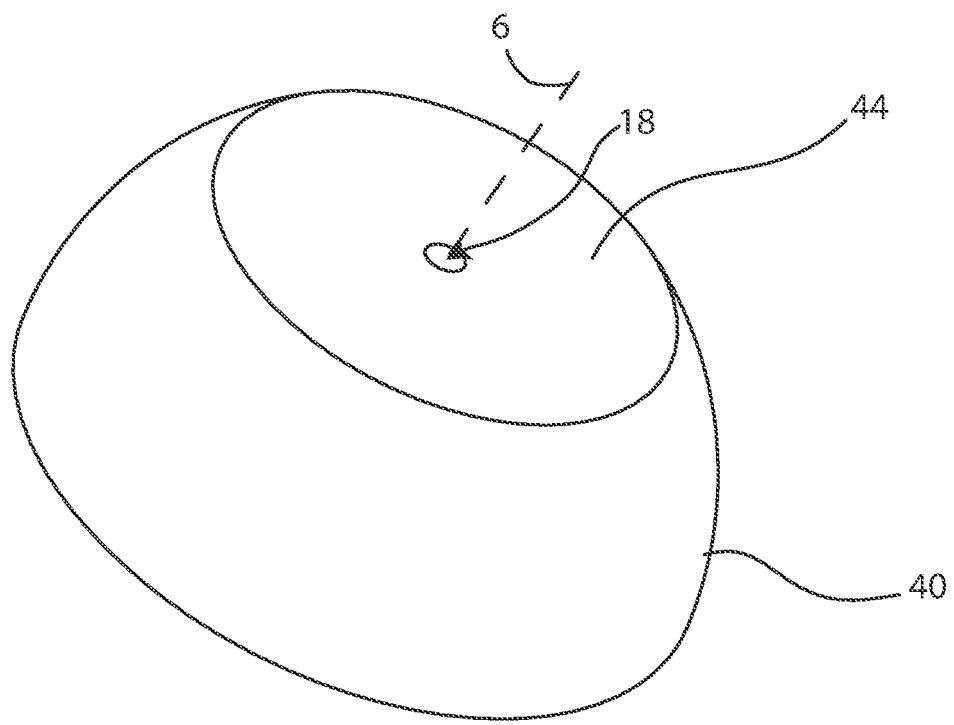
FIG. 31 is an isometric view of the simplified humeral head of FIG. 30 after a planar bone resection has been made perpendicular to the pin hole.

Referring to FIGS. 30 and 31, with brief reference to FIGS. 10A-10B, a method of cutting a planar bone resection 44 may occur after the method of establishing the humeral head axis 6, and may include some or all of the steps of inserting the pin 900 into the cannulation 1430 of the planar reamer 1400; advancing the planar reamer 1400 over the pin 900 to contact the humeral head 40; cutting the planar bone resection 44 by actuating the planar reamer 1400 until the continuous smooth planar surface 1434, or the inner edge 1436 of the surface, contacts the humeral head to stop further bone removal by the planar reamer 1400; and removing the planar reamer. FIG. 31 shows the simplified humeral head 40 with the planar bone resection 44 around the bone hole 18. The planar bone resection 44 is normal to the humeral head axis 6.

Figure 14:
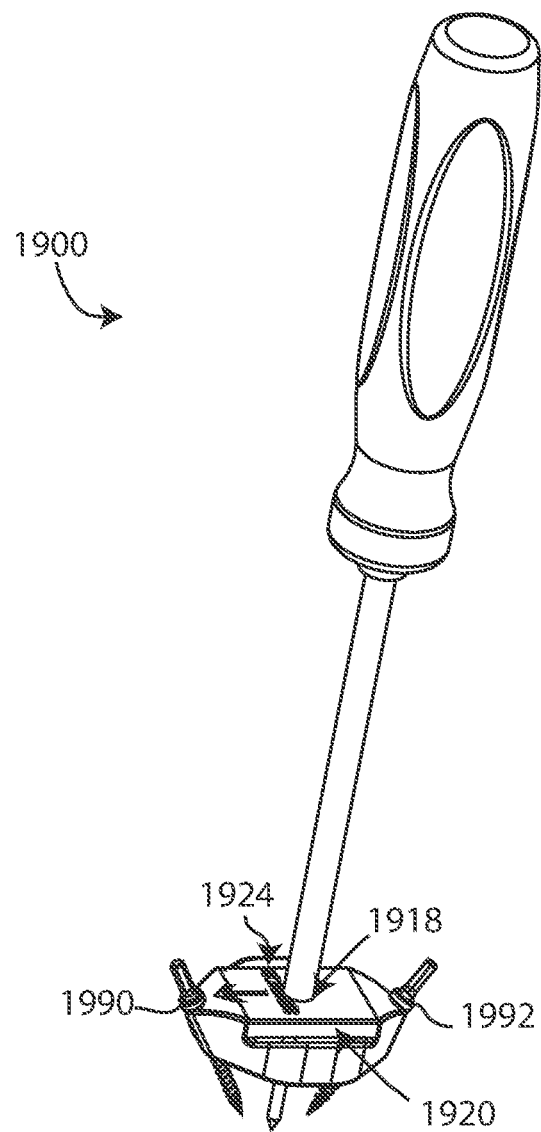
FIG. 14 is an isometric view of yet another cutting guide with two fasteners.
Figure 32:
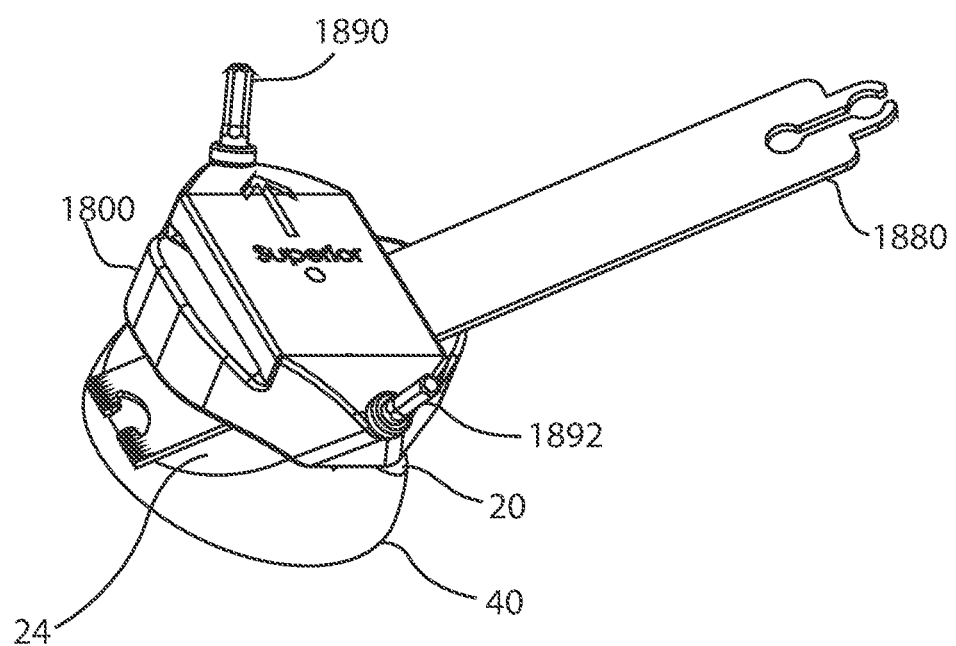
FIG. 32 is an isometric view of the cutting guide and fasteners of FIG. 13A and a saw blade operatively arranged relative to the simplified humeral head of FIG. 31.
Figure 35:
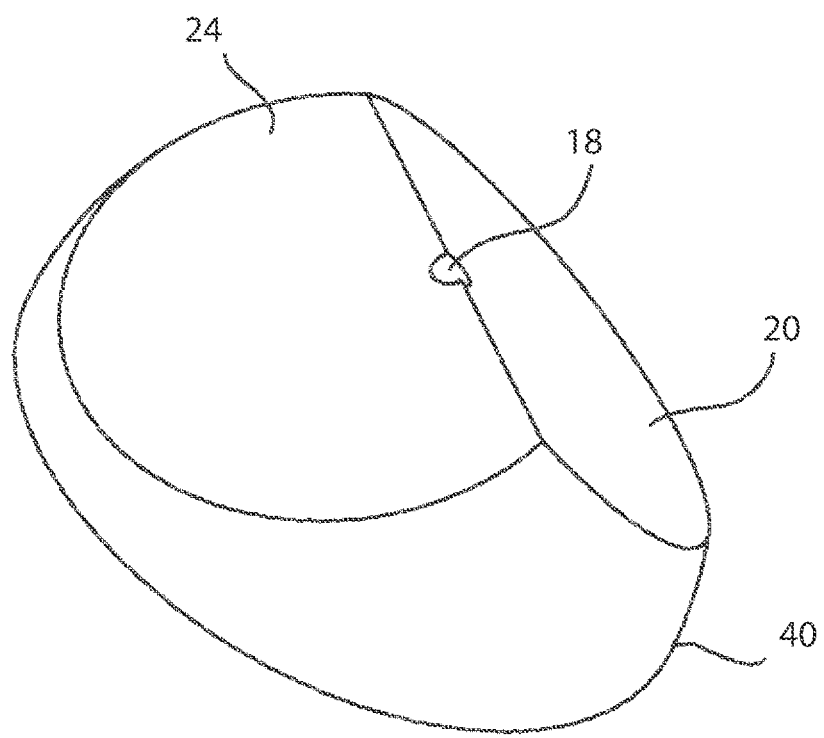
FIG. 35 is an isometric view of the simplified humeral head of FIG. 32 after anterior and posterior bone resections have been made.

Referring to FIGS. 32 and 35, with brief reference to FIGS. 13A-14, a method of cutting anterior and posterior planar bone resections 20, 24 may occur after the method of cutting the planar bone resection 44, and may include some or all of the steps of inserting the pin 900 into the central hole 1818 of the cutting guide 1800; advancing the cutting guide 1800 over the pin 900 to contact the humeral head 40, wherein the planar surface 1844 contacts the planar bone resection 44; securing the cutting guide 1800 to the humeral head 40 by driving at least one fastener 1890, 1892 through any of the holes 1816, 1846; removing the pin 900; cutting two planar bone resections 20, 24 by actuating a saw through each slot 1820, 1824; and removing the fastener(s) 1890, 1892 and the cutting guide 1800. FIG. 35 shows the simplified humeral head 40 with the planar bone resections 20, 24. Cutting guide 1800 may be replaced by cutting guide 1900 in this method, in which case the shaft 1902 and handle 1904 may be used to push the distal working portion 1906 against the humeral head 40 for added stability during one or more of the steps of securing the cutting guide 1900 to the humeral head 40; removing the pin 900; and cutting two planar bone resections 20, 24.

Figure 33:
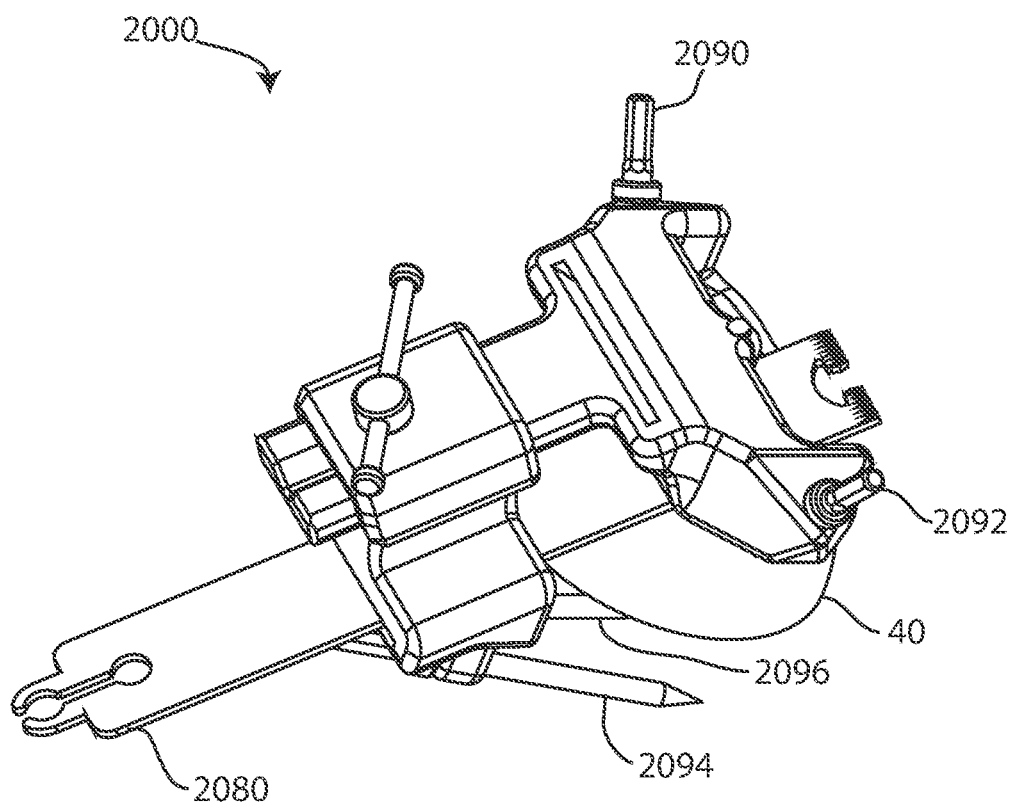
FIG. 33 is an isometric view of the cutting guide and fasteners of FIG. 15A and a saw blade operatively arranged relative to the simplified humeral head of FIG. 31.
Figure 34:
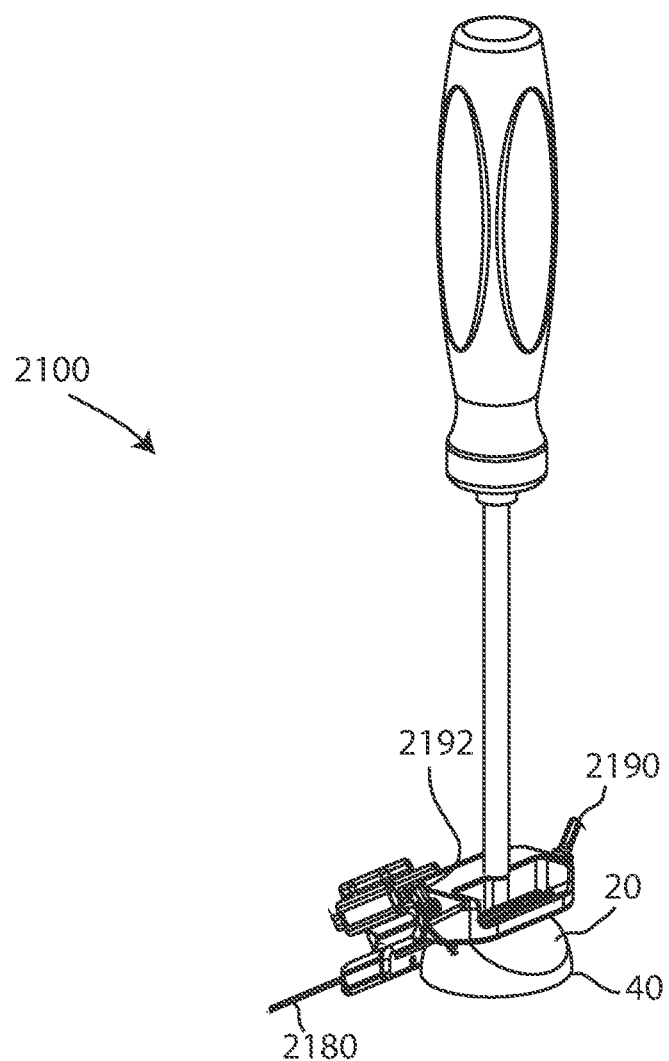
FIG. 34 is an isometric view of the cutting guide and fasteners of FIG. 16 and a saw blade operatively arranged relative to the simplified humeral head of FIG. 31.

Referring to FIGS. 33-35, with brief reference to FIGS. 15A-16, another method of cutting anterior and posterior planar bone resections 20, 24 may occur after the method of cutting the planar bone resection 44, and may include some or all of the steps of inserting the pin 900 into the central hole 2018 of the first body 2008 of the cutting guide 2000; advancing the first body 2008 over the pin 900 to contact the humeral head 40, wherein the planar surface 2044 contacts the planar bone resection 44; securing the first body 2008 to the humeral head 40 by driving at least one fastener 2090, 2092 through any of the holes 2016, 2046; removing the pin 900; inserting the protrusion 2010 into the slot 2014 of the second body 2012; advancing the second body 2012 over the protrusion 2010 to contact the humeral head 40; securing the second body 2012 to the protrusion 2010 by actuating the fastener 2017; securing the second body 2012 to the humeral head by driving at least one fastener 2094, 2096 through any of the holes 2046, 2047, 2048; cutting two planar bone resections 20, 24 by actuating a saw through each slot 2020, 2024; and removing the fastener(s) 2090, 2092, 2094, 2096 and the cutting guide 2000. FIG. 35 shows the simplified humeral head 40 with the planar bone resections 20, 24. Cutting guide 2000 may be replaced by cutting guide 2100 in this method, in which case the shaft 2102 and handle 2104 may be used to push the first body 2008 against the humeral head 40 for added stability during one or more of the steps of securing the first body 2108 to the humeral head 40; removing the pin 900; inserting the protrusion 2110 into the slot 2114 of the second body 2112; advancing the second body 2112 over the protrusion 2110 to contact the humeral head 40; securing the second body 2112 to the protrusion 2110; securing the second body 2112 to the humeral head; and cutting two planar bone resections 20, 24.

Figure 36:
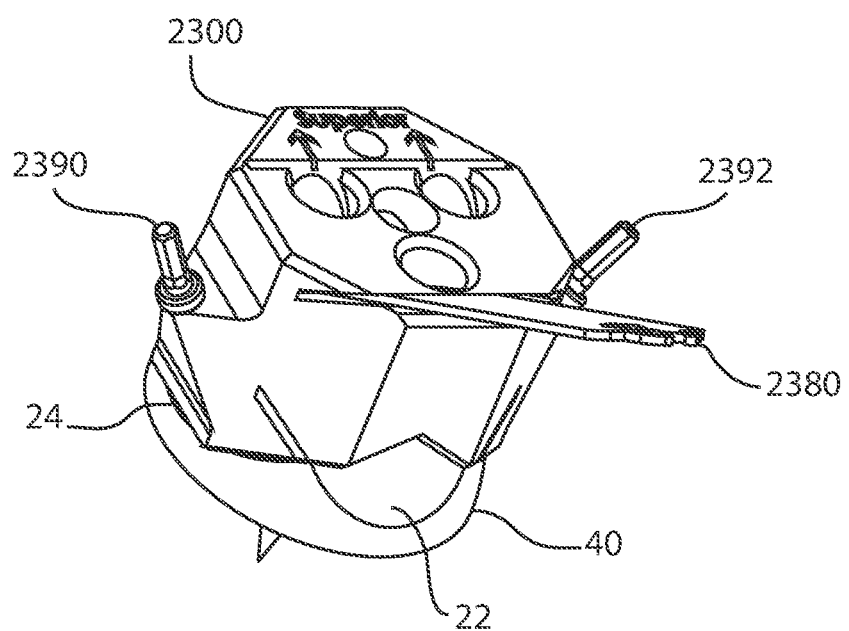
FIG. 36 is an isometric view of the cutting guide and fasteners of FIG. 17A and a saw blade operatively arranged relative to the simplified humeral head of FIG. 35.
Figure 37:
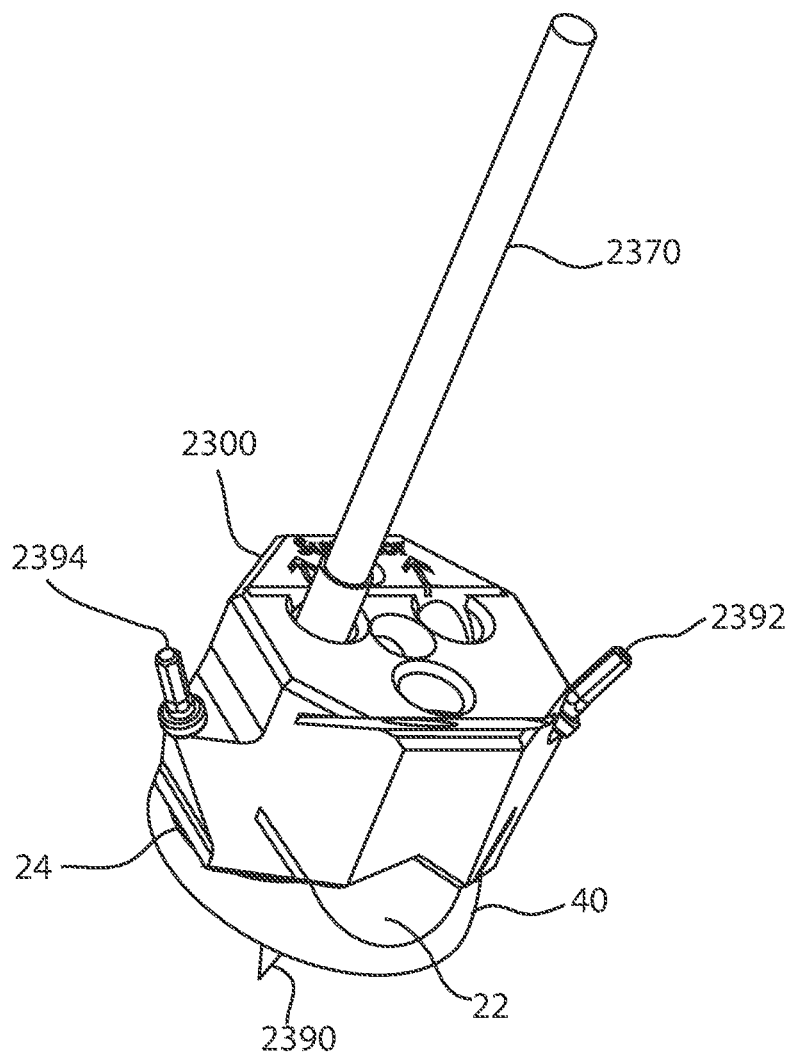
FIG. 37 is an isometric view of the cutting guide, fasteners, and simplified humeral head of FIG. 36 operatively arranged relative to the drill of FIG. 17C.
Figure 38:
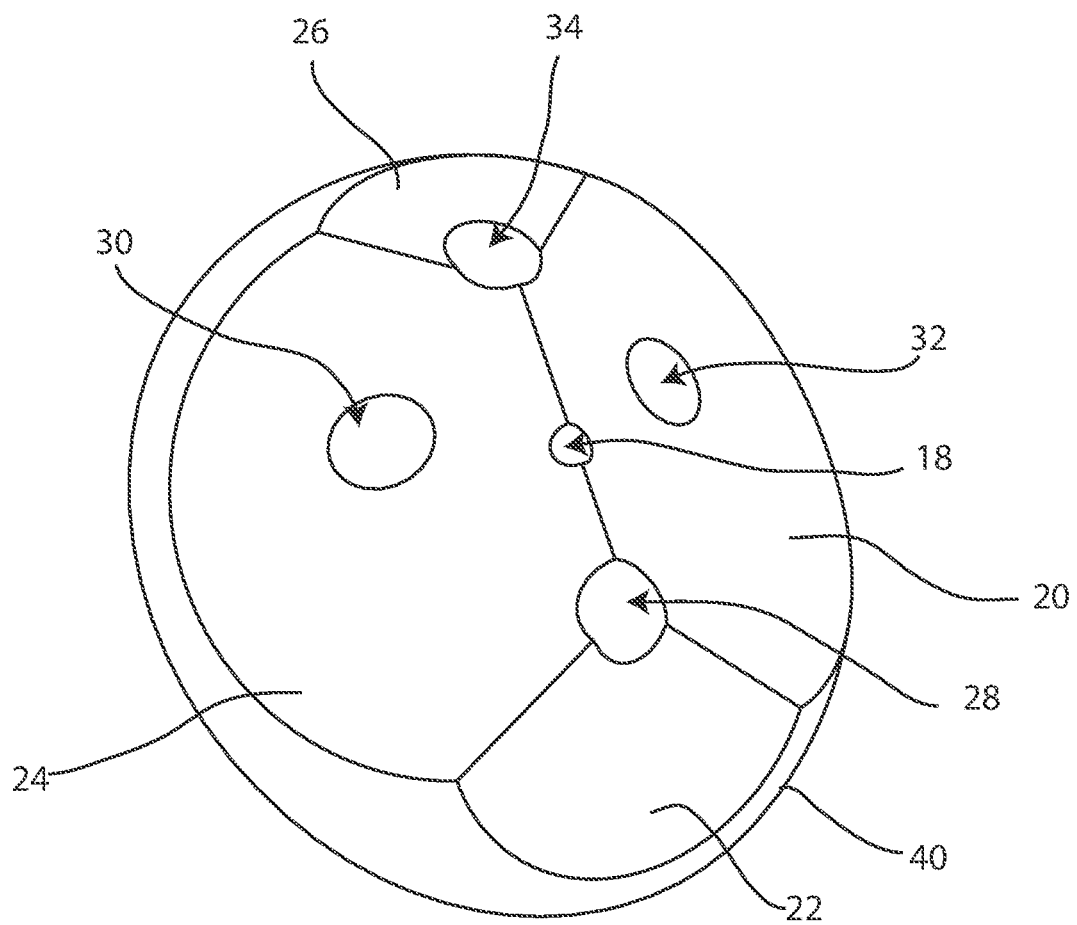
FIG. 38 is an isometric view of the simplified humeral head of FIG. 37 after superior and inferior bone resections and superior, inferior, anterior, and posterior bone holes have been made.

Referring to FIGS. 36-38, with brief reference to FIGS. 17A-18, a method of cutting superior and inferior planar bone resections 22, 26 and bone holes 28, 30, 32, 34 may occur after the method of cutting anterior and posterior planar bone resections 20, 24, and may include some or all of the steps of placing the cutting guide 2300 against the humeral head 40 so that the planar surface 2320 contacts the planar bone resection 20 and the planar surface 2324 contacts the planar bone resection 24; securing the cutting guide 2300 to the humeral head 40 by driving at least one fastener 2390, 2392, 2394 through any of the holes 2316, 2318, 2346; cutting two planar bone resections 22, 26 by actuating a saw through each slot 2322, 2326; cutting four bone holes 28, 30, 32, 34 by actuating a drill through holes 2328, 2330, 2332, 2334; and removing the fastener(s) 2390, 2392, 2394 and the cutting guide 2300. FIG. 38 shows the simplified humeral head 40 with the planar bone resections 22, 26 and bone holes 28, 30, 32, 34. Cutting guide 2300 may be replaced by cutting guide 2400 in this method, in which case the shaft 2402 and handle 2404 may be used to push the cutting guide 2400 against the humeral head 40 for added stability during one or more of the steps of securing the cutting guide 2300 to the humeral head 40; cutting two planar bone resections 22, 26; and cutting four bone holes 28, 30, 32, 34.

Figure 39:
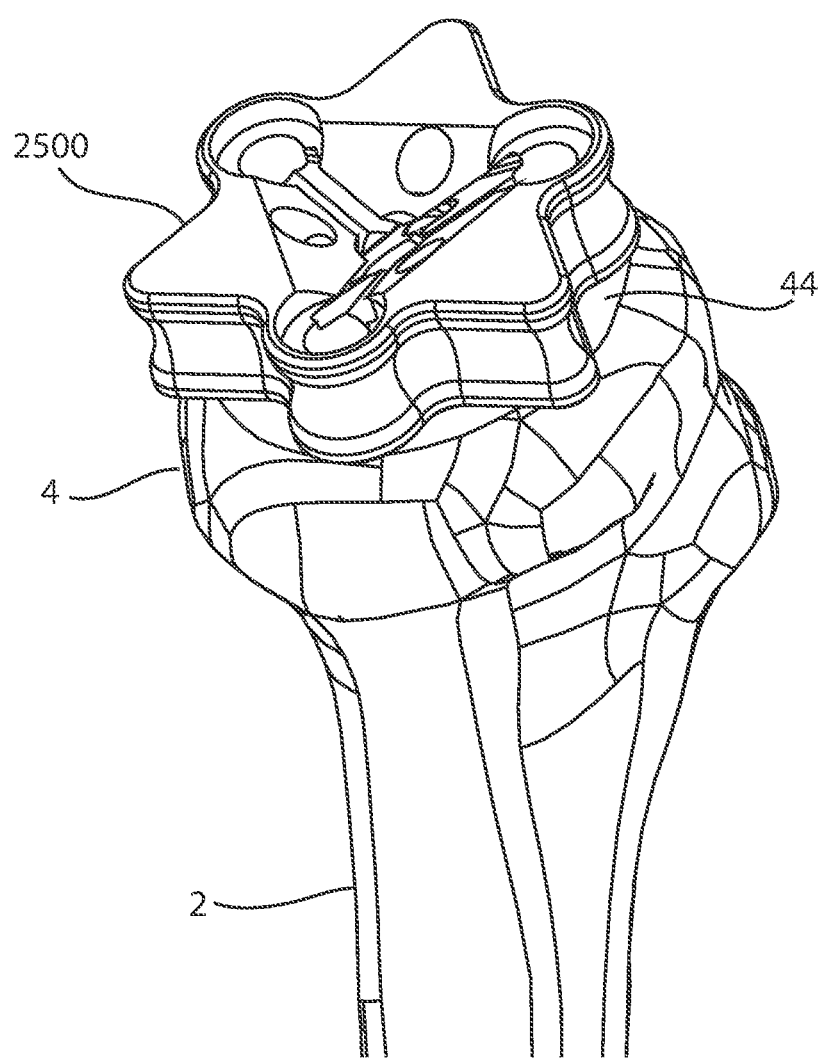
FIG. 39 is an isometric view of the cutting guide and fasteners of FIG. 19B operatively arranged with a proximal humerus.
Figure 40:
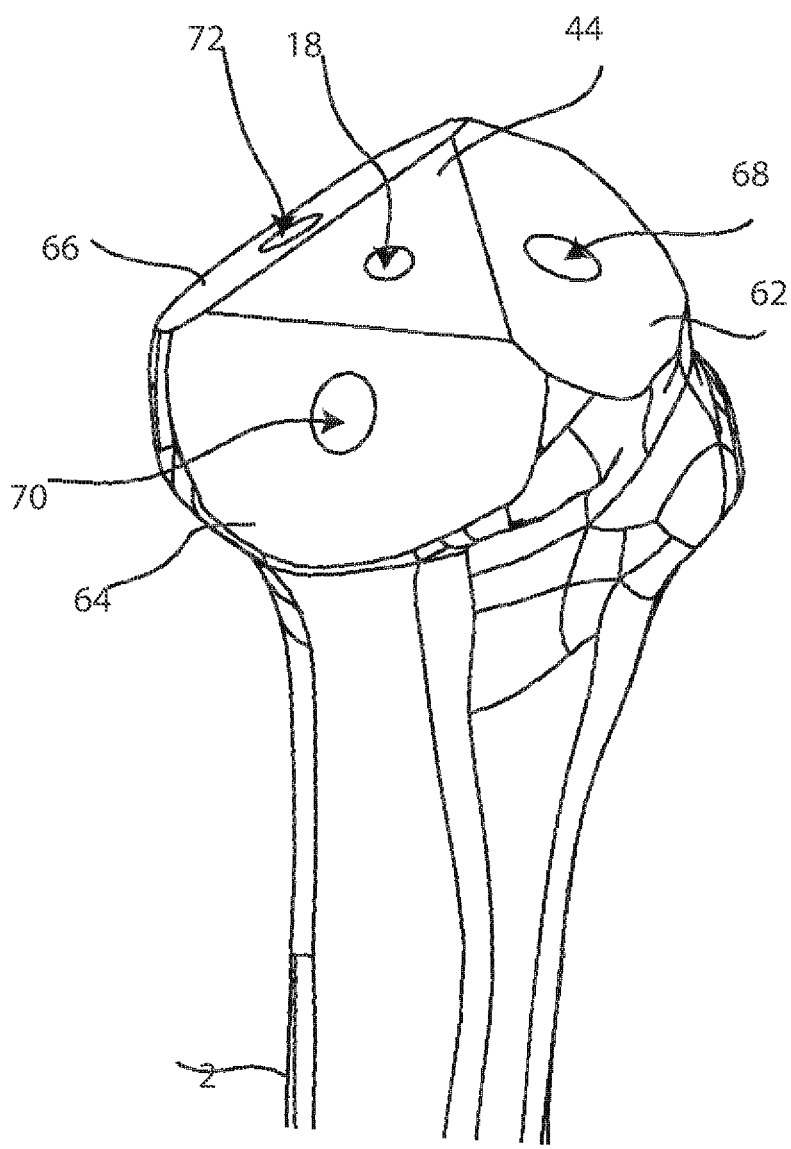
FIG. 40 is an isometric view of the proximal humerus of FIG. 39, after inferior, antero-superior, and postero-superior bone resections and bone holes have been made.

Referring to FIGS. 39-40, with brief reference to FIGS. 19A-19B, a method of cutting inferior, antero-superior, and postero-superior planar bone resections 64, 62, 66 and bone holes 70, 68, 72 may occur after the method of cutting the planar bone resection 44, and may include some or all of the steps of inserting the pin 900 into the central hole 2518 of the cutting guide 2500; advancing the cutting guide 2500 over the pin 900 to contact the humeral head 4, wherein the planar surface 2544 contacts the planar bone resection 44; securing the cutting guide 2500 to the humeral head 4 by driving at least one fastener 2590, 2592, 2594 through any of the holes 2546, 2547, 2548; removing the pin 900; cutting three planar bone resections 62, 64, 66 by actuating a saw through holes 2562, 2564, 2566; cutting three bone holes 68, 70, 72 by actuating a drill through each hole 68, 70, 72; and removing the cutting guide 2500 and fastener(s) 2590, 2592, 2594. FIG. 40 shows the humeral head 4 with the planar bone resections 62, 64, 66 and bone holes 68, 70, 72.

Figure 41:
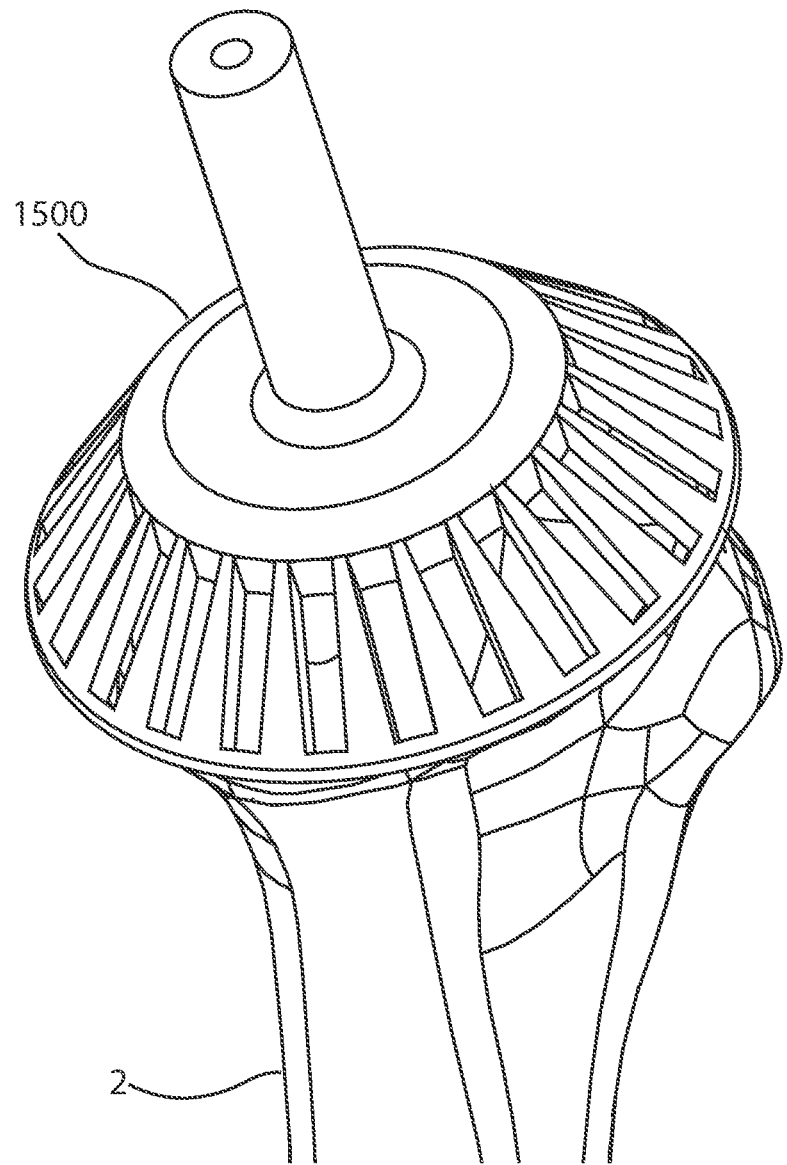
FIG. 41 is an isometric view of the conical reamer of FIG. 11A operatively arranged with the proximal humerus of FIG. 40.

Referring to FIGS. 41-42, with brief reference to FIGS. 11A-11B, a method of cutting a conical bone resection 74 may occur after any of the methods of cutting planar bone resections and/or bone holes, and is illustrated as if it occurs after the method of cutting inferior, antero-superior, and postero-superior planar bone resections 64, 62, 66 and bone holes 70, 68, 72. The method of cutting the conical bone resection 74 may include some or all of the steps of inserting the pin 900 into the cannulation 1530 of the conical reamer 1500; advancing the conical reamer 1500 over the pin 900 to contact the humeral head 4; cutting the conical bone resection 74 by actuating the conical reamer 1500 until the planar surface 1514 contacts the humeral head to stop further bone removal by the conical reamer 1500, wherein the planar surface 1514 may contact the planar surface 44; and removing the conical reamer. FIG. 42 shows the humeral head 4 with the conical bone resection 74 around the humeral head 4.

Figure 43:
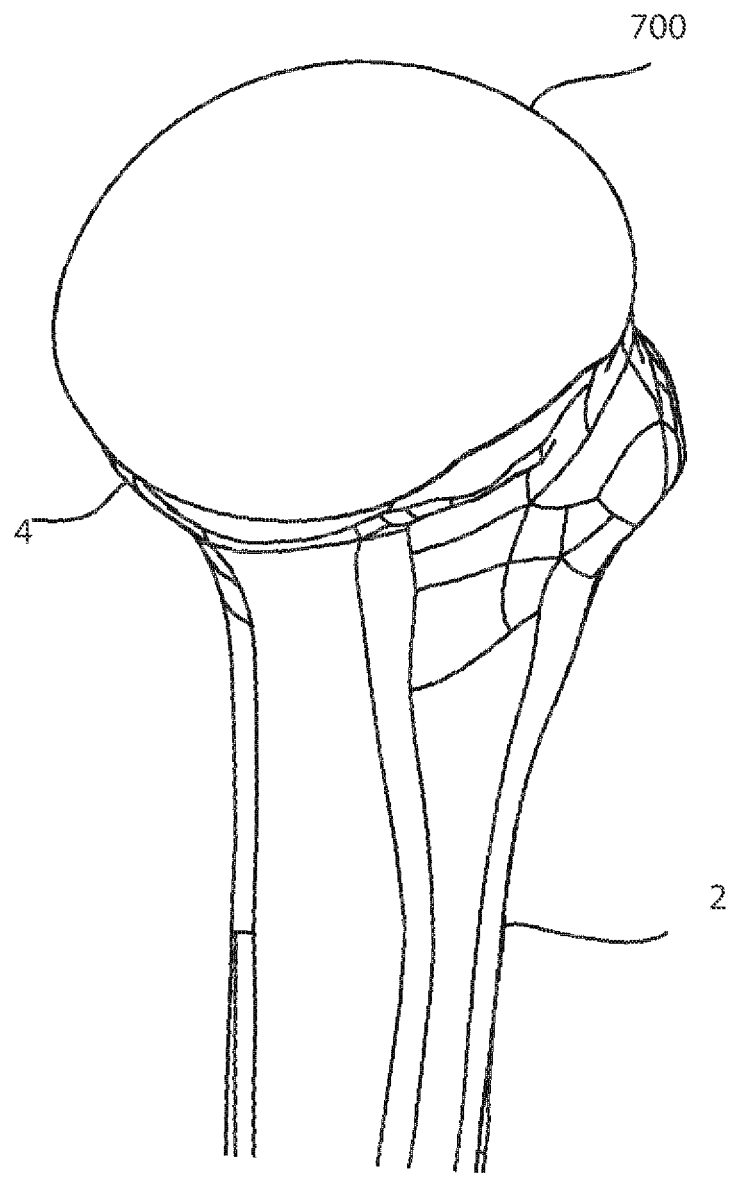
FIG. 43 is an isometric view of the proximal humerus of FIG. 42, after the humeral component of FIG. 7 has been implanted.

Referring to FIG. 43, humeral component 700 is shown implanted on the humeral head 4 of FIG. 42.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for." respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative arc mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The invention claimed is:

1. A method for reaming a planar bone resection on a humeral head and installing a prosthetic humeral component thereon, the method comprising:
   placing a working portion of a planar reamer adjacent a humeral head, the working portion comprising a bone-facing side having one or more cutting features;
   rotating a shaft of the planar reamer coupled to the working portion;
   reaming a planar bone resection on the humeral head as the working portion rotates against the humeral head;
   removing the working portion of the planar reamer from the planar bone resection reamed on humeral head;
   placing a prosthetic humeral component on the planar bone resection; and
   engaging a planar surface of the prosthetic humeral component with the planar bone resection reamed on the humeral head to install the prosthetic humeral component on the humeral head.

2. The method of claim 1, wherein the planar bone resection reamed on the humeral head is oriented perpendicular to a longitudinal axis of the shaft.

3. The method of claim 1, wherein the planar bone resection reamed on the humeral head comprises an outer diameter having a circular shape.

4. The method of claim 1, further comprising:
   aligning a longitudinal axis of a guide pin along a desired trajectory relative to the humeral head; and
   penetrating the humeral head with a distal end of the guide pin such that a proximal end of the guide pin projects away from the humeral head along the desired trajectory.

5. The method of claim 4, further comprising:
   inserting the proximal end of the guide pin into a central cannulation formed through the shaft of the planar reamer to establish a desired orientation of the working portion relative to the humeral head.

6. The method of claim 5, further comprising:
rotating the planar reamer about the guide pin placed within the central cannulation of the shaft;
translating the planar reamer distally along the guide pin and placing the bone-facing side of the working portion adjacent the humeral head; and
pressing the bone-facing side of the working portion against the humeral head during rotation to ream the planar bone resection on the humeral head.

7. The method of claim 1, wherein:
the planar surface of the prosthetic humeral component comprises a planar interior surface within a cavity defined in a bone-facing side of the prosthetic humeral component; and
placing the prosthetic humeral component on the planar bone resection comprises inserting the planar bone resection into the cavity.

8. A method for reaming a planar bone resection on a humeral head and installing a prosthetic humeral component thereon, the method comprising:
placing a working portion of a planar reamer adjacent the humeral head, the working portion comprising one or more cutting features;
rotating a shaft of the planar reamer coupled to the working portion;
reaming a planar bone resection on the humeral head as the working portion rotates against the humeral head;
removing the working portion from the humeral head;
performing at least one additional bone resection on the humeral head to remove bone from a periphery of the planar bone resection to provide a peripheral resection on the humeral head to prepare the humeral head to receive a bone-facing side of the prosthetic humeral component; and
placing the prosthetic humeral component on the humeral head such that the bone-facing side of the prosthetic humeral component receives and engages the planar bone resection and the peripheral resection.

9. The method of claim 8, wherein at least a portion of the bone-facing side of the prosthetic humeral component is configured to engage with at least a portion of the planar bone resection reamed on the humeral head.

10. The method of claim 9, wherein:
the at least a portion of the bone-facing side of the prosthetic humeral component comprises a planar surface formed on the bone-facing side of the prosthetic humeral component; and
the at least a portion of the planar bone resection is shaped to engage with the planar surface formed on the bone-facing side of the prosthetic humeral component.

11. The method of claim 9, wherein:
the at least a portion of the bone-facing side of the prosthetic humeral component comprises a line formed on the bone-facing side of the prosthetic humeral component; and
the at least a portion of the planar bone resection is shaped to engage with the line formed on the bone-facing side of the prosthetic humeral component.

12. The method of claim 8, wherein the planar bone resection reamed on the humeral head is oriented perpendicular to a longitudinal axis of the shaft.

13. The method of claim 8, wherein the planar bone resection reamed on the humeral head comprises an outer diameter having a circular shape.

14. The method of claim 8, wherein the bone-facing side of the prosthetic humeral component comprises:
a planar surface; and
a peripheral surface;
wherein placing the prosthetic humeral component on the humeral head comprises:
engaging the planar bone resection with the planar surface; and
engaging the peripheral resection with the peripheral surface.

15. The method of claim 14, wherein:
the planar surface of the prosthetic humeral component comprises a planar interior surface within a cavity defined in a bone-facing side of the prosthetic humeral component;
the peripheral surface of the prosthetic humeral component comprises a peripheral interior surface within the cavity; and
placing the prosthetic humeral component on the planar bone resection comprises inserting the planar bone resection and the peripheral resection into the cavity.

16. A method for reaming a planar bone resection on a humeral head and installing a prosthetic humeral component thereon, the method comprising:
placing a working portion of a planar reamer adjacent the humeral head, the working portion comprising one or more cutting features;
rotating a shaft of the planar reamer coupled to the working portion;
reaming the planar bone resection to a predetermined depth, as the working portion rotates against the humeral head, to remove a natural articular surface of the humeral head;
removing the working portion from the humeral head; and
placing a prosthetic humeral component on the humeral head, the prosthetic humeral component comprising an artificial articular surface;
wherein the predetermined depth of the planar bone resection determines a height at which the artificial articular surface protrudes above the planar bone resection such that the artificial articular surface replaces the natural articular surface.

17. The method of claim 16, wherein the predetermined depth for the planar bone resection reamed is determined by an inner edge formed on a perimeter rim of the planar reamer.

18. The method of claim 16, wherein the planar bone resection reamed on the humeral head is oriented perpendicular to a longitudinal axis of the shaft.

19. The method of claim 16, further comprising:
aligning a longitudinal axis of a guide pin along a desired trajectory relative to the humeral head; and
penetrating the humeral head with a distal end of the guide pin such that a proximal end of the guide pin projects away from the humeral head along the desired trajectory.

20. The method of claim 16, wherein:
the prosthetic humeral component comprises a planar interior surface within a cavity defined in a bone-facing side of the prosthetic humeral component; and
placing the prosthetic humeral component on the planar bone resection comprises inserting the planar bone resection into the cavity.

* * * * *